(12) United States Patent
Aicher et al.

(10) Patent No.: US 7,834,194 B2
(45) Date of Patent: Nov. 16, 2010

(54) CYCLOALKYL LACTAM DERIVATIVES AS INHIBITORS OF 11-BETA-HYDROXYSTEROID DEHYDROGENASE 1

(75) Inventors: Thomas Daniel Aicher, Superior, CO (US); Mark Joseph Chicarelli, Longmont, CO (US); Ronald Jay Hinklin, Longmont, CO (US); Hongqi Tian, Longmont, CO (US); Owen Brendan Wallace, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 345 days.

(21) Appl. No.: 11/722,101

(22) PCT Filed: Dec. 16, 2005

(86) PCT No.: PCT/US2005/045906

§ 371 (c)(1),
(2), (4) Date: Jun. 19, 2007

(87) PCT Pub. No.: WO2006/068991

PCT Pub. Date: Jun. 29, 2006

(65) Prior Publication Data

US 2008/0207691 A1    Aug. 28, 2008

Related U.S. Application Data

(60) Provisional application No. 60/637,895, filed on Dec. 21, 2004.

(51) Int. Cl.
*C07D 411/06* (2006.01)
*A61K 31/4025* (2006.01)

(52) U.S. Cl. ...................... 548/525; 514/422
(58) Field of Classification Search ............. 514/422; 548/525, 526
See application file for complete search history.

(56) References Cited

FOREIGN PATENT DOCUMENTS

| WO | WO 02/26706 | 4/2002 |
|---|---|---|
| WO | WO 2004/033427 | 4/2004 |
| WO | WO 2004/041776 | 5/2004 |
| WO | WO 2005/108361 | 11/2005 |

OTHER PUBLICATIONS

Bydal et. al. "Inhibition of type 2 17B-hydroxysteroid dehydrogenase by estradiol derivatives bearing a lactone on the D-ring: structure—activity relationships" Steroids 2004, 69, 325-342.*

Martin, Yvonne C. et. al. "Do Structurally Similar Molecules Have Similar Biological Activity?" Journal of Medicinal Chemistry 2002, 45, 4350-4358.*
Messinger, J. et. al. "New inhibitors of 17-hydroxysteroid dehydrogenase type 1" Molecular and Cellular Endocrinology 2006, 248, 192-198.*
Webster et. al. "Discovery and biological evaluation of adamantly amide 11b-HSD1 inhibitors" Bioorganic & Medicinal Chemistry Letters 17 (2007) 2838-2843.*
Roche et. al. "Discovery and structure—activity relationships of pentanedioic acid diamides as potent inhibitors of 11b-hydroxysteroid dehydrogenase type 1" Bioorganic & Medicinal Chemistry Letters 19 (2009) 2674-2678.*
Xiang et. al. "Synthesis and biological evaluation of sulfonamidooxazoles and B-keto sulfones: selective inhibitors of 11B-hydroxysteroid dehydrogenase type 1" Bioorganic & Medicinal Chemistry Letters 2005, 15, 2865-2869.*

* cited by examiner

*Primary Examiner*—Rita J Desai
*Assistant Examiner*—David K O'Dell
(74) *Attorney, Agent, or Firm*—Dan L. Wood; Gary M. Birch

(57) ABSTRACT

The present invention provides compounds of formula I that are useful as potent and selective inhibitors of 11-beta hydroxysteroid dehydrogenase 1. The present invention further provides a pharmaceutical composition which comprises a compound of Formula I, or a pharmaceutical salt thereof, and a pharmaceutically acceptable carrier, diluent, or excipient. In addition, the present invention provides compositions comprising compounds of formula I for the treatment of metabolic syndrome, diabetes, hyperglycemia, obesity, hypertension, hyperlipidemia, other symptoms associated with hyperglycemia, and related disorders. Formula (I) wherein, $R^0$ is (II), or (III) $G^1$ is methylene or ethylene; L is a divalent linking group selected from —$(C_1$-$C_4)$ alkylene-, —S—, —CH(OH)—, or —O—; A is methylene, —S—, —O—, or —NH—; and the other substituents are as defined in the claims.

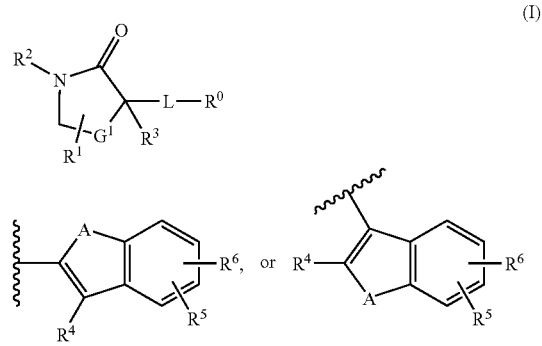

4 Claims, No Drawings

CYCLOALKYL LACTAM DERIVATIVES AS INHIBITORS OF 11-BETA-HYDROXYSTEROID DEHYDROGENASE 1

This application claims the benefit of U.S. Provisional Patent Application No. 60/637,895, filed Dec. 21, 2004.

Diabetes is caused by multiple factors and is most simply characterized by elevated levels of plasma glucose (hyperglycemia) in the fasting state. There are two generally recognized forms of diabetes: Type 1 diabetes, or insulin-dependent diabetes mellitus (IDDM), in which patients produce little or no insulin, the hormone which regulates glucose utilization, and Type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, Type 2 diabetics often develop "insulin resistance", such that the effect of insulin in stimulating glucose and lipid metabolism in the main insulin-sensitive tissues, namely, muscle, liver, and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Insulin resistance is primarily due to a receptor signaling defect that is not yet completely understood. Resistance to insulin results in insufficient activation of glucose uptake, diminished oxidation of glucose and storage of glycogen in muscle, inadequate insulin repression of lipolysis in adipose tissue, and inadequate glucose production and secretion by the liver.

Persistent or uncontrolled hyperglycemia that occurs in diabetics is associated with increased morbidity and premature mortality. Abnormal glucose homeostasis is also associated both directly and indirectly with obesity, hypertension, and alterations in lipid, lipoprotein, and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance but have not developed Type 2 diabetes are also at risk of developing "Syndrome X" or "metabolic syndrome". Syndrome X or metabolic syndrome is a condition characterized by insulin resistance, along with abdominal obesity, hyper insulinemia, high blood pressure, low HDL and High VLDL. These patients, whether or not they develop overt diabetes mellitus, are at increased risk of developing the cardiovascular complications listed above.

Evidence in rodents and humans links 11-beta hydroxysteroid dehydrogenase 1 ("11-β-HSD1") to metabolic syndrome. Evidence suggests that a drug which specifically inhibits 11-β-HSD1 in type 2 obese diabetic patients will lower blood glucose by reducing hepatic gluconeogenesis, reduce central obesity, improve atherogenic lipoprotein phenotypes, lower blood pressure, and reduce insulin resistance. Insulin effects in muscle will be enhanced, and insulin secretion from the beta cells of the islet may also be increased.

There is a continuing need for new methods of treating diabetes and related conditions, such as metabolic syndrome. It is an object of this invention to meet this and other needs.

SUMMARY OF THE INVENTION

The present invention provides a compound structurally represented by formula I:

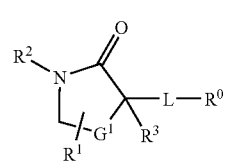

or a pharmaceutically acceptable salt thereof wherein $R^0$ is

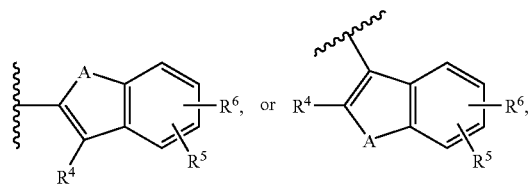

wherein the zig-zag mark represents the point of attachment to the $R^0$ position in Formula I;

$G^1$ is methylene or ethylene;

L is a divalent linking group selected from —($C_1$-$C_4$)alkylene-, —S—, —CH(OH)—, or —O—;

A is methylene, —S—, —O—, or —NH—;

$R^1$ is

Hydrogen, hydroxy, —($C_1$-$C_4$)alkyl(optionally substituted with one to three halogens), —($C_1$-$C_4$)alkoxy(optionally substituted with one to three halogens), or —$CH_2OR^7$ wherein $R^7$ is hydrogen or —($C_1$-$C_4$)alkyl (optionally substituted with one to three halogens);

$R^2$ is

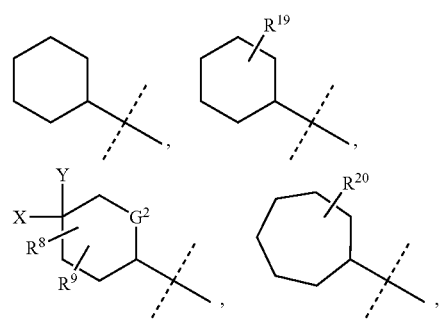

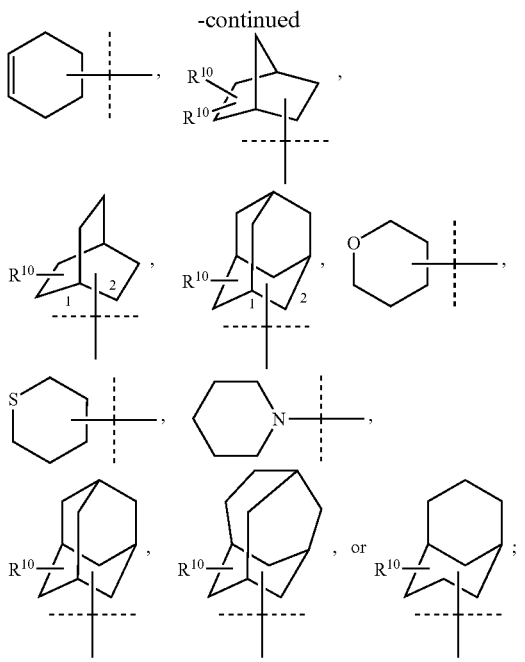

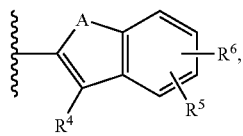

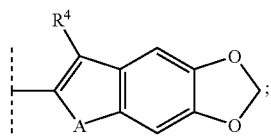

wherein the dashed line indicates the point of attachment to the $R^2$ position in formula I; $G^2$ is methylene, ethylene, or 1-propylene; X is hydrogen, hydroxyl, or —$CH_2OH$; Y is hydrogen or methyl, provided that at least one of X and Y is not hydrogen; or X and Y together with the carbon to which they are attached form a carbonyl; $R^8$ and $R^9$ are each independently hydrogen, hydroxy, or —($C_1$-$C_4$)alkyl(optionally substituted with one to three halogens); $R^{10}$ is hydrogen, hydroxy, or —($C_1$-$C_4$)alkyl (optionally substituted with one to three halogens);

$R^3$ is
hydrogen, hydroxy (provided that when L is —S— or —CH(OH)— then $R^3$ cannot be hydroxy), or —($C_1$-$C_4$)alkyl;

$R^4$ is
hydrogen, hydroxy, —($C_1$-$C_4$)alkyl(optionally substituted with one to three halogens), —($C_1$-$C_4$)alkoxy, halo, cyano, —$SCF_3$, —$OCF_3$, $Ar^1$, $Het^1$, $Ar^1$—($C_1$-$C_4$)alkyl, $Het^1$-($C_1$-$C_4$)alkyl, —($C_1$-$C_4$)alkyl-C(O)OH, —($C_1$-$C_4$)alkyl-C(O)O—($C_1$-$C_4$)alkyl, —($C_1$-$C_4$)alkyl-OH, or —($C_1$-$C_4$)alkyl-C(O)N($R^{11}$)($R^{12}$); wherein $R^{11}$ and $R^{12}$ are each independently hydrogen or —($C_1$-$C_4$)alkyl, or $R^{11}$ and $R^{12}$ taken together with the nitrogen to which they are attached form piperidinyl or pyrrolidinyl;

$R^5$ is
hydrogen, hydroxy, —($C_1$-$C_4$)alkyl(optionally substituted with one to three halogens), —($C_1$-$C_4$)alkoxy(optionally substituted with one to three halogens), halo, cyano, —$SCF_3$, —$OCF_3$, $Ar^1$, $Het^1$, $Ar^1$—($C_1$-$C_4$)alkyl, $Het^1$-($C_1$-$C_4$)alkyl, —($C_1$-$C_4$)alkyl-C(O)OH, —($C_1$-$C_4$)alkyl-C(O)O—($C_1$-$C_4$)alkyl, —($C_1$-$C_4$)alkyl-OH, or —($C_1$-$C_4$)alkyl-C(O)N($R^{11}$)($R^{12}$); wherein $R^{11}$ and $R^{12}$ are each independently hydrogen or —($C_1$-$C_4$)alkyl, or $R^{11}$ and $R^{12}$ taken together with the nitrogen to which they are attached form piperidinyl or pyrrolidinyl $R^6$ is
hydrogen, hydroxy, —($C_1$-$C_4$)alkyl(optionally substituted with one to three halogens), —($C_1$-$C_4$)alkoxy(option-ally substituted with one to three halogens), halo, cyano, $Ar^2$, $Het^1$, $Het^2$, $Ar^2$—($C_1$-$C_4$)alkyl, $Het^2$—($C_1$-$C_4$)alkyl, —C(O)—($C_1$-$C_4$)alkyl, —C(O)—$Ar^2$, —C(O)—$Het^2$, —($C_1$-$C_4$)alkyl-N($R^{13}$)($R^{14}$), —O—($C_1$-$C_4$)alkyl-$Ar^2$, —O—($C_1$-$C_4$)alkyl-C(O)OH, or —O—($C_1$-$C_4$)alkyl-N($R^{13}$)($R^{14}$); wherein $R^{13}$ and $R^{14}$ are each independently hydrogen or —($C_1$-$C_4$)alkyl, or $R^{13}$ and $R^{14}$ taken together with the nitrogen to which they are attached form piperidinyl or pyrrolidinyl; or when $R^0$ is then $R^5$ and $R^6$ may combine with the ring atoms to which they are attached to form $Ar^1$ is phenyl or naphthyl;

$Ar^2$ is
$Ar^1$ optionally substituted with from one to three moieties independently selected from halo, hydroxy, cyano, —($C_1$-$C_4$)alkyl(optionally substituted with one to three halogens), —C(O)OH, —C(O)OCH$_3$, —($C_1$-$C_4$)alkyl-C(O)OH, —O—($C_1$-$C_4$)alkyl-C(O)OH, —($C_1$-$C_4$)alkyl-N($R^{15}$)($R^{16}$), —O—($C_1$-$C_4$)alkyl-N($R^{15}$)($R^{16}$), imidazolyl, pyridinyl, or —($C_1$-$C_4$)alkyl-imidazolyl; wherein $R^{15}$ and $R^{16}$ are each independently hydrogen or —($C_1$-$C_4$)alkyl, or $R^{15}$ and $R^{16}$ taken together with the nitrogen to which they are attached form piperidinyl or pyrrolidinyl;

$Het^1$ is
a heterocyclic radical selected from pyridinyl, piperidinyl, pyrimidinyl, pyrazinyl, piperazinyl, pyridazinyl, indolyl, isoindolyl, indolinyl, furanyl, benzofuranyl, thiazolyl, oxazolyl, isoxazolyl, isothiazolyl, benzothiophenyl, thiophenyl, quinolinyl, isoquinolinyl, quinoxalinyl, quinazolinyl, or phthalazinyl;

$Het^2$ is
$Het^1$ optionally substituted with from one to three moieties independently selected from halo, hydroxy, cyano, —($C_1$-$C_4$)alkyl(optionally substituted with one to three halogens), —C(O)OH, —C(O)OCH$_3$, —($C_1$-$C_4$)alkyl-C(O)OH, —O—($C_1$-$C_4$)alkyl)C(O)OH, —($C_1$-$C_4$)alkyl-N($R^{17}$)($R^{11}$), —O—($C_1$-$C_4$)alkyl-N($R^{17}$)($R^{18}$), imidazolyl, pyridinyl, or —($C_1$-$C_4$)alkyl-imidazolyl; wherein $R^{17}$ and $R^{18}$ are each independently hydrogen or —($C_1$-$C_4$)alkyl, or $R^{17}$ and $R^{18}$ taken together with the nitrogen to which they are attached form piperidinyl or pyrrolidinyl;

$R^{19}$ is
hydroxy, —($C_1$-$C_4$)alkyl(optionally substituted with one to three halogens), or —$CH_2OH$; and $R^{20}$ is Hydrogen, hydroxy, —($C_1$-$C_4$)alkyl(optionally substituted with one to three halogens), or —$CH_2OH$.

The present invention provides compounds of formula I that are useful as potent and selective inhibitors of 11-beta hydroxysteroid dehydrogenase 1. The present invention further provides a pharmaceutical composition which comprises a compound of Formula I, or a pharmaceutical salt thereof, and a pharmaceutically acceptable carrier, diluent, or excipient. In addition, the present invention provides a method for the treatment of metabolic syndrome, and related disorders, which comprise administering to a patient in need thereof an effective amount of a compound of formula I or a pharmaceutically acceptable salt thereof.

Due to their inhibition of 11-beta hydroxysteroid dehydrogenase 1, the present compounds are useful in the treatment of a wide range of conditions and disorders in which inhibition of 11-beta hydroxysteroid dehydrogenase 1 is beneficial. These disorders and conditions are defined herein as "diabetic disorders" and "metabolic syndrome disorders". One of skill in the art is able to identify "diabetic disorders" and "metabolic syndrome disorders" by the involvement of 11-beta hydroxysteroid dehydrogenase 1 activity either in the pathophysiology of the disorder, or in the homeostatic response to the disorder. Thus, the compounds may find use for example to prevent, treat, or alleviate, diseases or conditions or associated symptoms or sequelae, of "Diabetic disorders" and "metabolic syndrome disorders".

"Diabetic disorders" and "metabolic syndrome disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, wound healing, impaired glucose tolerance (IGT), insulin resistance syndromes, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc. Thus, the present invention also provides a method of treatment of "Diabetic disorders" and "metabolic syndrome disorders" while reducing and or eliminating one or more of the unwanted side effects associated with the current treatments.

Thus the present invention also provides a method of treatment of a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) osteoporosis, as well as other conditions and disorders where insulin resistance is a component, in a patient in need of such treatment, comprising administering to said patient a therapeutically effective amount of a compound of formula (I) or a pharmaceutically acceptable salt thereof.

DETAILED DESCRIPTION OF THE INVENTION

General terms used in the description of compounds herein described bear their usual meanings.

As used herein, the term "($C_1$-$C_4$)alkyl" refers to straight-chain or branched-chain saturated aliphatic groups of 1 to 4 carbon atoms including methyl, ethyl, n-propyl, isopropyl, n-butyl, isobutyl, sec-butyl, t-butyl, and the like.

Similarly, the term "($C_1$-$C_4$)alkoxy" represents a $C_1$-$C_4$ alkyl group attached through an oxygen atom and examples include methoxy, ethoxy, n-propoxy, isopropoxy, and the like.

The term "—($C_1$-$C_4$)alkylene-" refers to straight-chain or branched-chain saturated divalent aliphatic groups such as methylene, ethylene, n-propylene, gemdimethyl methylene, and the like.

The term "halogen" refers to fluoro, chloro, bromo, and iodo.

"$HET^1$" and "$HET^2$" may be attached at any point which affords a stable structure.

The term "optionally substituted," or "optional substituents," as used herein, means that the groups in question are either unsubstituted or substituted with one or more of the substituents specified. When the groups in question are substituted with more than one substituent, the substituents may be the same or different. The terms "independently," "independently are," and "independently selected from" mean that the groups in question may be the same or different. Certain of the herein defined terms may occur more than once in the structural formulae, and upon such occurrence each term shall be defined independently of the other.

As used herein, the term "patient" refers to a warm-blooded animal or mammal that has or is at risk of developing a disease selected from (1) through (20) described below. It is understood that guinea pigs, dogs, cats, rats, mice, hamsters, and primates, including humans, are examples of patients within the scope of the meaning of the term "patient". The term "patient" includes and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The terms "treatment", "treating" and "treat", as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present method includes both medical therapeutic and/or prophylactic treatment, as appropriate.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation " ⎯ " refers to a bond that protrudes forward out of the plane of the page.

The designation " ⋯⋯ " refers to a bond that protrudes backward out of the plane of the page.

The designation " ⁓⁓ " refers to a bond wherein the stereochemistry is not defined.

In one embodiment, the present invention provides a compound of Formula I, or a pharmaceutically acceptable salt thereof, as described in detail above. While all of the compounds of the present invention are useful, certain of the compounds are particularly interesting and are preferred. The following listings set out several groups of preferred embodiments.

In a preferred embodiment, the present invention provides a compound structurally represented by formula I, or a pharmaceutically acceptable salt thereof, wherein $R^0$ is

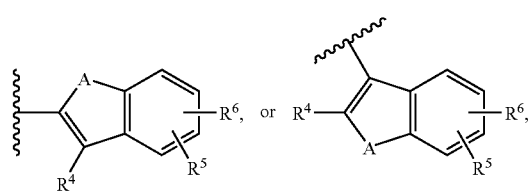

wherein the zig-zag mark represents the point of attachment to the $R^0$ position in Formula I;

$G^1$ is methylene or ethylene;

L is —$CH_2$—;

A is —$CH_2$—, —S—, —O—, or —NH—;

$R^1$ is hydrogen;

$R^2$ is

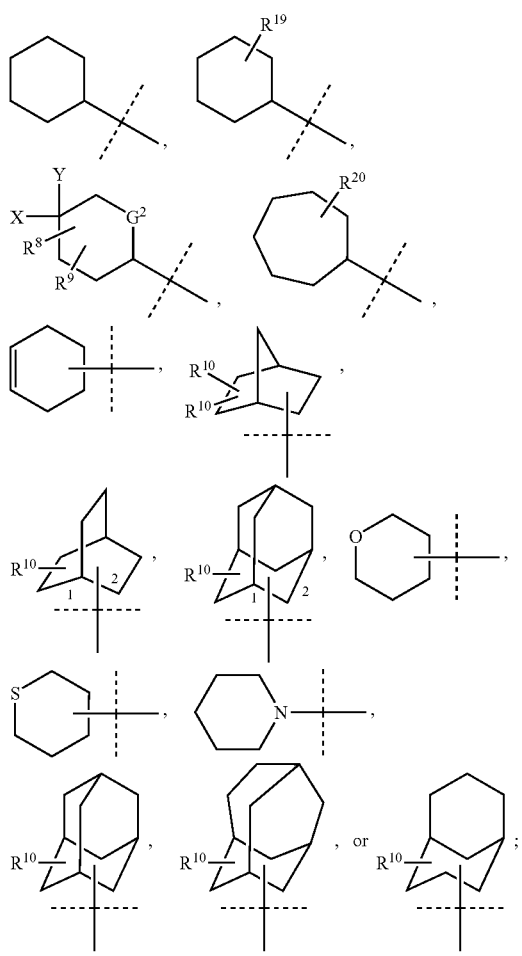

wherein the dashed line indicates the point of attachment to the $R^2$ position in formula I; $G^2$ is methylene, ethylene, or 1-propylene; X is hydrogen, hydroxyl, or —CH$_2$OH; Y is hydrogen or methyl, provided that at least one of X and Y is not hydrogen; or X and Y together with the carbon to which they are attached form a carbonyl; $R^8$ and $R^9$ are each independently hydrogen, hydroxy, or —(C$_1$-C$_4$)alkyl(optionally substituted with one to three halogens); $R^{10}$ is hydrogen, hydroxy, or —(C$_1$-C$_4$)alkyl (optionally substituted with one to three halogens);

$R^3$ is hydrogen;

$R^4$ is
hydrogen, hydroxy, —(C$_1$-C$_4$)alkyl(optionally substituted with one to three halogens), —(C$_1$-C$_4$)alkoxy, halo, cyano, —SCF$_3$, —OCF$_3$, —(C$_1$-C$_4$)alkyl-C(O)OH, —(C$_1$-C$_4$)alkyl-C(O)O—(C$_1$-C$_4$)alkyl, —(C$_1$-C$_4$)alkyl-OH, or —(C$_1$-C$_4$)alkyl-C(O)N(R$^{11}$)(R$^{12}$); wherein R$^{11}$ and R$^{12}$ are each independently hydrogen or —(C$_1$-C$_4$)alkyl, or R$^{11}$ and R$^{12}$ taken together with the nitrogen to which they are attached form piperidinyl or pyrrolidinyl;

$R^5$ is
hydrogen, hydroxy, —(C$_1$-C$_4$)alkyl(optionally substituted with one to three halogens), —(C$_1$-C$_4$)alkoxy(optionally substituted with one to three halogens), halo, cyano, —SCF$_3$, —OCF$_3$, —(C$_1$-C$_4$)alkyl-C(O)OH, —(C$_1$-C$_4$)alkyl-C(O)O—(C$_1$-C$_4$)alkyl, —(C$_1$-C$_4$)alkyl-OH, or —(C$_1$-C$_4$)alkyl-C(O)N(R$^{11}$)(R$^{12}$); wherein R$^{11}$ and R$^{12}$ are each independently hydrogen or —(C$_1$-C$_4$)alkyl, or R$^{11}$ and R$^{12}$ taken together with the nitrogen to which they are attached form piperidinyl or pyrrolidinyl $R^6$ is
hydrogen, hydroxy, —(C$_1$-C$_4$)alkyl(optionally substituted with one to three halogens), —(C$_1$-C$_4$)alkoxy(optionally substituted with one to three halogens), halo, cyano, Ar$^2$, Het$^1$, Het$^2$, Ar$^2$—(C$_1$-C$_4$)alkyl, Het$^2$-(C$_1$-C$_4$)alkyl, —C(O)—(C$_1$-C$_4$)alkyl, —C(O)—Ar$^2$, —C(O)—Het$^2$, —(C$_1$-C$_4$)alkyl-N(R$^{13}$)(R$^{14}$), —O—(C$_1$-C$_4$)alkyl-Ar$^2$, —O—(C$_1$-C$_4$)alkyl-C(O)OH, or —O—(C$_1$-C$_4$)alkyl-N(R$^{13}$)(R$^{14}$); wherein R$^{13}$ and R$^{14}$ are each independently hydrogen or —(C$_1$-C$_4$)alkyl, or R$^{13}$ and R$^{14}$ taken together with the nitrogen to which they are attached form piperidinyl or pyrrolidinyl; or when $R^0$ is

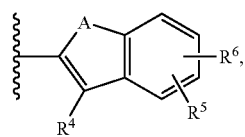

then $R^5$ and $R^6$ may combine with the ring atoms to which they are attached to form

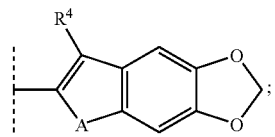

Ar$^1$ is phenyl;

Ar$^2$ is
Ar$^1$ optionally substituted with from one to three moieties independently selected from halo, hydroxy, cyano, —(C$_1$-C$_4$)alkyl(optionally substituted with one to three halogens), —C(O)OH, —C(O)OCH$_3$, —(C$_1$-C$_4$)alkyl-C(O)OH, —O—(C$_1$-C$_4$)alkyl-C(O)OH, —(C$_1$-C$_4$)alkyl-N(R$^{15}$)(R$^{16}$), —O—(C$_1$-C$_4$)alkyl-N(R$^{15}$)(R$^{16}$), imidazolyl, pyridinyl, or —(C$_1$-C$_4$)alkyl-imidazolyl; wherein R$^{15}$ and R$^{16}$ are each independently hydrogen or —(C$_1$-C$_4$)alkyl, or R$^{15}$ and R$^{16}$ taken together with the nitrogen to which they are attached form piperidinyl or pyrrolidinyl;

Het$^1$ is
a heterocyclic radical selected from pyridinyl, piperidinyl, pyrimidinyl, pyrazinyl, piperazinyl, pyridazinyl, indolyl, isoindolyl, indolinyl, furanyl, benzofuranyl, thiazolyl, oxazolyl, isoxazolyl, isothiazolyl, benzothiophenyl, thiophenyl, quinolinyl, isoquinolinyl, quinoxalinyl, quinazolinyl, or phthalazinyl;

Het$^2$ is
Het$^1$ optionally substituted with from one to three moieties independently selected from halo, hydroxy, cyano, —(C$_1$-C$_4$)alkyl(optionally substituted with one to three halogens), —C(O)OH, —C(O)OCH$_3$, —(C$_1$-C$_4$)alkyl-C(O)OH, —O—(C$_1$-C$_4$)alkyl)C(O)OH, —(C$_1$-C$_4$)alkyl-N(R$^{17}$)(R$^{18}$), —O—(C$_1$-C$_4$)alkyl-N(R$^{17}$)(R$^{18}$), imidazolyl, pyridinyl, or —(C$_1$-C$_4$)alkyl-imidazolyl; wherein R$^{17}$ and R$^{18}$ are each independently hydrogen or —(C$_1$-C$_4$)alkyl, or R$^{17}$ and R$^{18}$ taken together with the nitrogen to which they are attached form piperidinyl or pyrrolidinyl;

R$^{19}$ is
hydroxy, —(C$_1$-C$_4$)alkyl(optionally substituted with one to three halogens), or —CH$_2$OH; and R$^{20}$ is
Hydrogen, hydroxy, —(C$_1$-C$_4$)alkyl(optionally substituted with one to three halogens), or —CH$_2$OH.

In a preferred embodiment, the present invention provides a compound structurally represented by formula I, or a pharmaceutically acceptable salt thereof, wherein R$^0$ is

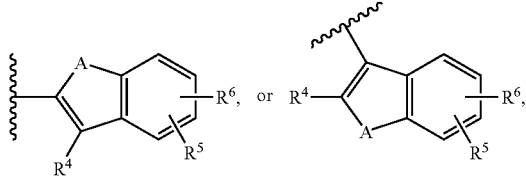

wherein the zig-zag mark represents the point of attachment to the R$^0$ position in Formula I;

G$^1$ is methylene;

L is —CH$_2$—;

A is —CH$_2$—, —S—, —O—, or —NH—;

R$^1$ is hydrogen;

R$^2$ is

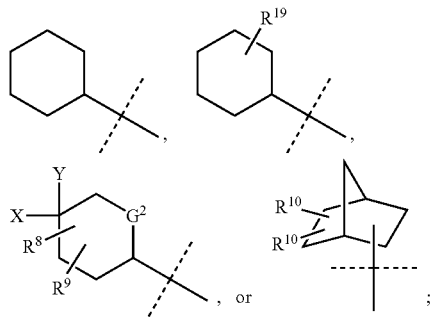

wherein the dashed line indicates the point of attachment to the R$^2$ position in formula I; G$^2$ is methylene, X is hydrogen or —CH$_2$OH; Y is hydrogen or methyl, provided that at least one of X and Y is not hydrogen; or X and Y together with the carbon to which they are attached form a carbonyl; R$^8$ and R$^9$ are each independently hydrogen, hydroxy, or —(C$_1$-C$_4$)alkyl(optionally substituted with one to three halogens); R$^{10}$ is hydrogen, hydroxy, or —(C$_1$-C$_4$)alkyl(optionally substituted with one to three halogens);

R$^3$ is hydrogen;

R$^4$ is
hydrogen, —CH$_3$ (optionally substituted with one to three halogens), or halo;

R$^5$ is
hydrogen, or halo;

R$^6$ is
hydrogen, hydroxy, —(C$_1$-C$_4$)alkyl(optionally substituted with one to three halogens), —(C$_1$-C$_4$)alkoxy(optionally substituted with one to three halogens), halo, cyano, Ar$^2$, Het$^1$, Het$^2$, Ar$^2$—(C$_1$-C$_4$)alkyl, Het$^2$-(C$_1$-C$_4$)alkyl, —C(O)—(C$_1$-C$_4$)alkyl, —C(O)—Ar$^2$, —C(O)—Het$^2$, —(C$_1$-C$_4$)alkyl-N(R$^{13}$)(R$^{14}$), —O—(C$_1$-C$_4$)alkyl-Ar$^2$, —O—(C$_1$-C$_4$)alkyl-C(O)OH, or —O—(C$_1$-C$_4$)alkyl-N(R$^{13}$)(R$^{14}$); wherein R$^{13}$ and R$^{14}$ are each independently hydrogen or —(C$_1$-C$_4$)alkyl, or R$^{13}$ and R$^{14}$ taken together with the nitrogen to which they are attached form piperidinyl or pyrrolidinyl; or when R$^0$ is

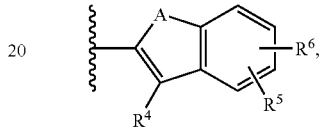

then R$^5$ and R$^6$ may combine with the ring atoms to which they are attached to form

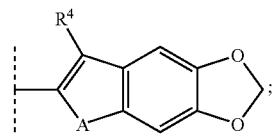

Ar$^1$ is phenyl;

Ar$^2$ is
Ar$^1$ optionally substituted with from one to three moieties independently selected from halo, hydroxy, cyano, —(C$_1$-C$_4$)alkyl(optionally substituted with one to three halogens), —C(O)OH, —C(O)OCH$_3$, —(C$_1$-C$_4$)alkyl-C(O)OH, —O—(C$_1$-C$_4$)alkyl-C(O)OH, —(C$_1$-C$_4$)alkyl-N(R$^{15}$)(R$^{16}$), —O—(C$_1$-C$_4$)alkyl-N(R$^{15}$)(R$^{16}$); wherein R$^{15}$ and R$^{16}$ are each independently hydrogen or —(C$_1$-C$_4$)alkyl, or R$^{15}$ and R$^{16}$ taken together with the nitrogen to which they are attached form piperidinyl or pyrrolidinyl;

Het$^1$ is
a heterocyclic radical selected from pyridinyl, piperidinyl, pyrimidinyl, pyrazinyl, piperazinyl, pyridazinyl, indolyl, isoindolyl, indolinyl, furanyl, thiazolyl, oxazolyl, isoxazolyl, isothiazolyl, thiophenyl;

Het$^2$ is
Het$^1$ optionally substituted with from one to three moieties independently selected from halo, hydroxy, cyano, —(C$_1$-C$_4$)alkyl(optionally substituted with one to three halogens), —C(O)OH, —C(O)OCH$_3$, —(C$_1$-C$_4$)alkyl-C(O)OH, —O—(C$_1$-C$_4$)alkyl)C(O)OH, —(C$_1$-C$_4$)alkyl-N(R$^{17}$)(R$^{18}$), —O—(C$_1$-C$_4$)alkyl-N(R$^{17}$)(R$^{18}$); wherein R$^{17}$ and R$^{18}$ are each independently hydrogen or —(C$_1$-C$_4$)alkyl, or R$^{17}$ and R$^{18}$ taken together with the nitrogen to which they are attached form piperidinyl or pyrrolidinyl;

$R^{19}$ is hydroxy, —($C_1$-$C_4$)alkyl(optionally substituted with one to three halogens), or —$CH_2OH$; and $R^{20}$ is Hydrogen, hydroxy, —($C_1$-$C_4$)alkyl(optionally substituted with one to three halogens), or —$CH_2OH$.

In a preferred embodiment, the present invention provides a compound structurally represented by formula I, or a pharmaceutically acceptable salt thereof, wherein $R^0$ is

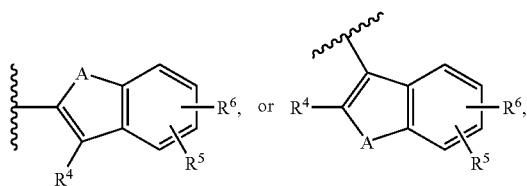

wherein the zig-zag mark represents the point of attachment to the $R^0$ position in Formula I;

$G^1$ is ethylene;

L is —$CH_2$—;

A is —$CH_2$—, —S—, —O—, or —NH—;

$R^1$ is hydrogen;

$R^2$ is

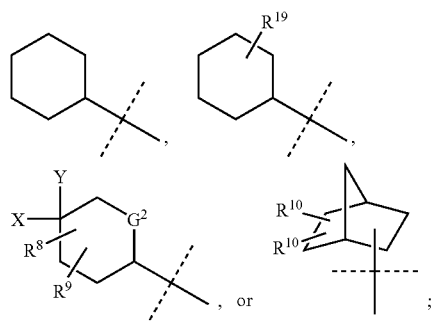

wherein the dashed line indicates the point of attachment to the $R^2$ position in formula I; $G^2$ is methylene, X is hydrogen or —$CH_2OH$; Y is hydrogen or methyl, provided that at least one of X and Y is not hydrogen; or X and Y together with the carbon to which they are attached form a carbonyl; $R^8$ and $R^9$ are each independently hydrogen, hydroxy, or —($C_1$-$C_4$)alkyl(optionally substituted with one to three halogens); $R^{10}$ is hydrogen, hydroxy, or —($C_1$-$C_4$)alkyl(optionally substituted with one to three halogens);

$R^3$ is hydrogen;

$R^4$ is hydrogen, —$CH_3$ (optionally substituted with one to three halogens), or halo;

$R^5$ is hydrogen, or halo;

$R^6$ is hydrogen, hydroxy, —($C_1$-$C_4$)alkyl(optionally substituted with one to three halogens), —($C_1$-$C_4$)alkoxy(optionally substituted with one to three halogens), halo, cyano, $Ar^2$, $Het^1$, $Het^2$, $Ar^2$—($C_1$-$C_4$)alkyl, $Het^2$—($C_1$-$C_4$)alkyl, —C(O)—($C_1$-$C_4$)alkyl, —C(O)—$Ar^2$, —C(O)—$Het^2$, —($C_1$-$C_4$)alkyl-N($R^{13}$)($R^{14}$), —O—($C_1$-$C_4$)alkyl-$Ar^2$, —O—($C_1$-$C_4$)alkyl-C(O)OH, or —O—($C_1$-$C_4$)alkyl-N($R^{13}$)($R^{14}$); wherein $R^{13}$ and $R^{14}$ are each independently hydrogen or —($C_1$-$C_4$)alkyl, or $R^{13}$ and $R^{14}$ taken together with the nitrogen to which they are attached form piperidinyl or pyrrolidinyl; or when $R^0$ is

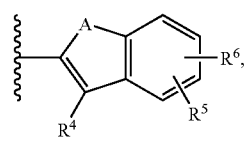

then $R^5$ and $R^6$ may combine with the ring atoms to which they are attached to form

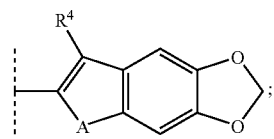

$Ar^1$ is phenyl;

$Ar^1$ is $Ar^1$ optionally substituted with from one to three moieties independently selected from halo, hydroxy, cyano, —($C_1$-$C_4$)alkyl(optionally substituted with one to three halogens), —C(O)OH, —C(O)OCH_3, —($C_1$-$C_4$)alkyl-C(O)OH, —O—($C_1$-$C_4$)alkyl-C(O)OH, —($C_1$-$C_4$)alkyl-N($R^{15}$)($R^6$), —O—($C_1$-$C_4$)alkyl-N($R^{15}$)($R^{16}$); wherein $R^{15}$ and $R^{16}$ are each independently hydrogen or —($C_1$-$C_4$)alkyl, or $R^{15}$ and $R^{16}$ taken together with the nitrogen to which they are attached form piperidinyl or pyrrolidinyl;

$Het^1$ is a heterocyclic radical selected from pyridinyl, piperidinyl, pyrimidinyl, pyrazinyl, piperazinyl, pyridazinyl, indolyl, isoindolyl, indolinyl, furanyl, thiazolyl, oxazolyl, isoxazolyl, isothiazolyl, thiophenyl;

$Het^2$ is $Het^1$ optionally substituted with from one to three moieties independently selected from halo, hydroxy, cyano, —($C_1$-$C_4$)alkyl(optionally substituted with one to three halogens), —C(O)OH, —C(O)OCH_3, —($C_1$-$C_4$)alkyl-C(O)OH, —O—($C_1$-$C_4$)alkyl)C(O)OH, —($C_1$-$C_4$)alkyl-N($R^{17}$)($R^{18}$), —O—($C_1$-$C_4$)alkyl-N($R^{17}$)($R^{18}$); wherein $R^{17}$ and $R^{18}$ are each independently hydrogen or —($C_1$-$C_4$)alkyl, or $R^{17}$ and $R^{18}$ taken together with the nitrogen to which they are attached form piperidinyl or pyrrolidinyl;

$R^{19}$ is hydroxy, —($C_1$-$C_4$)alkyl(optionally substituted with one to three halogens), or —$CH_2OH$; and $R^{20}$ is Hydrogen, hydroxy, —($C_1$-$C_4$)alkyl(optionally substituted with one to three halogens), or —$CH_2OH$.

In a preferred embodiment, the present invention provides a compound structurally represented by formula I, or a pharmaceutically acceptable salt thereof, wherein $R^0$ is

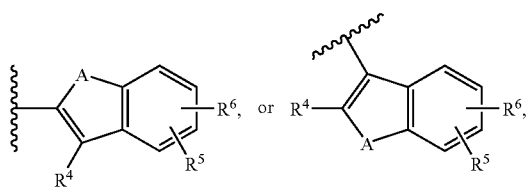

wherein the zig-zag mark represents the point of attachment to the $R^0$ position in Formula I;

$G^1$ is methylene;

L is —$CH_2$—;

A is —S—, or —O—;

$R^1$ is hydrogen;

$R^2$ is

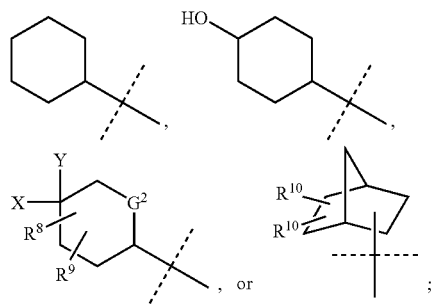

wherein the dashed line indicates the point of attachment to the $R^2$ position in formula I; $G^2$ is methylene, X and Y together with the carbon to which they are attached form a carbonyl; $R^8$ and $R^9$ are each independently hydrogen; $R^{10}$ is hydrogen;

$R^3$ is hydrogen;

$R^4$ is hydrogen, —$CH_3$ (optionally substituted with one to three halogens), or halo;

$R^5$ is hydrogen, or halo;

$R^6$ is hydroxy, —($C_1$-$C_4$)alkyl(optionally substituted with one to three halogens), —($C_1$-$C_4$)alkoxy(optionally substituted with one to three halogens), halo, cyano, $Ar^2$, $Het^1$, $Het^2$, $Ar^2$—($C_1$-$C_4$)alkyl, $Het^2$-($C_1$-$C_4$)alkyl, —C(O)—($C_1$-$C_4$)alkyl, —C(O)—$Ar^2$, —C(O)—$Het^2$, —($C_1$-$C_4$)alkyl-N($R^{13}$)($R^{14}$), —O—($C_1$-$C_4$)alkyl-$Ar^2$, —O—($C_1$-$C_4$)alkyl-C(O)OH, or —O—($C_1$-$C_4$)alkyl-N($R^{13}$)($R^{14}$); wherein $R^{13}$ and $R^{14}$ are each independently hydrogen or —($C_1$-$C_4$)alkyl, or $R^{13}$ and $R^{14}$ taken together with the nitrogen to which they are attached form piperidinyl or pyrrolidinyl;

$Ar^1$ is phenyl;

$Ar^2$ is $Ar^1$ optionally substituted with from one to three moieties independently selected from halo, hydroxy, cyano, —($C_1$-$C_4$)alkyl(optionally substituted with one to three halogens), —C(O)OH, —C(O)$OCH_3$, —($C_1$-$C_4$)alkyl-C(O)OH, —O—($C_1$-$C_4$)alkyl-C(O)OH, —($C_1$-$C_4$)alkyl-N($R^{15}$)($R^{16}$), —O—($C_1$-$C_4$)alkyl-N($R^{15}$)($R^{16}$); wherein $R^{15}$ and $R^{16}$ are each independently hydrogen or —($C_1$-$C_4$)alkyl, or $R^{15}$ and $R^{16}$ taken together with the nitrogen to which they are attached form piperidinyl or pyrrolidinyl;

$Het^1$ is a heterocyclic radical selected from pyridinyl, piperidinyl, pyrimidinyl, pyrazinyl, piperazinyl, pyridazinyl, indolyl, isoindolyl, indolinyl, furanyl, thiazolyl, oxazolyl, isoxazolyl, isothiazolyl, thiophenyl;

$Het^2$ is $Het^1$ optionally substituted with from one to three moieties independently selected from halo, hydroxy, cyano, —($C_1$-$C_4$)alkyl(optionally substituted with one to three halogens), —C(O)OH, —C(O)$OCH_3$, —($C_1$-$C_4$)alkyl-C(O)OH, —O—($C_1$-$C_4$)alkyl)C(O)OH, —($C_1$-$C_4$)alkyl-N($R^{17}$)($R^{18}$), —O—($C_1$-$C_4$)alkyl-N($R^{17}$)($R^{18}$); wherein $R^{17}$ and $R^{18}$ are each independently hydrogen or —($C_1$-$C_4$)alkyl, or $R^{17}$ and $R^{18}$ taken together with the nitrogen to which they are attached form piperidinyl or pyrrolidinyl;

$R^{19}$ is hydroxy, —($C_1$-$C_4$)alkyl(optionally substituted with one to three halogens), or —$CH_2OH$; and $R^{20}$ is Hydrogen, hydroxy, —($C_1$-$C_4$)alkyl(optionally substituted with one to three halogens), or —$CH_2OH$.

In another preferred embodiment the present invention provides a compound structurally represented by formula I, or a pharmaceutically acceptable salt thereof, wherein $G^1$ is methylene; L is methylene;

$R^0$ is

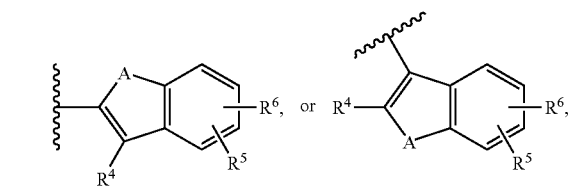

wherein the zig-zag mark represents the point of attachment to the $R^0$ position in Formula I;

$R^1$ is hydrogen;

$R^2$ is

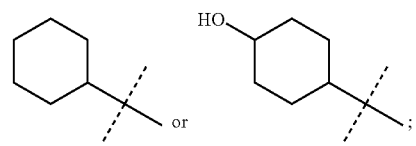

wherein the dashed line represents the point of attachment to the $R^2$ position in formula I; $R^3$ is hydrogen; A is —S— or —O—; $R^4$ is hydrogen; $R^5$ is halo; and $R^6$ is hydrogen.

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably $R^0$ is

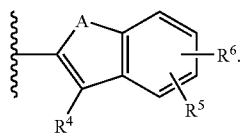

Preferably $R^0$ is

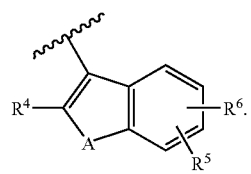

Preferably $G^1$ is methylene. Preferably $G^1$ is ethylene. Preferably L is —CH$_2$—. Preferably A is —CH$_2$—. Preferably A is —S—. Preferably A is —O—. Preferably A is —NH—. Preferably $R^1$ is hydrogen. Preferably $R^1$ is —CH$_3$.

Preferably $R^2$ is

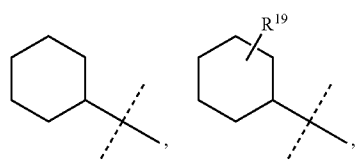

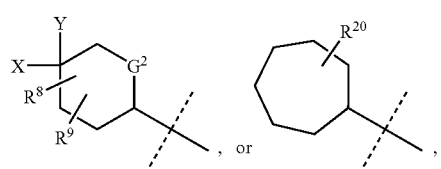

wherein the dashed line indicates the point of attachment to the $R^2$ position in formula I; $G^2$ is methylene, ethylene, or 1-propylene; X is hydrogen, hydroxyl, or —CH$_2$OH; Y is hydrogen or methyl, provided that at least one of X and Y is not hydrogen; or X and Y together with the carbon to which they are attached form a carbonyl; $R^8$ and $R^9$ are each independently hydrogen, hydroxy, or —(C$_1$-C$_4$)alkyl(optionally substituted with one to three halogens).

Preferably $R^2$ is

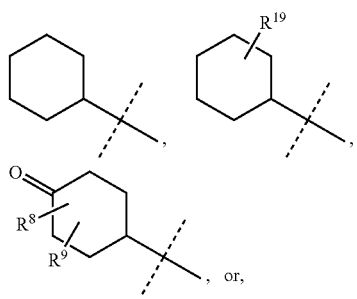

wherein the dashed line indicates the point of attachment to the $R^2$ position in formula I; $R^8$ and $R^9$ are each independently hydrogen, hydroxy, or —(C$_1$-C$_4$)alkyl(optionally substituted with one to three halogens).

Preferably $R^2$ is

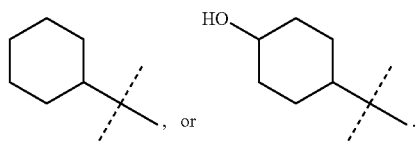

Preferably $R^2$ is

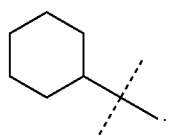

Preferably $R^2$ is

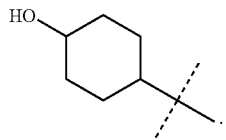

Preferably $R^2$ is

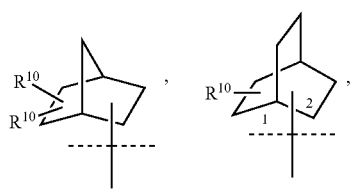

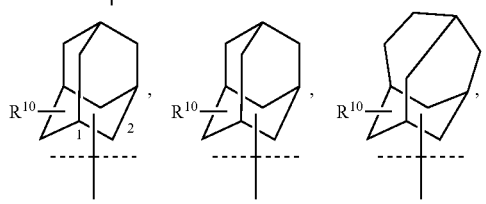

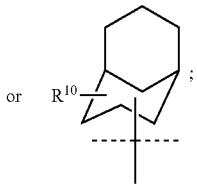

wherein the dashed line indicates the point of attachment to the $R^2$ position in formula I; $R^{10}$ is hydrogen, hydroxy, or —($C_1$-$C_4$)alkyl(optionally substituted with one to three halogens).

Preferably $R^2$ is

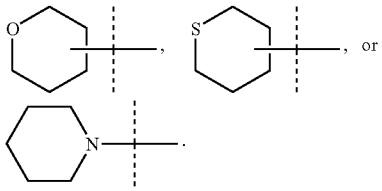

Preferably $R^3$ is hydrogen.

Preferably $R^4$ is hydrogen, hydroxy, —($C_1$-$C_4$)alkyl(optionally substituted with one to three halogens), —($C_1$-$C_4$) alkoxy, halo, cyano, —$SCF_3$, —$OCF_3$. Preferably $R^4$ is hydrogen, or halo. Preferably $R^4$ is halo. Preferably $R^4$ is fluoro or chloro, or bromo.

Preferably $R^5$ is hydroxy, —($C_1$-$C_4$)alkyl(optionally substituted with one to three halogens), —($C_1$-$C_4$)alkoxy(optionally substituted with one to three halogens), halo, cyano, —$SCF_3$, —$OCF_3$, —($C_1$-$C_4$)alkyl-C(O)OH, —($C_1$-$C_4$)alkyl-C(O)O—($C_1$-$C_4$)alkyl, —($C_1$-$C_4$)alkyl-OH, or —($C_1$-$C_4$)alkyl-C(O)N($R^{11}$)($R^{12}$); wherein $R^{11}$ and $R^{12}$ are each independently hydrogen or —($C_1$-$C_4$)alkyl, or $R^{11}$ and $R^{12}$ taken together with the nitrogen to which they are attached form piperidinyl or pyrrolidinyl.

Preferably $R^5$ is hydrogen, hydroxy, —($C_1$-$C_4$)alkyl(optionally substituted with one to three halogens), —($C_1$-$C_4$)alkoxy(optionally substituted with one to three halogens), halo, cyano, —$SCF_3$, —$OCF_3$. Preferably $R^5$ is hydrogen, —$CH_3$ (optionally substituted with one to three halogens), or halo. Preferably $R^5$ is hydrogen.

Preferably $R^6$ is hydroxy, —($C_1$-$C_4$)alkyl(optionally substituted with one to three halogens), —($C_1$-$C_4$)alkoxy(optionally substituted with one to three halogens), halo, cyano, $Ar^2$, $Het^1$, $Het^2$, $Ar^2$—($C_1$-$C_4$)alkyl, $Het^2$—($C_1$-$C_4$)alkyl, —C(O)—($C_1$-$C_4$)alkyl, —C(O)—$Ar^2$, —C(O)—$Het^2$, —($C_1$-$C_4$)alkyl-N($R^{13}$)($R^{14}$), —O—($C_1$-$C_4$)alkyl-$Ar^2$, —O—($C_1$-$C_4$)alkyl-C(O)OH, or —O—($C_1$-$C_4$)alkyl-N($R^{13}$)($R^{14}$); wherein $R^{13}$ and $R^{14}$ are each independently hydrogen or —($C_1$-$C_4$)alkyl, or $R^{13}$ and $R^{14}$ taken together with the nitrogen to which they are attached form piperidinyl or pyrrolidinyl.

Preferably $R^6$ is hydrogen, hydroxy, —($C_1$-$C_4$)alkyl(optionally substituted with one to three halogens), —($C_1$-$C_4$) alkoxy(optionally substituted with one to three halogens), halo, cyano, —C(O)—($C_1$-$C_4$)alkyl, —($C_1$-$C_4$)alkyl-N($R^{13}$) ($R^{14}$), —O—($C_1$-$C_4$)alkyl-C(O)OH, or —O—($C_1$-$C_4$)alkyl-N($R^{13}$)($R^{14}$); wherein $R^{13}$ and $R^{14}$ are each independently hydrogen or —($C_1$-$C_4$)alkyl, or $R^{13}$ and $R^{14}$ taken together with the nitrogen to which they are attached form piperidinyl or pyrrolidinyl.

Preferably $R^6$ is hydroxy, —($C_1$-$C_4$)alkyl(optionally substituted with one to three halogens), —($C_1$-$C_4$)alkoxy(optionally substituted with one to three halogens), halo, cyano, —C(O)—($C_1$-$C_4$)alkyl, —($C_1$-$C_4$)alkyl-N($R^{13}$)($R^{14}$), —O—($C_1$-$C_4$)alkyl-C(O)OH, or —O—($C_1$-$C_4$)alkyl-N ($R^{13}$)($R^{14}$); wherein $R^{13}$ and $R^{14}$ are each independently hydrogen or —($C_1$-$C_4$)alkyl, or $R^{13}$ and $R^{14}$ taken together with the nitrogen to which they are attached form piperidinyl or pyrrolidinyl.

Preferably $R^6$ is $Ar^2$, $Het^1$, $Het^2$, $Ar^2$—($C_1$-$C_4$)alkyl, $Het^2$-($C_1$-$C_4$)alkyl, —C(O)—$Ar^2$, —C(O)—$Het^2$, —O—($C_1$-$C_4$) alkyl-$Ar^2$.

Preferably $Ar^1$ is phenyl.

Preferably $Ar^2$ is $Ar^1$ optionally substituted with from one or two moieties independently selected from halo, hydroxy, cyano, —($C_1$-$C_4$)alkyl(optionally substituted with one to three halogens), —C(O)OH, —C(O)$OCH_3$, —($C_1$-$C_4$)alkyl-C(O)OH, —O—($C_1$-$C_4$)alkyl-C(O)OH, —($C_1$-$C_4$)alkyl-N ($R^{15}$)($R^{16}$), —O—($C_1$-$C_4$)alkyl-N($R^{15}$)($R^6$); wherein $R^{15}$ and $R^{16}$ are each independently hydrogen or —($C_1$-$C_4$)alkyl, or $R^{15}$ and $R^{16}$ taken together with the nitrogen to which they are attached form piperidinyl or pyrrolidinyl.

Preferably $Ar^2$ is $Ar^1$ substituted once with a moiety independently selected from halo, hydroxy, cyano, —($C_1$-$C_4$) alkyl(optionally substituted with one to three halogens), —C(O)OH, —C(O)$OCH_3$, —($C_1$-$C_4$)alkyl-C(O)OH, —O—($C_1$-$C_4$)alkyl-C(O)OH, —($C_1$-$C_4$)alkyl-N($R^{15}$)($R^{16}$), —O—($C_1$-$C_4$)alkyl-N($R^{15}$)($R^{16}$); wherein $R^{15}$ and $R^{16}$ are each independently hydrogen or —($C_1$-$C_4$)alkyl, or $R^{15}$ and $R^{16}$ taken together with the nitrogen to which they are attached form piperidinyl or pyrrolidinyl.

Preferably $Het^1$ is a heterocyclic radical selected from pyridinyl, piperidinyl, pyrimidinyl, pyrazinyl, piperazinyl, pyridazinyl, indolyl, isoindolyl, indolinyl, furanyl, thiazolyl, oxazolyl, isoxazolyl, isothiazolyl, thiophenyl. Preferably $Het^1$ is a heterocyclic radical selected from pyridinyl, piperidinyl, pyrimidinyl, pyrazinyl, piperazinyl, pyridazinyl, furanyl, thiazolyl, oxazolyl, isoxazolyl, isothiazolyl, thiophenyl. Preferably $Het^1$ is pyridinyl.

Preferably $Het^2$ is $Het^1$ optionally substituted with from one or two moieties independently selected from halo, hydroxy, cyano, —($C_1$-$C_4$)alkyl(optionally substituted with one to three halogens), —C(O)OH, —C(O)$OCH_3$, —($C_1$-$C_4$) alkyl-C(O)OH, —O—($C_1$-$C_4$)alkyl)C(O)OH, —($C_1$-$C_4$) alkyl-N($R^7$)($R^{15}$), —O—($C_1$-$C_4$)alkyl-N($R^{17}$)($R^{18}$), wherein $R^{17}$ and $R^{18}$ are each independently hydrogen or —($C_1$-$C_4$) alkyl, or $R^{17}$ and $R^{18}$ taken together with the nitrogen to which they are attached form piperidinyl or pyrrolidinyl.

Preferably $Het^2$ is $Het^1$ substituted once by a moiety selected from halo, hydroxy, cyano, —($C_1$-$C_4$)alkyl(optionally substituted with one to three halogens), —C(O)OH, —C(O)$OCH_3$, —($C_1$-$C_4$)alkyl-C(O)OH, —O—($C_1$-$C_4$) alkyl)C(O)OH, —($C_1$-$C_4$)alkyl-N($R^{17}$)($R^{18}$), —O—($C_1$-$C_4$) alkyl-N($R^{17}$)($R^{18}$), wherein $R^{17}$ and $R^{18}$ are each independently hydrogen or —($C_1$-$C_4$)alkyl, or $R^{17}$ and $R^{18}$ taken together with the nitrogen to which they are attached form piperidinyl or pyrrolidinyl.

Preferably $R^{19}$ is hydroxy, or —$CH_3$ (optionally substituted with one to three halogens), or —$CH_2OH$. Preferably $R^{19}$ is hydroxyl. Preferably $R^{19}$ is —$CH_3$ (optionally substituted with one to three halogens). Preferably $R^{19}$ is —$CH_2OH$.

Preferably $R^{20}$ is hydrogen, hydroxy, —($C_1$-$C_4$)alkyl(optionally substituted with one to three halogens), or —$CH_2OH$. Preferably $R^{20}$ is hydrogen or hydroxyl.

In another embodiment the present invention provides a compound structurally represented by formula (IA), or a pharmaceutically acceptable salt thereof:

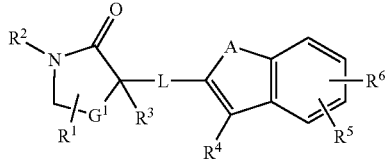

(IA)

wherein $G^1$ is methylene or ethylene;

L is a divalent linking group selected from $C_1$-$C_4$ alkylene, —S—, —CH(OH)—, —O—, or —NH—;

A is methylene, —S—, —O—, or —NH—;

$R^1$ is hydrogen, hydroxy, $C_1$-$C_4$ alkyl, $C_1$-$C_4$ alkoxy, or —$CH_2OR^7$ wherein $R^7$ is hydrogen or $C_1$-$C_4$ alkyl;

$R^2$ is a monovalent radical having one of the following formulae

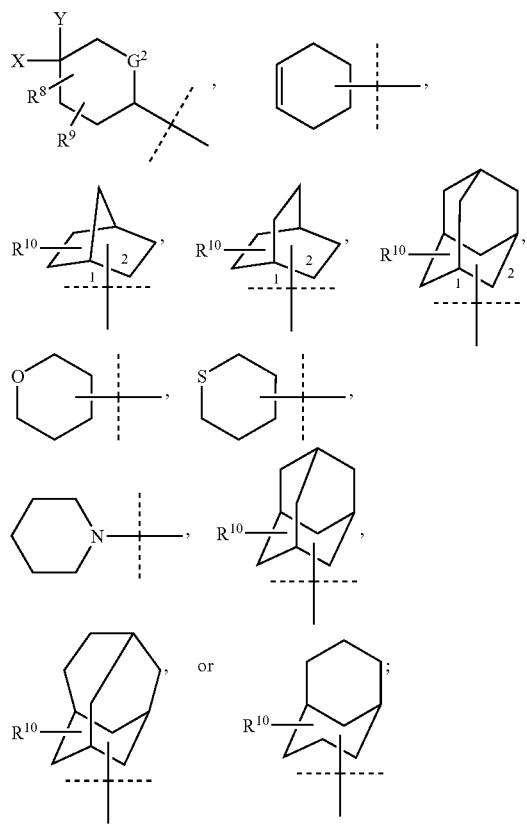

wherein X is hydrogen, hydroxy or —$CH_2OH$ and Y is hydrogen or methyl or X and Y together form (=O) and wherein $R^8$ and $R^9$ are each independently hydrogen, hydroxy, $C_1$-$C_4$ alkyl or phenyl, and $R^{10}$ is hydrogen, hydroxy, or $C_1$-$C_4$ alkyl and $G^2$ is methylene, ethylene, or 1-propylene;

$R^3$ is hydrogen, hydroxy, or $C_1$-$C_4$ alkyl;

$R^4$ and $R^5$ are each independently hydrogen, hydroxy, $C_1$-$C_4$ alkyl, $C_1$-$C_4$ alkoxy, halo, cyano, trifluoromethyl, trifluoromethylsulfanyl, trifluoromethoxy, $Ar^1$, $Het^1$, $Ar^1$—($C_1$-$C_4$ alkyl), $Het^1$-($C_1$-$C_4$ alkyl), —($C_1$-$C_4$ alkyl)COOH, —($C_1$-$C_4$ alkyl)COO($C_1$-$C_4$ alkyl), —($C_1$-$C_4$ alkyl)OH, or —($C_1$-$C_4$ alkyl)CON($R^{11}$)($R^{12}$); wherein $R^{11}$ and $R^{12}$ are each independently hydrogen or $C_1$-$C_4$ alkyl or $R^{11}$ and $R^{12}$ taken together with the nitrogen to which they are attached form piperidinyl or pyrrolidinyl;

$R^6$ is hydrogen, hydroxy, $C_1$-$C_4$ alkyl, $C_1$-$C_4$ alkoxy, halo, cyano, trifluoromethyl, $Ar^2$, $Het^2$, $Ar^2$—($C_1$-$C_4$ alkyl), $Het^2$-($C_1$-$C_4$ alkyl), —CO($C_1$-$C_4$ alkyl), —CO—$Ar^2$, —CO-$Het^2$, —($C_1$-$C_4$ alkyl)N($R^{13}$)($R^{14}$), —O($C_1$-$C_4$ alkyl)-$Ar^2$, —O($C_1$-$C_4$ alkyl)COOH, or —O($C_1$-$C_4$ alkyl)N($R^{13}$)($R^{14}$);
wherein $R^{13}$ and $R^{14}$ are each independently hydrogen or $C_1$-$C_4$ alkyl or $R^{13}$ and $R^{14}$ taken together with the nitrogen to which they are attached form piperidinyl or pyrrolidinyl;

or $R^5$ and $R^6$ combine together on the ring which they are attached to form

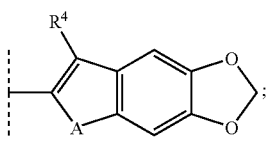

$Ar^1$ is phenyl or naphthyl;

$Ar^2$ is $Ar^1$ optionally substituted with from one to three moieties selected from halo, hydroxy, cyano, trifluoromethyl, $C_1$-$C_4$ alkyl, —COOH, —COOCH$_3$, —($C_1$-$C_4$ alkyl)COOH, —O($C_1$-$C_4$ alkyl)COOH, —($C_1$-$C_4$ alkyl)N($R^{15}$)($R^{16}$), —O($C_1$-$C_4$ alkyl)N($R^{15}$)($R^{16}$), imidazolyl, pyridyl, or —($C_1$-$C_4$ alkyl)-imidazolyl; wherein $R^{15}$ and $R^{16}$ are each independently hydrogen or $C_1$-$C_4$ alkyl or $R^{15}$ and $R^{16}$ taken together with the nitrogen to which they are attached form piperidinyl or pyrrolidinyl;

$Het^1$ is a heterocyclic radical selected from pyridinyl, piperidinyl, pyrimidinyl, pyrazinyl, piperazinyl, pyridazinyl, indolyl, isoindolyl, indolinyl, furanyl, benzofuranyl, thiazolyl, oxazolyl, isoxazolyl, isothiazolyl, benzothiophenyl, thiophenyl, quinolinyl, isoquinolinyl, quinoxalinyl, quinazolinyl, or phthalazinyl; and $Het^2$ is $Het^1$ optionally substituted with from one to three moieties selected from halo, hydroxy, cyano, trifluoromethyl, $C_1$-$C_4$ alkyl, —COOH, —COOCH$_3$, —($C_1$-$C_4$ alkyl)COOH, —O($C_1$-$C_4$ alkyl)COOH, —($C_1$-$C_4$ alkyl)N($R^{17}$)($R^{18}$), —O($C_1$-$C_4$ alkyl)N($R^{17}$)($R^{18}$), imidazolyl, pyridyl, or —($C_1$-$C_4$ alkyl)-imidazolyl; wherein $R^{17}$ and $R^{18}$ are each independently hydrogen or $C_1$-$C_4$ alkyl or $R^{17}$ and $R^{18}$ taken together with the nitrogen to which they are attached form piperidinyl or pyrrolidinyl.

In another embodiment the present invention provides a compound structurally represented by formula (IB), or a pharmaceutically acceptable salt thereof:

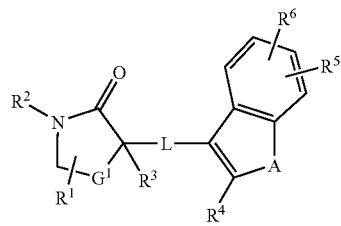

(IB)

wherein

G¹ is methylene or ethylene;

L is a divalent linking group selected from $C_1$-$C_4$ alkylene, —S—, —CH(OH)—, —O—, or —NH—;

A is methylene, —S—, —O—, or —NH—;

R¹ is hydrogen, hydroxy, $C_1$-$C_4$ alkyl, $C_1$-$C_4$ alkoxy, or —CH$_2$OR⁷ wherein R⁷ is hydrogen or $C_1$-$C_4$ alkyl;

R² is a monovalent radical having one of the following formulae

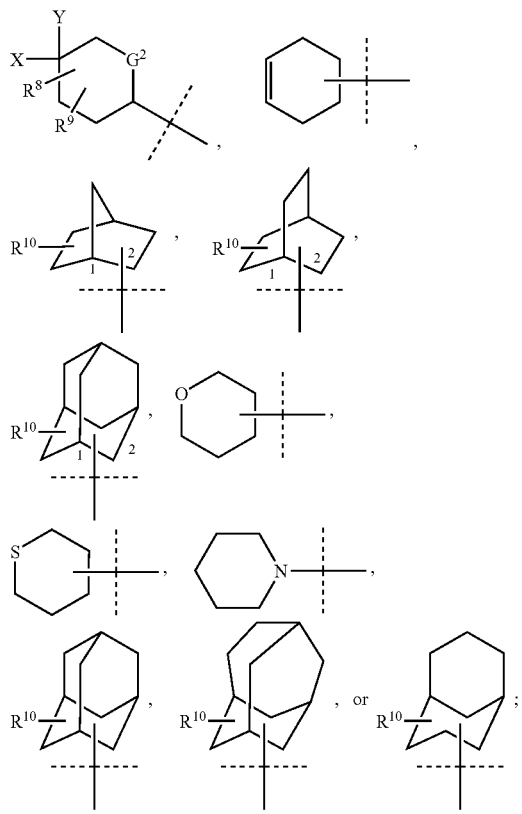

wherein X is hydrogen, hydroxy or —CH$_2$OH and Y is hydrogen or methyl or X and Y together form (=O) and wherein R⁸ and R⁹ are each independently hydrogen, hydroxy, $C_1$-$C_4$ alkyl or phenyl, and R¹⁰ is hydrogen, hydroxy, or $C_1$-$C_4$ alkyl and G² is methylene, ethylene, or 1-propylene;

R³ is hydrogen, hydroxy, or $C_1$-$C_4$ alkyl;

R⁴ and R⁵ are each independently hydrogen, hydroxy, $C_1$-$C_4$ alkyl, $C_1$-$C_4$ alkoxy, halo, cyano, trifluoromethyl, trifluoromethylsulfanyl, trifluoromethoxy, Ar¹, Het¹, Ar¹—($C_1$-$C_4$ alkyl), Het¹-($C_1$-$C_4$ alkyl), —($C_1$-$C_4$ alkyl)COOH, —($C_1$-$C_4$ alkyl)COO($C_1$-$C_4$ alkyl), —($C_1$-$C_4$ alkyl)OH, or —($C_1$-$C_4$ alkyl)CON(R¹¹)(R¹²); wherein R¹¹ and R¹² are each independently hydrogen or $C_1$-$C_4$ alkyl or R¹¹ and R¹² taken together with the nitrogen to which they are attached form piperidinyl or pyrrolidinyl;

R⁶ is hydrogen, hydroxy, $C_1$-$C_4$ alkyl, $C_1$-$C_4$ alkoxy, halo, cyano, trifluoromethyl, Ar², Het², Ar²—($C_1$-$C_4$ alkyl), Het²-($C_1$-$C_4$ alkyl), —CO($C_1$-$C_4$ alkyl), —CO—Ar², —CO-Het², —($C_1$-$C_4$ alkyl)N(R¹³)(R¹⁴), —O($C_1$-$C_4$ alkyl)-Ar², —O($C_1$-$C_4$ alkyl)COOH, or —O($C_1$-$C_4$ alkyl)N(R¹³)(R¹⁴); wherein R¹³ and R¹⁴ are each independently hydrogen or $C_1$-$C_4$ alkyl or R¹³ and R¹⁴ taken together with the nitrogen to which they are attached form piperidinyl or pyrrolidinyl;

or R⁵ and R⁶ combine together on the ring which they are attached form

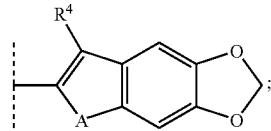

Ar¹ is phenyl or naphthyl;

Ar² is Ar¹ optionally substituted with from one to three moieties selected from halo, hydroxy, cyano, trifluoromethyl, $C_1$-$C_4$ alkyl, —COOH, —COOCH$_3$, —($C_1$-$C_4$ alkyl)COOH, —O($C_1$-$C_4$ alkyl)COOH, —($C_1$-$C_4$ alkyl)N(R¹⁵)(R¹⁶), —O($C_1$-$C_4$ alkyl)N(R¹⁵)(R¹⁶), imidazolyl, pyridyl, or —($C_1$-$C_4$ alkyl)-imidazolyl; wherein R¹⁵ and R¹⁶ are each independently hydrogen or $C_1$-$C_4$ alkyl or R¹⁵ and R¹⁶ taken together with the nitrogen to which they are attached form piperidinyl or pyrrolidinyl;

Het¹ is a heterocyclic radical selected from pyridinyl, piperidinyl, pyrimidinyl, pyrazinyl, piperazinyl, pyridazinyl, indolyl, isoindolyl, indolinyl, furanyl, benzofuranyl, thiazolyl, oxazolyl, isoxazolyl, isothiazolyl, benzothiophenyl, thiophenyl, quinolinyl, isoquinolinyl, quinoxalinyl, quinazolinyl, or phthalazinyl; and Het² is Het¹ optionally substituted with from one to three moieties selected from halo, hydroxy, cyano, trifluoromethyl, $C_1$-$C_4$ alkyl, —COOH, —COOCH$_3$, —($C_1$-$C_4$ alkyl)COOH, —O($C_1$-$C_4$ alkyl)COOH, —($C_1$-$C_4$ alkyl)N(R¹⁷)(R¹⁸), —O($C_1$-$C_4$ alkyl)N(R⁷)(R¹⁸), imidazolyl, pyridyl, or —($C_1$-$C_4$ alkyl)-imidazolyl; wherein R¹⁷ and R¹⁸ are each independently hydrogen or $C_1$-$C_4$ alkyl or R¹⁷ and R¹⁸ taken together with the nitrogen to which they are attached form piperidinyl or pyrrolidinyl.

Preferred compounds of the invention include compounds or pharmaceutically acceptable salts of formulae (IA) or (IB) wherein:

(1) G¹ is methylene;

(2) L is methylene;

(3) R¹ is hydrogen or methyl;

(4) R² is cyclohexyl, 6-hydroxycyclohexyl, or 1-adamantyl;

(5) R³ is hydrogen;

(6) A is —S— or —O—;

(7) R⁴ and R⁵ are each independently hydrogen, hydroxy, $C_1$-$C_4$ alkyl, $C_1$-$C_4$ alkoxy, halo, cyano, or trifluoromethyl;

(8) R⁶ is hydrogen, hydroxy, $C_1$-$C_4$ alkyl, $C_1$-$C_4$ alkoxy, halo, cyano, or trifluoromethyl;

(9) R⁵ and R⁶ combine together on the ring which they are attached to form

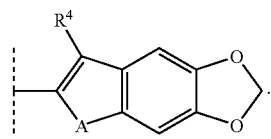

Further, any combination of the above groups, e.g., (1) and (2); (3) and (5); (3), (4), (5), (6), (7), and (8); and (1), (2), (3), (4), (5), (6), (7), and (8), are specifically contemplated.

Preferred compounds of the invention also include compounds or pharmaceutically acceptable salts of formula (IIA):

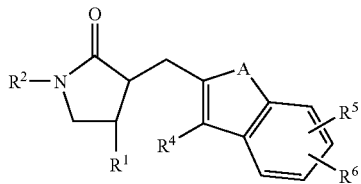

(IIA)

wherein
R$^1$ is hydrogen or methyl;
R$^2$ is a monovalent radical having one of the following formulae

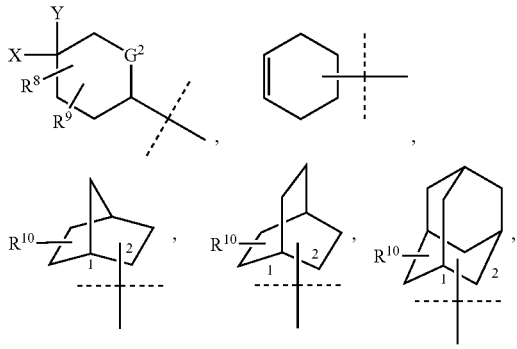

wherein X is hydrogen, hydroxy or —CH$_2$OH and Y is hydrogen or methyl or X and Y together form (=O) and wherein R$^8$ and R$^9$ are each independently hydrogen, hydroxy, C$_1$-C$_4$ alkyl or phenyl, and R$^{10}$ is hydrogen, hydroxy, or C$_1$-C$_4$ alkyl and G$^2$ is methylene, ethylene, or 1-propylene;
A is methylene, —S—, —O—, or —NH—;
R$^4$ and R$^5$ are each independently hydrogen, hydroxy, C$_1$-C$_4$ alkyl, C$_1$-C$_4$ alkoxy, halo, cyano, or trifluoromethyl; and
R$^6$ is hydrogen, hydroxy, C$_1$-C$_4$ alkyl, C$_1$-C$_4$ alkoxy, halo, cyano, or trifluoromethyl.

Preferred compounds of the invention also include compounds or pharmaceutically acceptable salts of formula (IB):

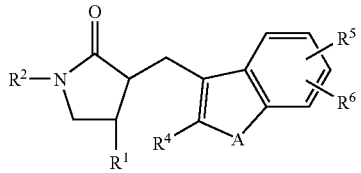

(IIB)

wherein
R$^1$ is hydrogen or methyl;
R$^2$ is a monovalent radical having one of the following formulae

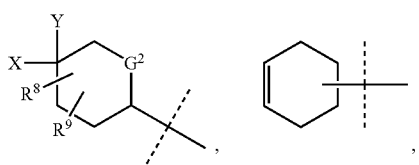

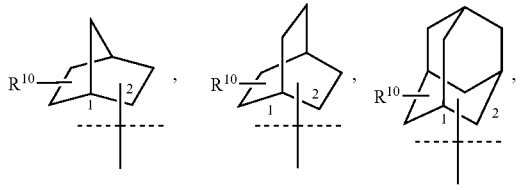

wherein X is hydrogen, hydroxy or —CH$_2$OH and Y is hydrogen or methyl or X and Y together form (=O) and wherein R$^8$ and R$^9$ are each independently hydrogen, hydroxy, C$_1$-C$_4$ alkyl or phenyl, and R$^{10}$ is hydrogen, hydroxy, or C$_1$-C$_4$ alkyl and G$^2$ is methylene, ethylene, or 1-propylene;
A is methylene, —S—, —O—, or —NH—;
R$^4$ and R$^5$ are each independently hydrogen, hydroxy, C$_1$-C$_4$ alkyl, C$_1$-C$_4$ alkoxy, halo, cyano, or trifluoromethyl; and
R$^6$ is hydrogen, hydroxy, C$_1$-C$_4$ alkyl, C$_1$-C$_4$ alkoxy, halo, cyano, or trifluoromethyl.

Other preferred compounds of the invention include compounds or pharmaceutically acceptable salts of formulae (IIA) or (IB) wherein
(1) R$^1$ is hydrogen;
(2) R$^2$ is cyclohexyl or 1-adamantyl;
  (a) (3) A is —O— or —S—;
(4) R$^4$ and R$^5$ are each independently hydrogen, hydroxy, C$_1$-C$_4$ alkyl, C$_1$-C$_4$ alkoxy, halo, cyano, or trifluoromethyl; and
(5) R$^6$ is hydrogen.

Further, any combination of the above groups, e.g., (1) and (2); (3) and (4); (1), (2), (3), and (4); (1), (2), (3), (4) and (5); (1) and (3); (2) and (3), and the like, are specifically contemplated.

Preferred compounds of the invention are represented by the following compounds and pharmaceutically acceptable salts thereof:
3-Benzo[b]thiophen-2-ylmethyl-1-cyclohexyl-pyrrolidin-2-one;
3-(3-Chloro-benzo[b]thiophen-2-ylmethyl)-1-cyclohexyl-pyrrolidin-2-one;
3-Benzofuran-2-ylmethyl-1-cyclohexyl-pyrrolidin-2-one;
3-(7-Chloro-1,3-dioxa-5-thia-s-indacen-6-ylmethyl)-1-cyclohexyl-pyrrolidin-2-one;
1-Cyclohexyl-3-(3-methyl-benzo[b]thiophen-2-ylmethyl)-pyrrolidin-2-one;
3-(3-Chloro-6-fluoro-benzo[b]thiophen-2-ylmethyl)-1-cyclohexyl-pyrrolidin-2-one;
3-(5-Chloro-benzo[b]thiophen-3-ylmethyl)-1-cyclohexyl-pyrrolidin-2-one;
3-(3-Chloro-6-methoxy-benzo[b]thiophen-2-ylmethyl)-1-cyclohexyl-pyrrolidin-2-one;
3-(5-Bromo-benzo[b]thiophen-2-ylmethyl)-1-cyclohexyl-pyrrolidin-2-one;
3-(6-Bromo-benzo[b]thiophen-2-ylmethyl)-1-cyclohexyl-pyrrolidin-2-one;
3-(3-Chloro-benzo[b]thiophen-2-ylmethyl)-1-(cis-4-hydroxy-cyclohexyl)-pyrrolidin-2-one;
3-(3-Chloro-benzo[b]thiophen-2-ylmethyl)-1-(4-hydroxy-cyclohexyl)-pyrrolidin-2-one;
1-(4-Hydroxy-cyclohexyl)-3-(3-methyl-benzofuran-2-ylmethyl)-pyrrolidin-2-one;
3-(3-Chloro-6-hydroxy-benzo[b]thiophen-2-ylmethyl)-1-cyclohexyl-pyrrolidin-2-one;

4-[3-Chloro-2-(1-cyclohexyl-2-oxo-pyrrolidin-3-ylmethyl)-benzo[b]thiophen-6-yloxymethyl]-benzoic acid;
3-[3-Chloro-6-(3-dimethylamino-propoxy)-benzo[b]thiophen-2-ylmethyl]-1-cyclohexyl-pyrrolidin-2-one hydrochloride salt;
3-[3-Chloro-6-(3-dimethylamino-propoxy)-benzo[b]thiophen-2-ylmethyl]-1-cyclohexyl-pyrrolidin-2-one;
4-[3-Chloro-2-(1-cyclohexyl-2-oxo-pyrrolidin-3-ylmethyl)-benzo[b]thiophen-6-yloxy]-butyric acid;
1-Cyclohexyl-3-[5-(2-fluoro-pyridin-4-yl)-benzo[b]thiophen-2-ylmethyl]-pyrrolidin-2-one;
4-[2-(1-Cyclohexyl-2-oxo-pyrrolidin-3-ylmethyl)-benzo[b]thiophen-5-yl]-benzoic acid;
3-(3-Chloro-benzo[b]thiophen-2-ylmethyl)-trans-1-(4-hyroxyl-cyclohexyl)-piperidin-2-one;
3-(3-Chloro-benzo[b]thiophen-2-ylmethyl)-1-(4-hyroxyl-cyclohexyl)-piperidin-2-one; and
3-(3-Chloro-benzo[b]thiophen-2-ylmethyl)-cis-1-(4-hyroxyl-cyclohexyl)-piperidin-2-one.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius.

"TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates [M+H] unless indicated otherwise. "MS (FD)" refers to field desorption mass spectrometry, "MS(IS)" refers to ion spray mass spectrometry, "Mass spectrum (ion spray)" refers to ion-spray ionization mode. "MS(FIA)" refers to flow injection analysis mass spectrometry, "MS (FAB)" refers to fast atom bombardment mass spectrometry, "MS(EI)" refers to electron impact mass spectrometry, "MS(ES)" refers to electron spray mass spectrometry, "MS (EI)" refers to electron impact mass spectrometry-electrospray ionization, "MS (ES+)" refers to mass spectrometry-electrospray ionization, "MS (APCi) refers to atmospheric pressure chemical ionization mass spectrometry, "UV" refers to ultraviolet spectrometry, "$^1$H NMR" refers to proton nuclear magnetic resonance spectrometry. "LC-MS" refers to liquid chromatography-mass spectrometry, "GC/MS" refers to gas chromatography/mass spectrometry. "IR" refers to infra red spectrometry, and the absorption maxima listed for the IR spectra are only those of interest and not all of the maxima observed. "RT" refers to room temperature.

"THF" refers to tetrahydrofuran, "LAH" refers to lithium aluminum hydride, "LDA" refers to lithium diisopropylamide, "DMSO" refers to dimethylsulfoxide, "DMF" refers to dimethylformamide, "HCl" refers to hydrochloric acid, "EtOAc" refers to ethyl acetate, "Pd—C" refers to palladium on carbon, "DCM" refers to dichloromethane, "DMAP" refers to dimethylaminopyridine, "LiHMDS" refers to Lithium Hexamethyldisilisane, "TFA" refers to trifluoroacetic acid, "EDAC" refers to N-Ethyl-N'-(3-dimethylaminopropyl)carbodiimide hydrochloride, "HOBT" refers to 1-Hydroxy benzotriazole, "Bn-9-BBN" refers to Benzyl-9-borabicyclo[3.3.1]nonane, "Pd(dppf)Cl$_2$" refers to [1,1'-Bis(diphenylphosphino)-ferrocene)dichloropalladium(II), "EDCI" refers to N-Ethyl-N'-(3-dimethylaminopropyl)carbodiimide hydrochloride, "DBU" refers to 1,8-Diazabicyclo[5.4.0]undecene-7, "TBSCl" refers to tert-butyl-dimethyl-silanyloxymethyl chloride, "NBS" refers to N-Bromosuccinimide, "TsOH" refers to p-toluenesulfonic acid, "DCE" refers to dichloroethane, "DAST" refers to (Diethylamino)sulfur trifluoride, "EA/H" refers to ethyl acetate/hexanes mixture, "Pd$_2$(dba)$_3$" refers to Bis(dibenzylideneacetone)palladium, "BINAP" refers to 2,2'-Bis(diphenylphospino-1,1'-binaphthalene, "NMP" refers to N-Methylpyrrollidine, "TMSCN" refers to Trimethylsilyl cyanide, "TBAF" refers to Tetrabutylammonium fluoride, "Tf$_2$O" refers to trifluoromethanesulfonic anhydride, "TBSO" refers to tert-butyl-dimethyl-silanyloxy, "OTf" refers to trifluoromethanesulfonate, MeTi(Oi-Pr)$_3$ refers to methyltitanium triisopropoxide. DIAD refers to diisopropyl azodicarboxylate. In a structure, "Ph" refers to phenyl, "Me" refers to methyl, "Et" refers to ethyl, "Bn" refers to benzyl, and "MeOH" refers to methanol.

General Procedures

Compounds of the present invention have been formed as specifically described in the examples. Alternative synthesis methods may also be effective and known to the skilled artisan. Unless otherwise indicated, all variables, such as L, $G^1$, $R^1$ to $R^{20}$, etc., are as defined for analogous variables in the summary of the invention, and otherwise as defined herein.

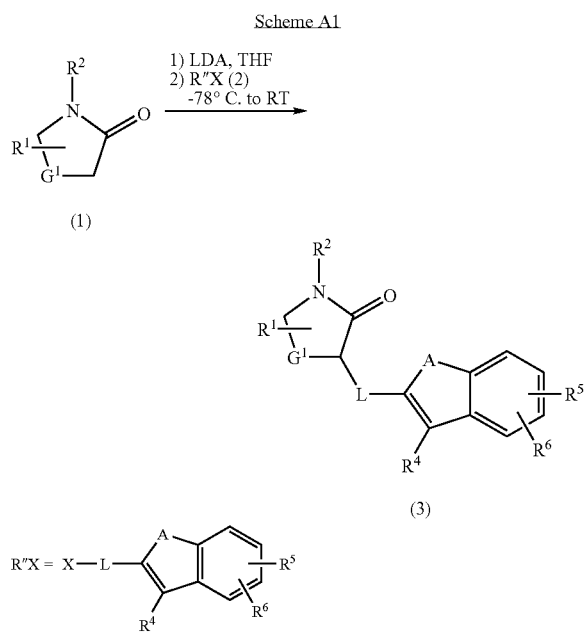

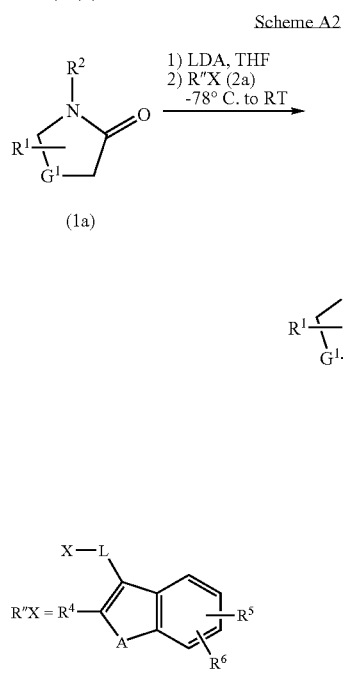

In Schemes A1 and A2 the lactam (1 or 1a) is conjugated with an alkylating agent R"X (2 or 2a) to give (3 or 3a). The reaction is carried out using lithium diisopropylamide (LDA) to form the lithium anion of the lactam but other bases could be used (lithium hexamethyl disilazide, sodium hydride, phosphazenes, potassium tert-butoxide) (Conditions used are a modification of the conditions to alkylate 1-methyl-pyrrolidinone, see: Hullet, P. et al. *Can. J. Chem.* (1976) 54, 1098-1104; For use of phosphazenes in alkylation of lactams, see: Goumri-Magnet et al. *J. Org. Chem.* (1999) 64, 3741-3744). The reaction is carried out in THF but other solvents could be used (i.e.; dichloromethane, ether, toluene, etc. to facilitate solubility of the components). The reaction can be run with either an excess of the lactam and LDA or with an excess of the alkylating agent. The ease of purification of the product from the starting materials and the relative expense of the components and the preference of the chemist lead to different choices of which ratios of starting materials to use. In general the reaction affords good to moderate yields of product especially for benzylic alkylating reagents. The reaction is initiated at temperatures of −78° C. and warmed to room temperature. Depending on the reactivity of the alkylating reagent, the time varies. Alkyl alkylating agents take longer (1-3 hours or more, while the subset of benzyl alkylating agents proceed rapidly at −78° C. (<15 minutes). The alkylating agents are halides; generally the iodides, bromides, or chlorides; however one skilled in the art would recognize that tosylates, triflates, nosylates, and other alkylating agents would work. When $R^1$ is not hydrogen, the major product of the alkylation is the trans-isomer and this is the preferred method for the preparation of these compounds.

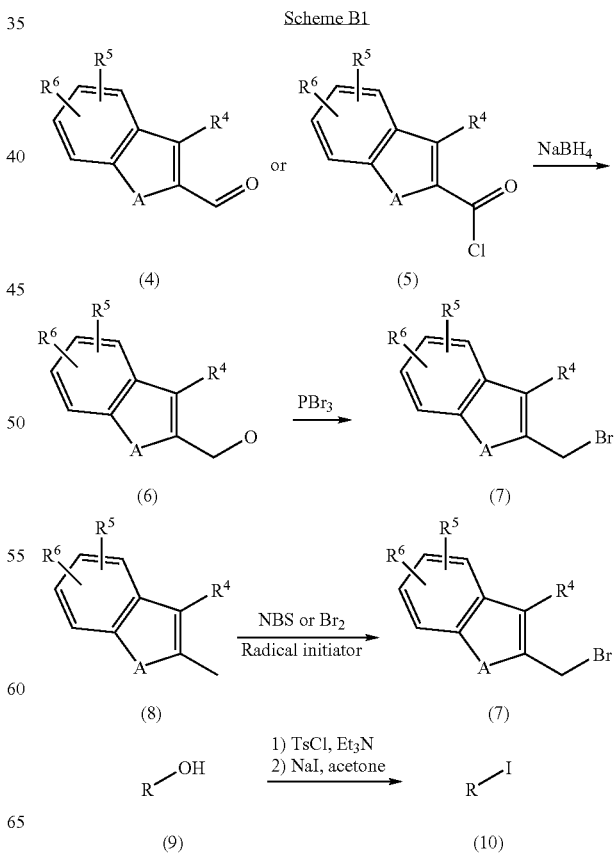

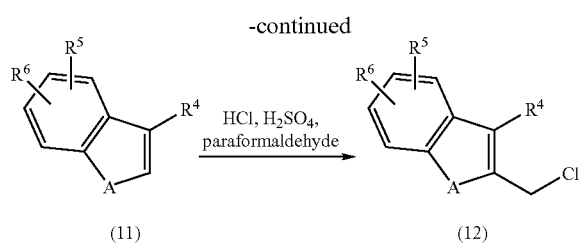

Scheme B2

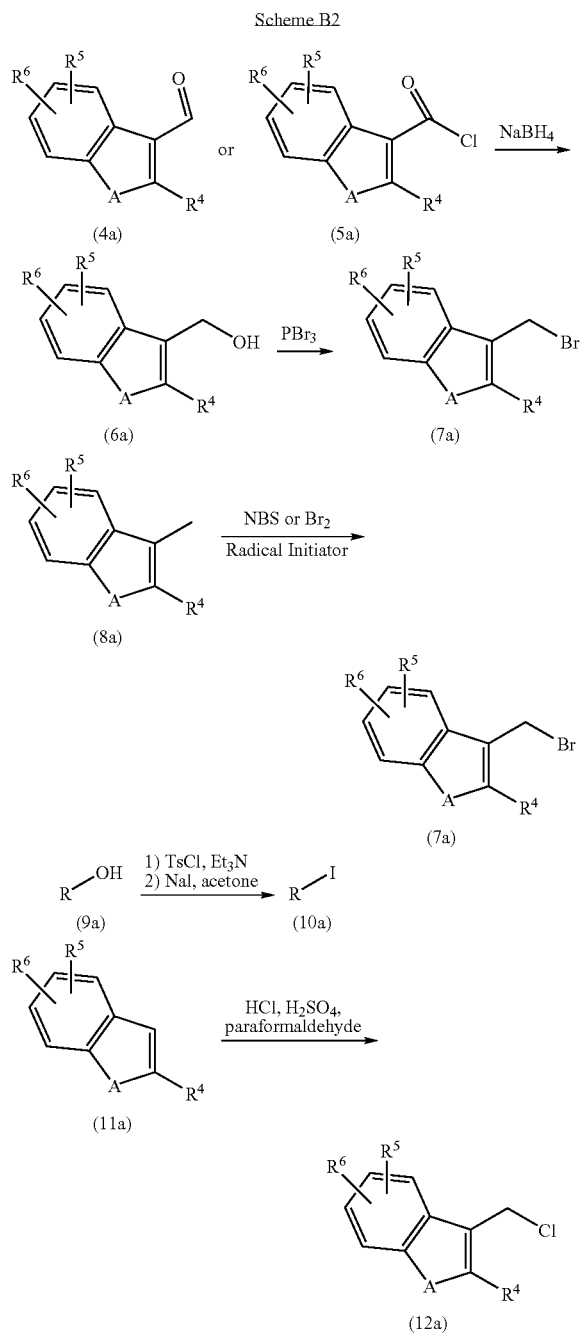

In Schemes B1 and B2 the alkylating agents (7) can be prepared by modifications of a variety of literature conditions a few of which are illustrated here. Substituted aldehydes (4 or 4a) or carbonyl chlorides (5 or 5a), which are readily available from the corresponding carboxylic acids with thionyl chloride or oxalyl chloride, and the subclass of benzo[b]thiophene-3-chloro-2-carbonyl chlorides are readily available from the appropriate cinnamic acid and thionyl chloride (*J. Heterocyclic Chem.* (1986) 1571-1577), are reduced readily by dropwise addition into a mixture of sodium borohydride in ethanol/THF to form the substituted alcohols (6 or 6a). Conversion of the substituted alcohols (6 or 6a) to the bromides (7 or 7a) can generally be achieved by adding a moderate excess of phosphorous tribromide to a solution of the alcohol in a solvent (either ether or dichloromethane; but other solvents compatible with phosphorous tribromide would work). Other literature procedures can effect the conversion of (6 or 6a) to (7 or 7a); i.e.; treatment with HBr in AcOH with some substrates; conversion of the alcohol to a mesylate followed by Br-displacement, or treatment with $CBr_4$ and triphenylphosphine to name but three of many possibilities. The iodides or chlorides can be made by modifications of the above procedures.

In cases where there is but one alkyl moiety attached to the heteroaryl moiety as in (8 or 8a), conversion of the methyl moiety to the halide (7 or 7a) can be effected by treatment with a radical precursor (AIBN, benzyl peroxide, a peroxide, etc.) in a suitable solvent with a bromide radical precursor (NBS, bromine, etc.) to afford the bromide (7 or 7a). Replacement of the bromide radical precursor with a chloride or iodide radical precursor can afford the corresponding chlorides or iodides.

In cases where R is not a halomethyl heteroaromatic moiety, the alkyl iodides are generally the best alkylating agent for the reaction in General Scheme A. A versatile method of preparing these alkylating partners is to first make the tosylate (triflate and mesylate with alternative bases than triethyl amine can also be effectively used) from an alcohol (9) and then displace the tosylate with iodide ion in acetone.

Chloromethyl-heteroaromatics in certain cases can be easily made from paraformaldehyde or freshly cracked formaldehyde or another formaldehyde synthetic equivalent via acid catalyzed aromatic substitution (*J. Med Chem.* (1988) 31, 72-83).

Scheme C1

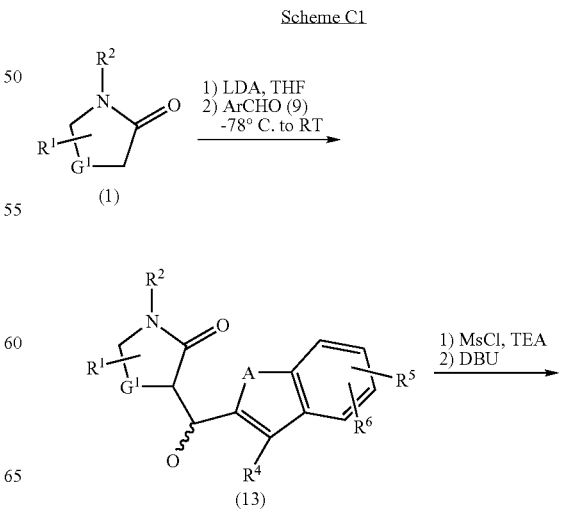

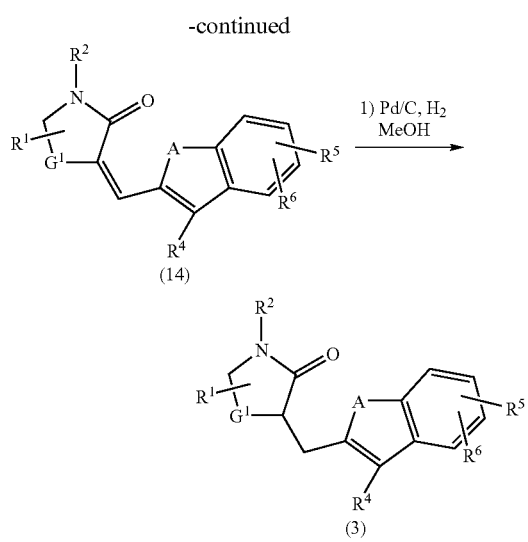

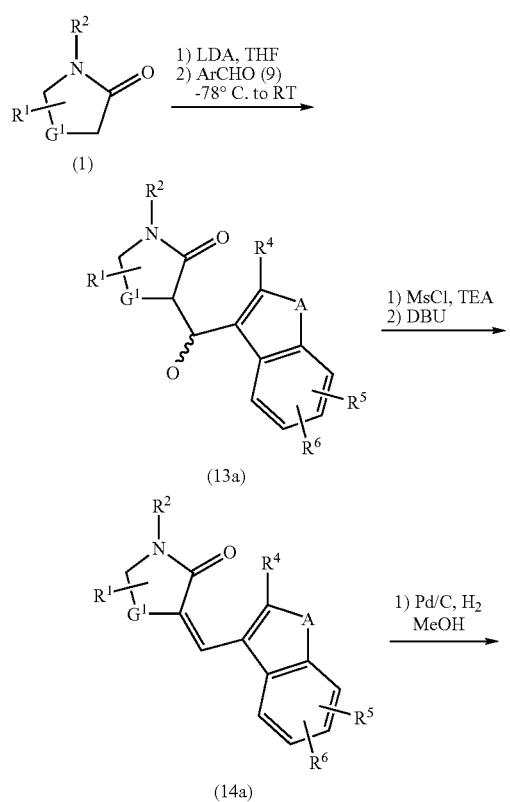

In Schemes C1 and C2, an alternative to using an alkylating agent to prepare (3 or 3a) is described. Substituted lactams (1) can be converted to the alcohols (13 or 13a) (*J. Med. Chem.* (1991) 34, 887-900) by treatment of the lactam with LDA followed by treatment with an aldehyde. Alternatively, these alcohols could be made from carboxylic esters via a Claisen reaction to form an intermediate ketone, followed by a hydride reduction (*Liebigs, Ann. Chemie*. (1983) 165-180). Elimination of the alcohol to the α,β-unsaturated lactam (14 or 14a) can be effected by formation of the mesylate with methanesulfonyl chloride and triethyl amine as base; followed by treatment with DBU (*Chem. Pharm. Bull*. (1990) 38 393-399). Other conditions to affect this transformation (i.e.; different bases to substitute for triethyl amine or DBU or different activation agents to replace DBU) could be used and should be evident to those trained in the art. Reduction of the double bond moiety of (14 or 14a) by catalytic hydrogenation affords (3 or 3a). Catalytic hydrogenation could potentially be replaced with 1,4-conjugate addition of hydride or alkyl metal species to form (3 or 3a) or alkylated variants thereof.

When $R^1$ does not equal hydrogen, the major compound of these reduction is the cis-isomer and this is the preferred method for the preparation of these compounds.

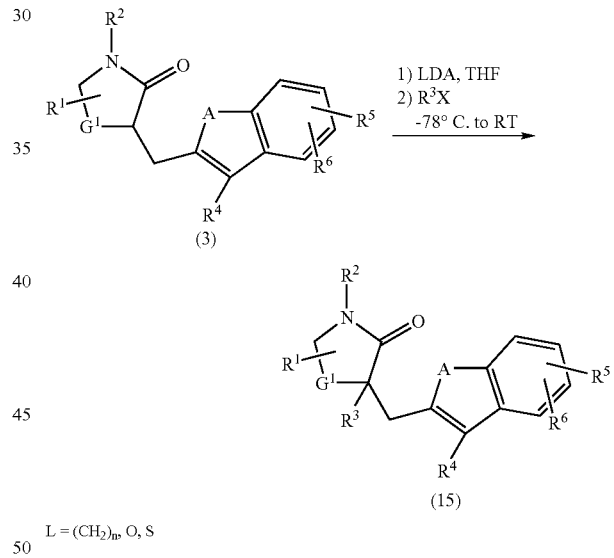

L = $(CH_2)_n$, O, S

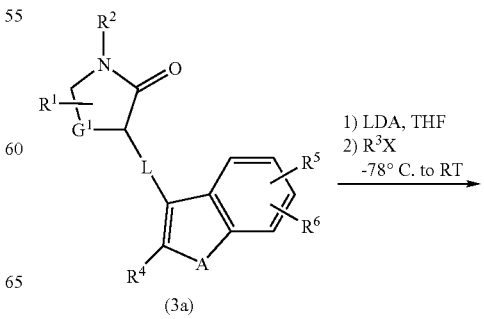

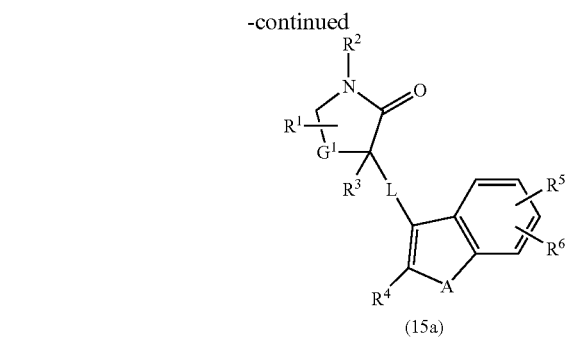

In Scheme D1 and D2 the lactam (3) is conjugated with an alkylating agent (2) to give (15). As in the case of Scheme A, other bases and solvents can be used. When $R^1$ does not equal H, the major product has a trans-relationship between the 3-substitutent on the lactam and $R^1$. It is evident to those trained in the art that both isomers of (15) when $L=(CH_2)_n$ can be preferentially made as the major product by judicious choice of which alkylating agent, $R^3X$ or ArLX, to introduce first.

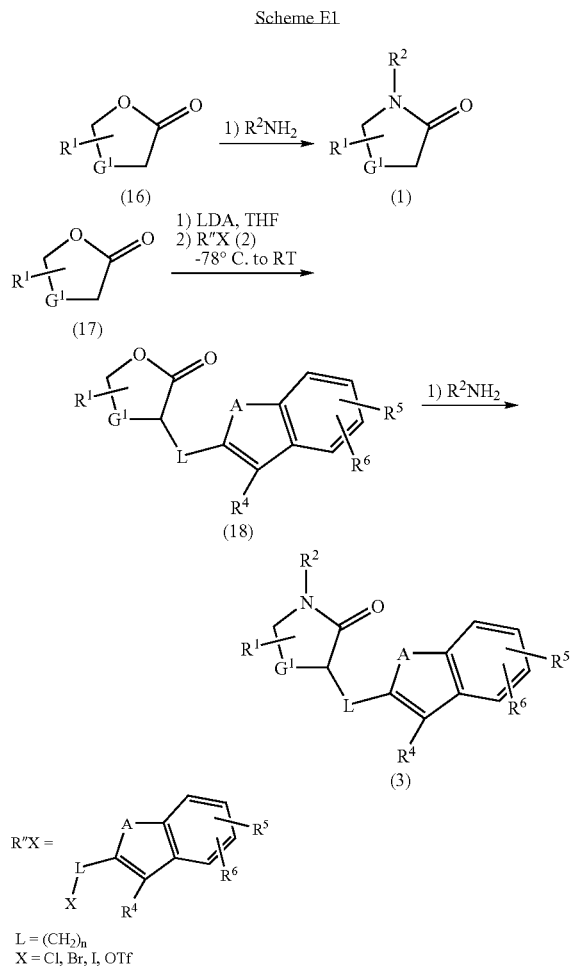

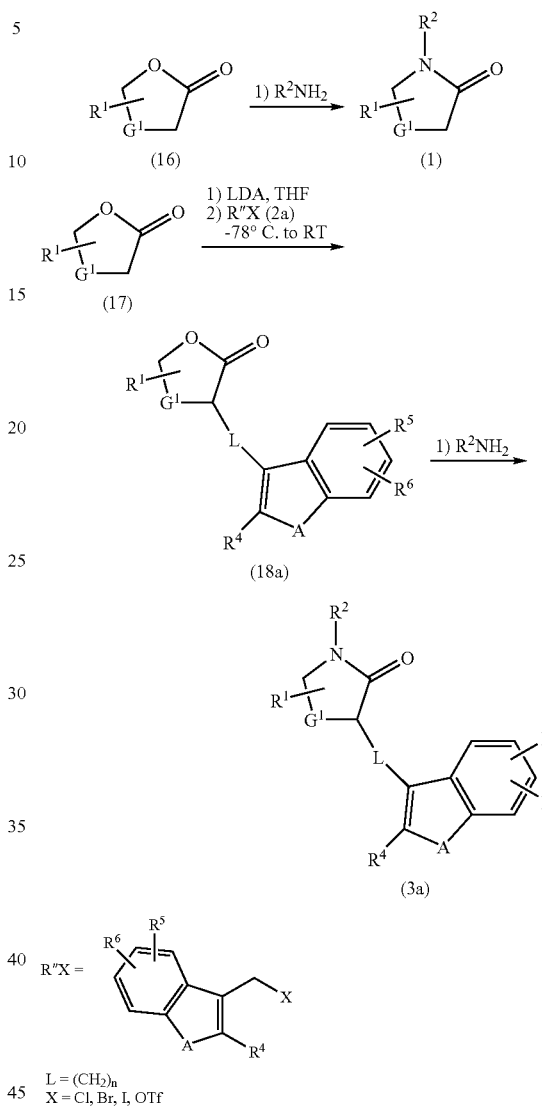

In Scheme $E^1$ and $E^2$ the lactone (16) is reacted with a primary amine to form the lactam starting material (J. Am. Chem. Soc. (1947) 69, 715-716). A large number of primary amines can be utilized in this procedure. Benzyl amines, substituted cycloalkyl amines (substituted with alkyl, amine, alcohols, etc), and fused bi- and tri-cyclic amines (i.e., adamantyl, norborenyl, camphoryl, etc) may be used. The reaction proceeds in two steps and involves a thermal elimination of water at high temperature. No solvent is used; but a high boiling solvent could be added if perceived to be desirable. It should be noted that if $R^3$ is at the 3-position of the lactam, then the product is the same as (3 or 3a) and an alkylation is not necessary. This procedure is done as shown in the second synthetic depiction in Schemes $E^1$ and $E^2$. Alkylation of the lactone (17) with LDA and an alkylating agent using the conditions of Schemes A1 and A2 affords (18 and 18a) and condensation with the amine under thermal conditions without solvent forms (3 and 3a) directly.

Scheme F

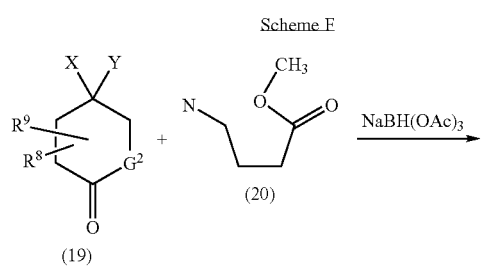

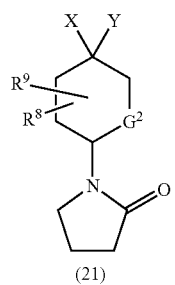

In Scheme F, cyclic ketones (19) are condensed with methyl 4-aminobutyrate hydrochloride (20) in a reductive amination with sodium triacetoxyborohydride to afford the lactams (21) (*Syn Lett.* (1994) 81-83). The reaction is done using a modification of the conditions described by Marynoff et al. The solvent is 1,2-dichloroethane and the reaction takes 1-4 days to complete depending upon the ketone. In some cases, the crude product is heated to reflux in toluene to force the ring closure and drive the reaction to completion. This cyclization can be done with 5-, 6-, and 7-member ring ketones (19); substituted and not, and with ketals (Y and Z connect to form =OCH$_2$CH$_2$O) on the ring to aid in the further preparation of advanced intermediates.

Scheme G1

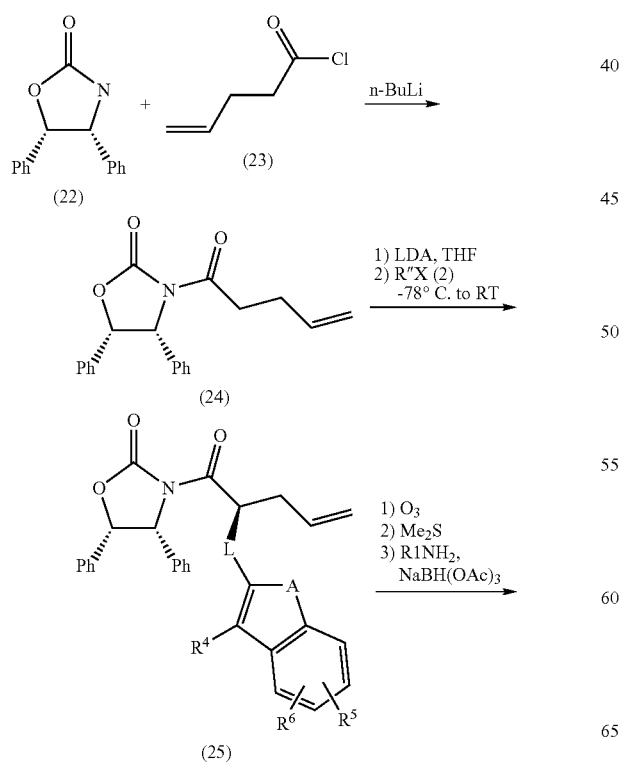

Scheme G2

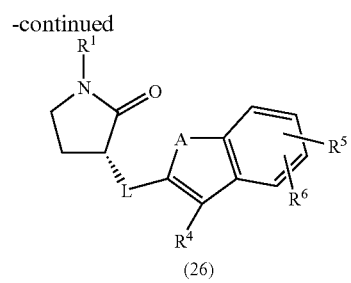

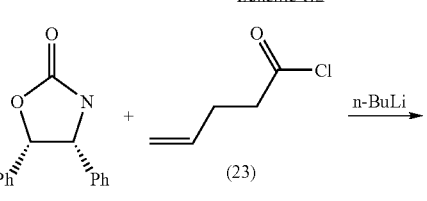

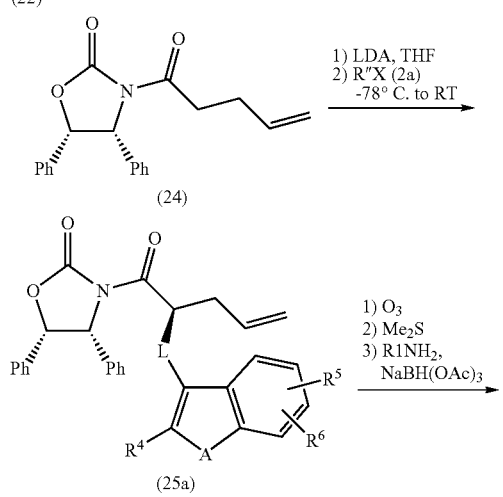

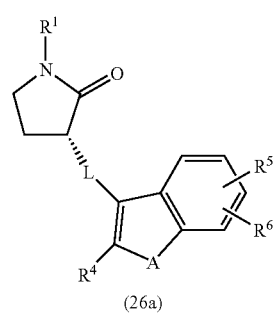

In Scheme G1 and G2, a route to chiral 3-substituted lactams is shown. Acylation of the chiral auxiliary (22) with pent-4-enoyl chloride (acylation with longer unsaturated acyl chlorides would give 6- and higher member ring lactams via analogy) affords the imide (24). Alkylation of the imide (24) using the general alkylation conditions of general Scheme A affords in high diastereomeric excess the drawn diastereomer (25 and 25a). It is probable that other chiral auxiliaries similar to (22) could be utilized with similar or higher diastereomeric excess. Ozonolysis of the olefin affords an aldehyde intermediate that is immediately reductively cyclized with a primary amine in conditions similar to those of Scheme F to afford the lactam (26 and 26a) (*Bioorg. Med. Chem. Lett.* (2003) 2035-2040). Of course, utilization of the other enantiomer of (22) gives the other enantiomer of (26 and 26a) and both enantiomers are claimed.

-continued

Scheme H

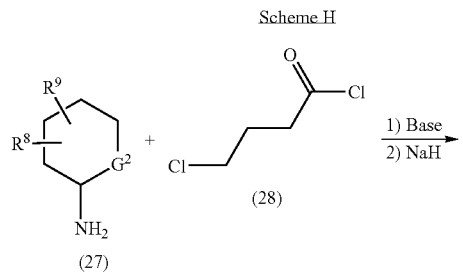

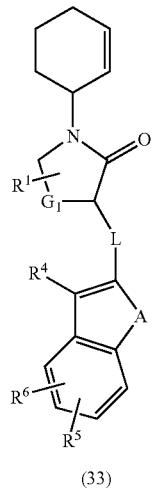

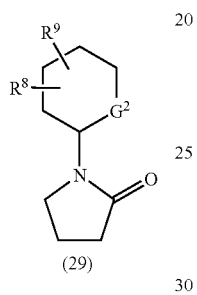

In Scheme H, substituted cyclohexyl amines are acylated with 4-chlorobutyryl chloride using triethylamine, pyridine, or another appropriate acid scavenger base. The second cyclization sometimes occurs in this acylation, but usually a stronger base such as NaH or KH is necessary to effect the second cyclization. Other strong bases such as tert-BuOK could potentially be used. This procedure is particularly effective to make lactams with a 1-alkyl substituent on the cyclic amine moiety.

Scheme I1

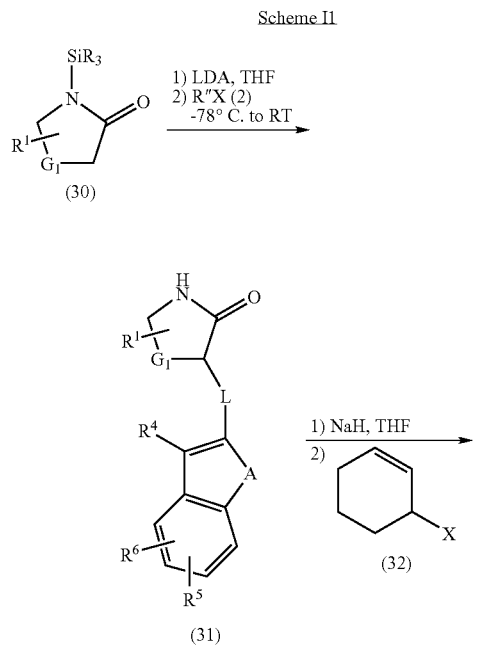

Scheme I2

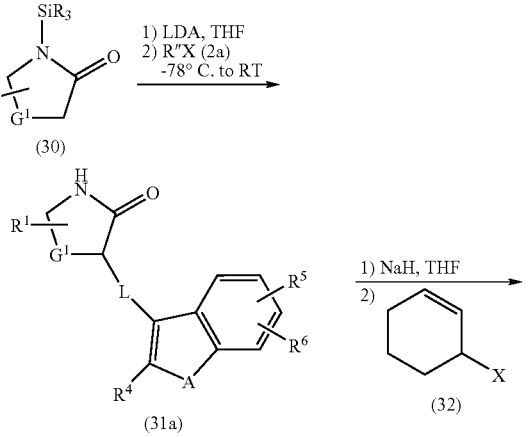

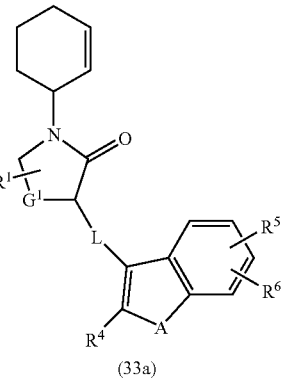

In Schemes I1 and I2, the silylated lactam (30) is alkylated via treatment with LDA, followed by treatment with an alkylating agent (2 or 2a) in conditions similar to Scheme A. The silyl moiety is removed in the aqueous workup of the reaction. The substituted lactam product (31 and 31a) can be N-alkylated by treatment with NaH in THF with a substituted or unsubstituted 3-halo-cyclohex-1-ene to form the lactam (33 or 33a).

Scheme J1
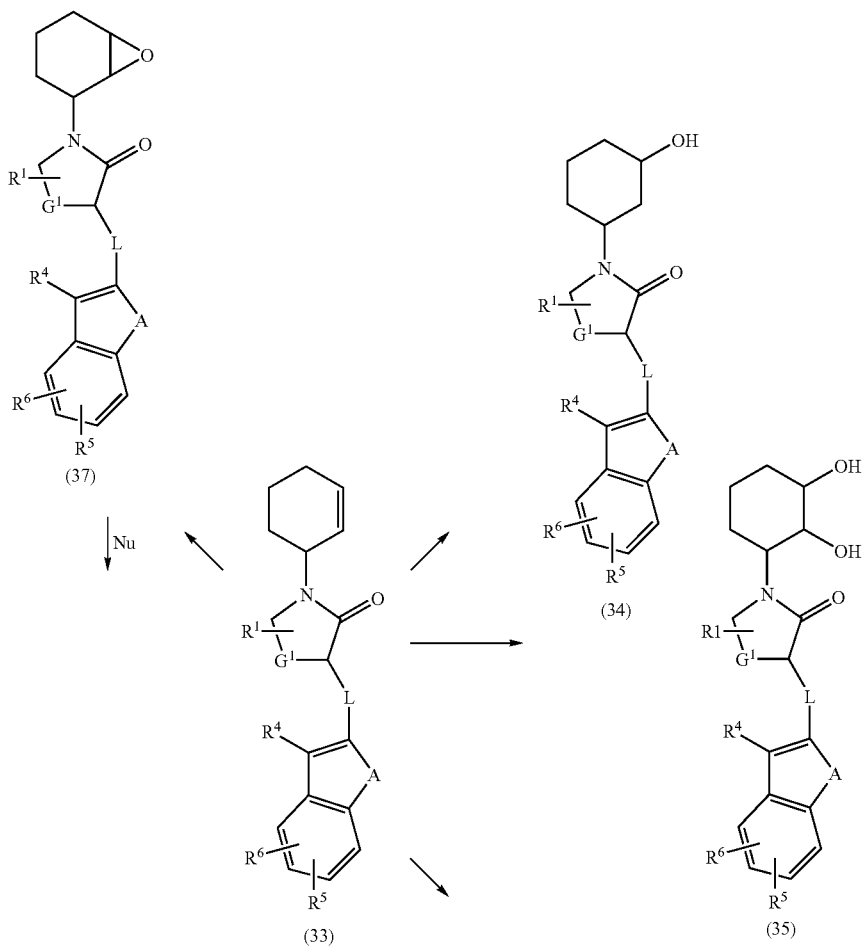
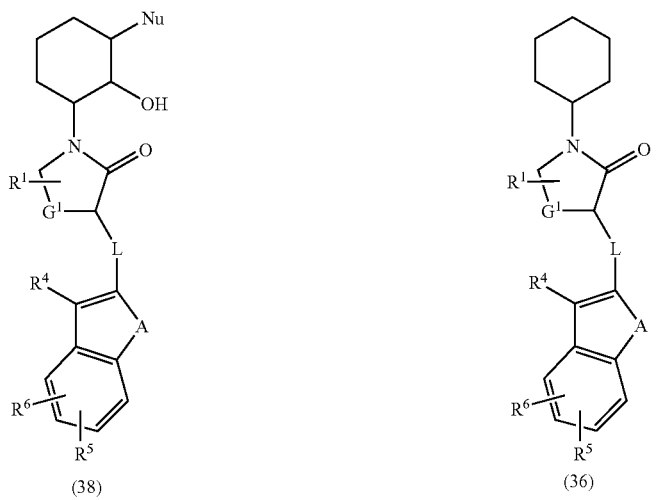

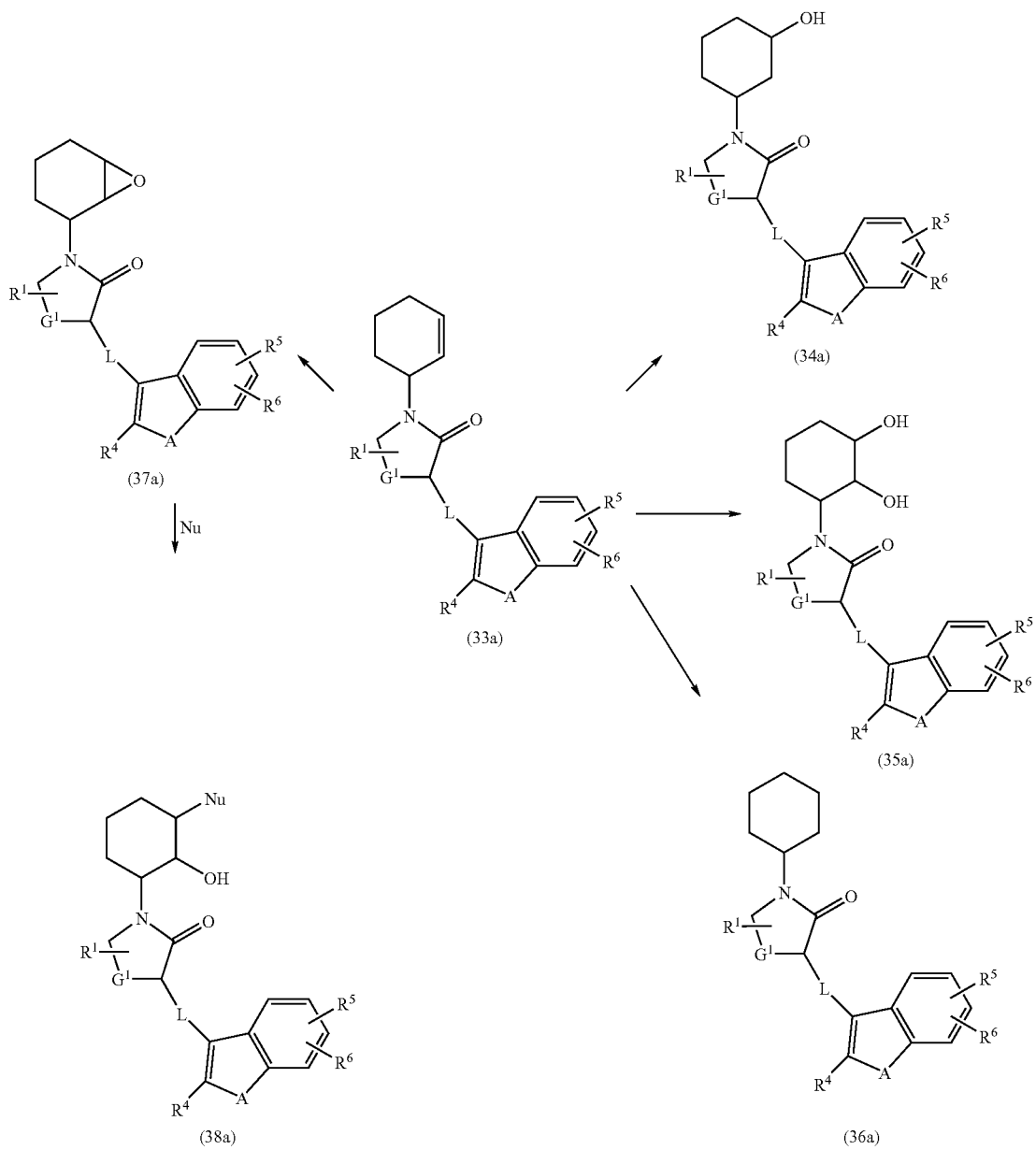

In Scheme J1 and J2, the cyclohexenyl product (33 or 33a) can be optionally oxidized via literature procedures to cyclohexyl alcohols (34 or 34a), diols (35 or 35a), reduced to the cyclohexyl moiety (36 or 36a), or be oxidized to an epoxide intermediate (37 or 37a). Epoxide intermediate (37 or 37a) can be further functionalized with a nucleophile to form substituted alcohols (38 or 38a).

-continued

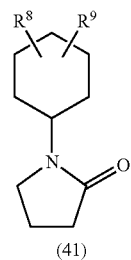

In Scheme K, substituted cyclohexyl alcohols (39), which are readily available either commercially or by known literature procedures can be converted to azides via treatment with diphenylphosphoryl azide (DPPA) and triphenyl azide and DEAD in THF to form the azide (40). During this reaction, the relative stereochemistry of the starting alcohol is inverted and is evident to those trained in the art. Treatment of the azide (40) with butyrylactone forms the lactam (41). During the Schmidt reaction the relative stereochemistry of the N-moiety to the substituents $R^8$ and $R^9$ is conserved as is evident to those trained in the art and is illustrated in the examples below.

Scheme L

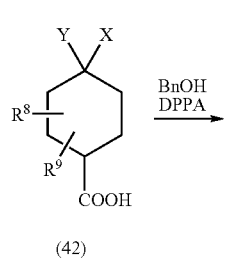

(42)

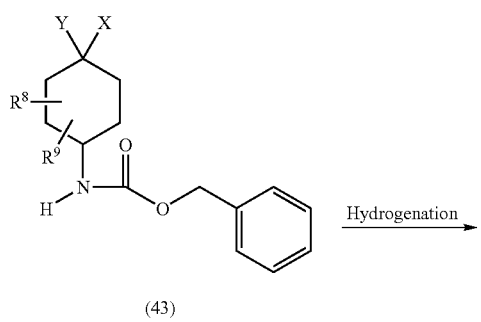

(43)

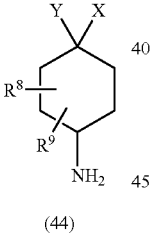

(44)

Scheme M1

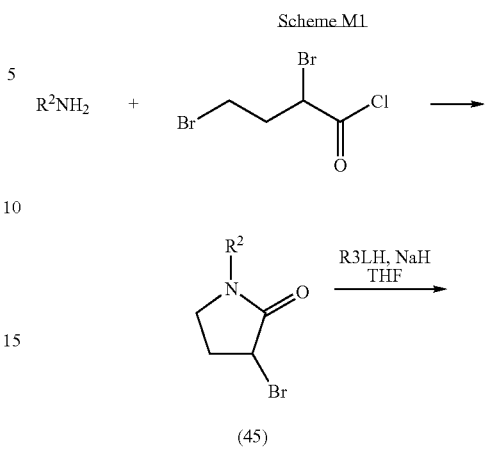

(45)

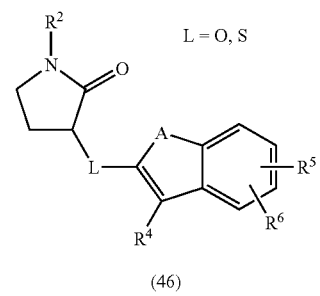

(46)

Scheme M2

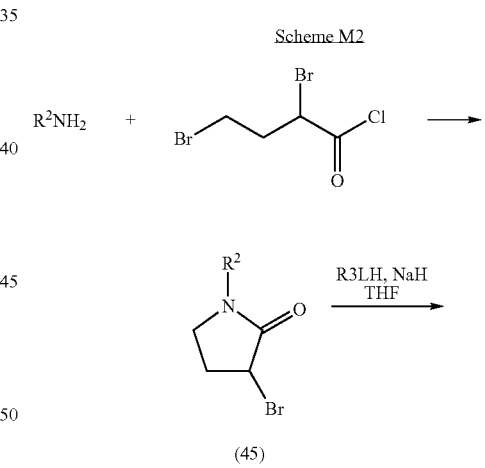

(45)

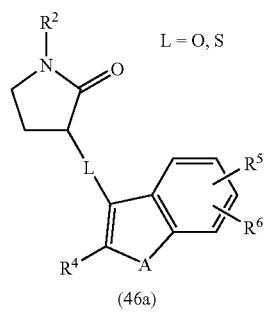

(46a)

In Scheme L, a variety of substituted cyclohexyl amines can be easily acquired from the substituted carboxylic acids (42), which are easily prepared via known literature methods [i.e., alkylation of a parent carboxylic acid with RX (X=halide or triflate)]. In this procedure the carboxylic acid is first subjected to Curtius rearrangement in the presence of benzyl alcohol to form the CBZ carbamate (43). In this reaction the relative stereochemistry of the starting material (42) is conserved as is evident to those trained in the art. Hydrogenation of the CBZ carbamate forms the amine (44). A variety of hydrogenation conditions can be used to effect this transformation as is evident to those trained in the art (i.e.; see Green's protecting group book for numerous conditions) (Greene, Protective Groups in Organic Synthesis, John Wiley & Sons, New York, N.Y.). These amine starting materials (44) are useful starting materials for Schemes E, G, H, and M to prepare the claimed lactams.

In Schemes M1 and M2, amines are acylated and cyclized with 2,4-dibromobutryl chloride to produce the N-alkylated-3-bromopyrrolidinones (45) in good yield (*J. Med. Chem.* (1987) 30, 1995-1998). The bromide can be displaced by hydroxybenzothiophenes, hydroxybenzofurans, thiobenzothiophenes, thiobenzofurans, aminobenzofurans, aminobenzothiophenes, alcohols, thiols, and amines to form the lactams (46 or 46a) [L=O, S].

Scheme N1

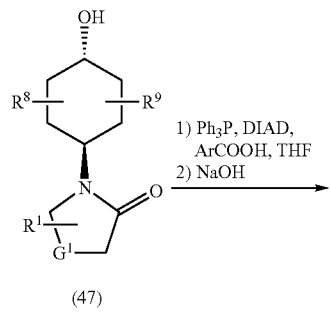

(47)

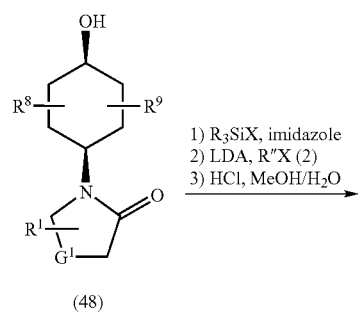

(48)

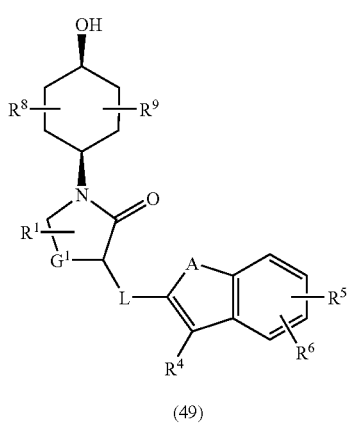

(49)

Scheme N2

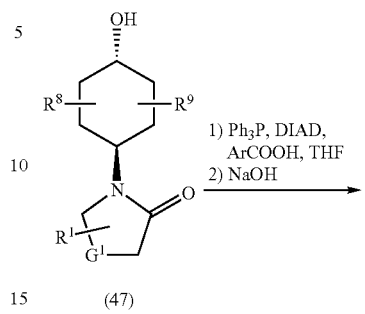

(47)

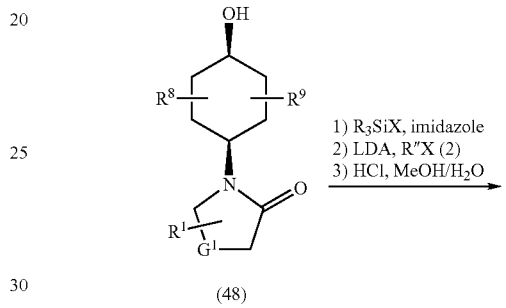

(48)

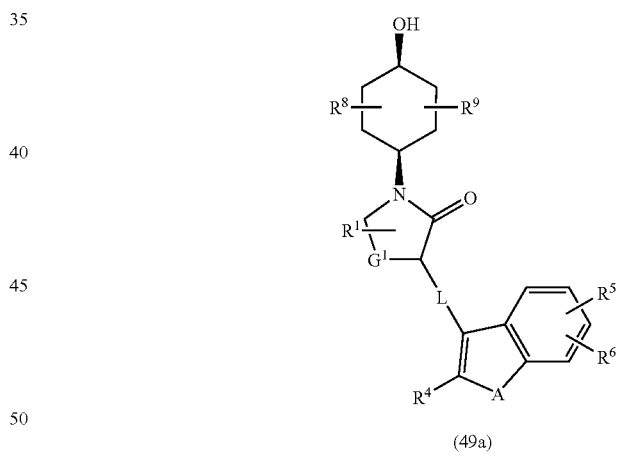

(49a)

In Scheme N1 and N2, a hydroxyl substituted lactam (47) stereochemistry is inverted with the Mitsunobu reaction to form its diastereomer (48) (trans to cis conversion illustrated here; but the reverse could easily be done). The alcohol substituted lactams are conveniently alkylated by first protecting the alcohol moiety with a silyl protecting group (TBS used but a variety of protecting groups from Green's Protecting Groups in Org Synthesis could be employed), and then alkylated employing the conditions of Scheme A. Deprotection of the alcohol with appropriate conditions (acid/HCl or fluoride deprotection of silyl moieties are convenient) yield the hydroxylated lactams (49 and 49a).

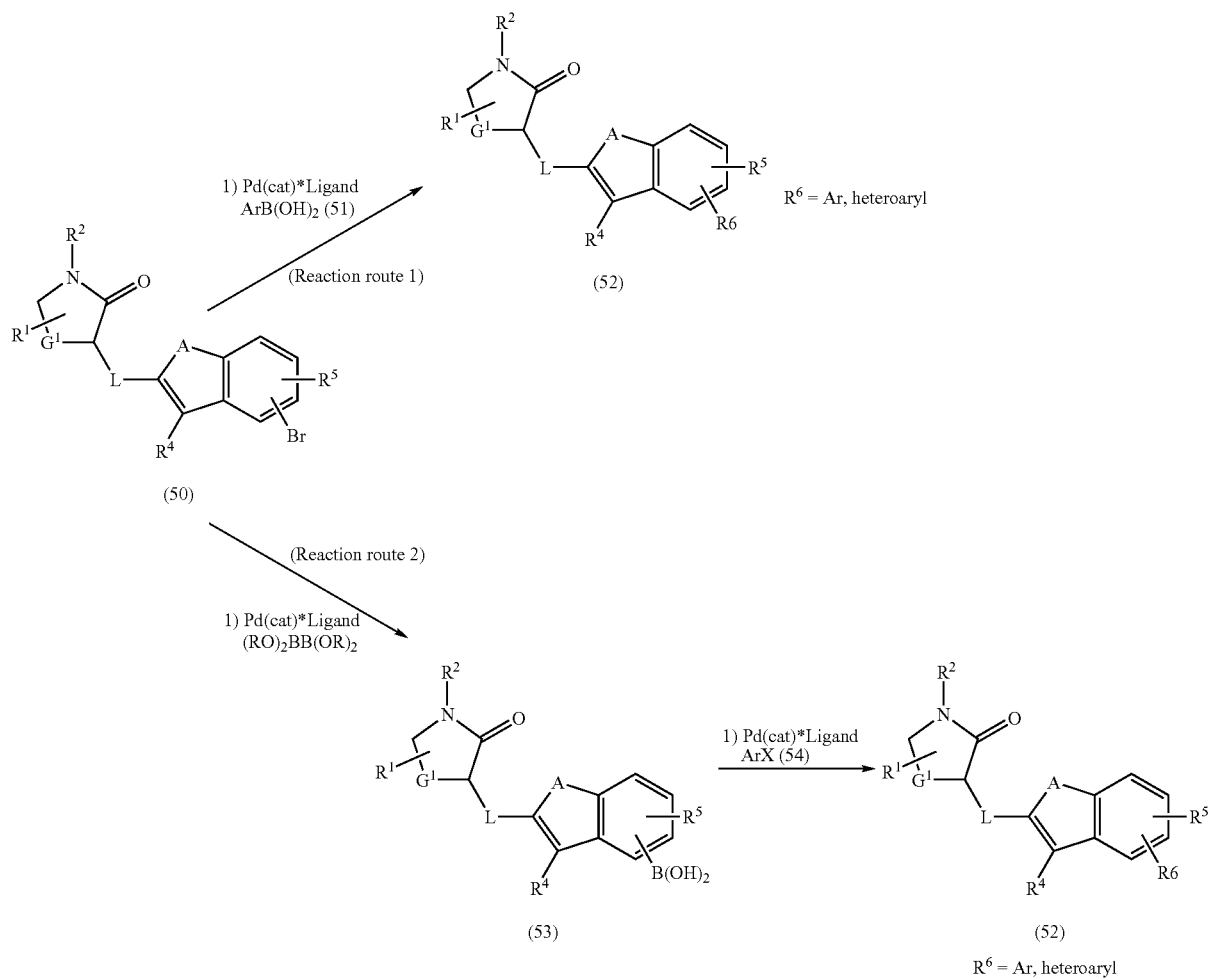
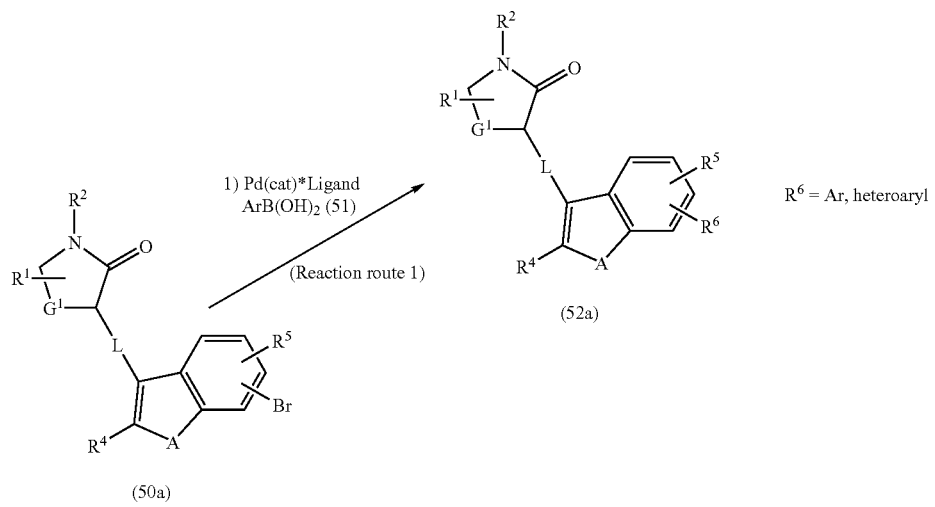

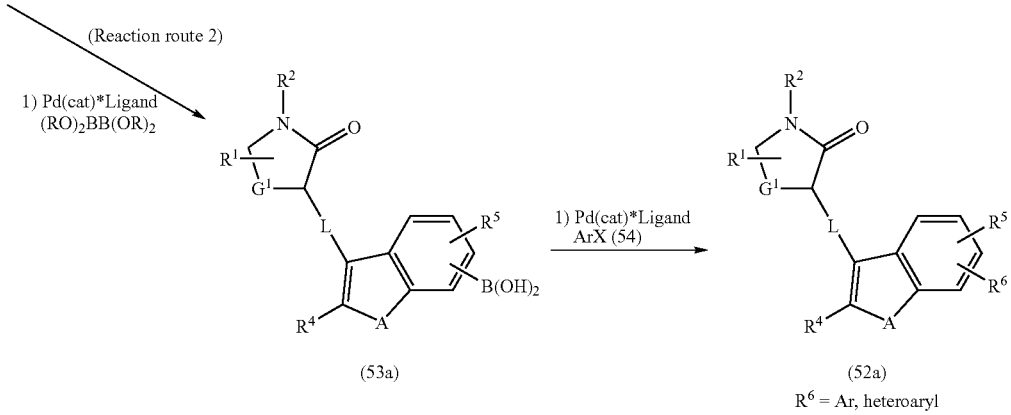

In Schemes O1 and O2, heteroaryl "Br" lactams (50 or 50a) (bromine as indicated by Br* can also be I, Cl, or OTf and this same chemistry would produce the drawn compounds with the appropriate catalysts known in the literature by those trained in the art) are converted to the biaryl/aryl-heteroaryl compounds by coupling to the appropriate aryl/heteroaryl boronic acid (51 or 51a) via reaction route 1 to produce the lactams (52 or 52a) directly. The linker (L) can be any of the following [$CH_2$, CHR, O, S, or $(CH_2)_n$]. It is also convenient to make the boronic acid convergent intermediate (53 and 53a) and couple with the appropriate Pd(cat) ligand system with a variety of aryl/heteroaryl halides/triflates (54) to form the lactams in two steps as shown in reaction route 2. This route is convenient and more versatile if the boronic acids (51) are not easy to prepare or acquire from commercial sources or literature methods.

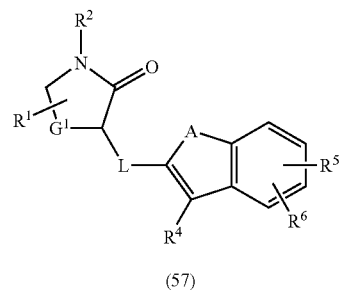

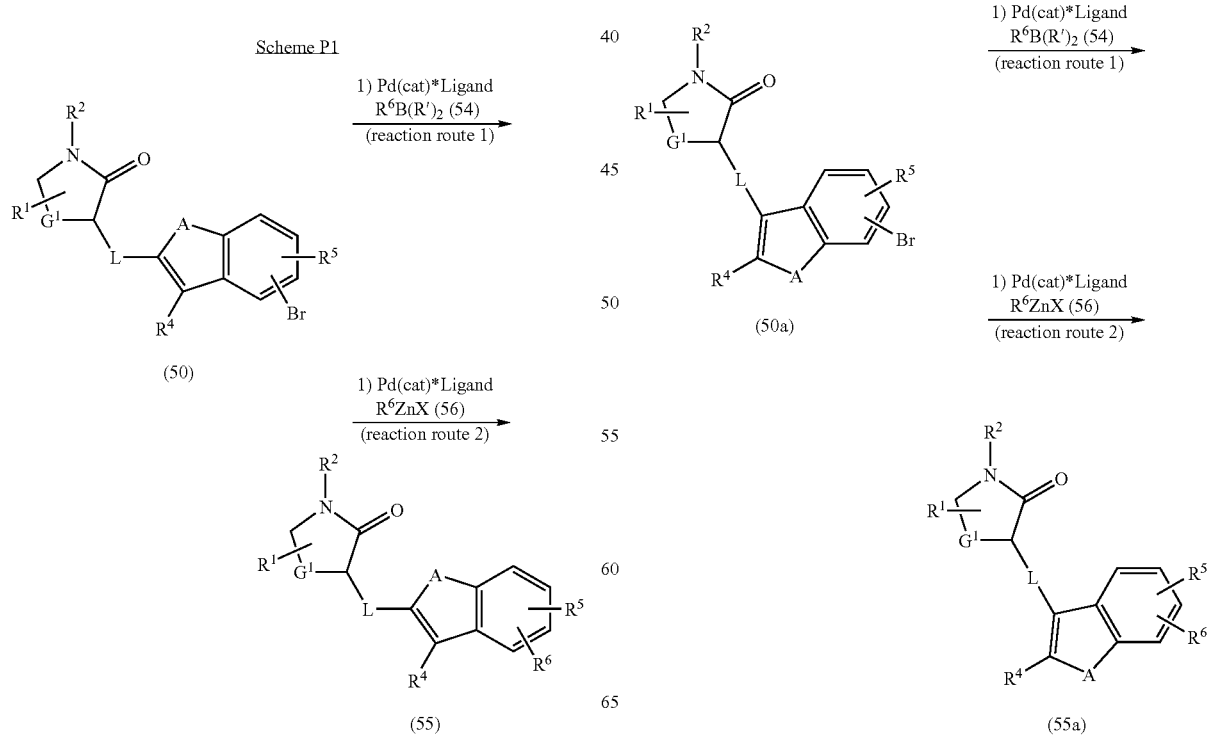

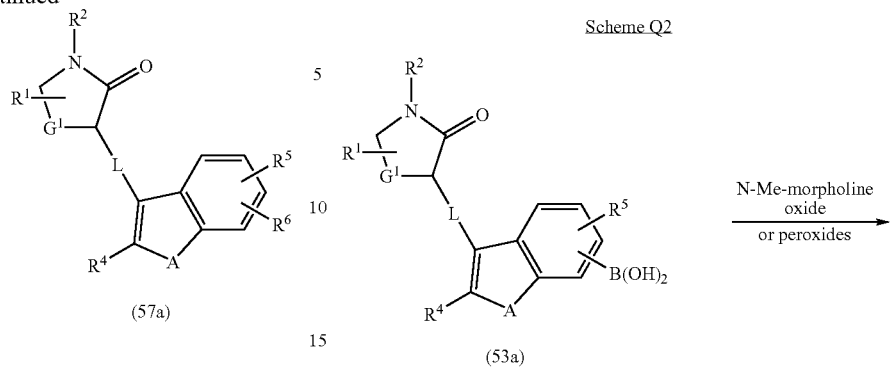

In Schemes P1 and P2, the heteroaryl bromides (Br could also be replaced with OTf, I) are conveniently converted into substituted arylalkyl lactams (eg., Br, I, Cl or Tf conversion to alkyl). This conversion (reaction route 1) is achieved via Pd-catalyzed insertion of $(R^6)_3B$ (54) or BBN—R6 [a subclass of (54) (made from either BBN—H regioselective addition to primary alkenes, or via organometallic addition of $R^6$-Metal to BBN—OMe)]. In reaction route 2, organometallic conversion to introduce alkyl moieties containing nitrile, ester and other functionality is a Pd-catalyzed Negishi insertion of an $R^6$ zinc halide (56) to the halide/triflate (50 or 50a) to produce the lactams (57 or 57a). This route is the preferred method for preparation of compounds of the structure where $R^6=(CH_2)_nFG$ (FG=COOR, CN). A similar Negishi reaction can be used to produce (57 or 57a) where $R^6$=CN when $R^6ZnX$ (56) is replaced with ZnCN in the reaction.

In Schemes Q1 and Q2, the boronic acids (53 or 53a) prepared in Scheme O1 and O2, are conveniently converted into hydroxyl substituted heteroaromatic lactams (58 and 58a) via oxidation with N-methyl morpholine oxide in a suitable solvent or via treatment of the boronic acid with another oxidizing agent such as peroxides. Other oxidants known in the literature could likely also be utilized. These hydroxyl substituted heteroaromatic lactams (58 and 58a) are useful starting materials in alkylations as in Scheme R.

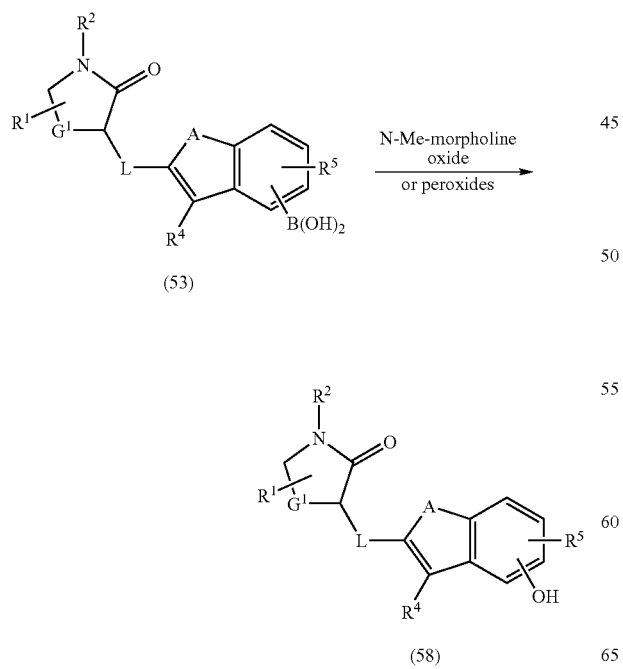

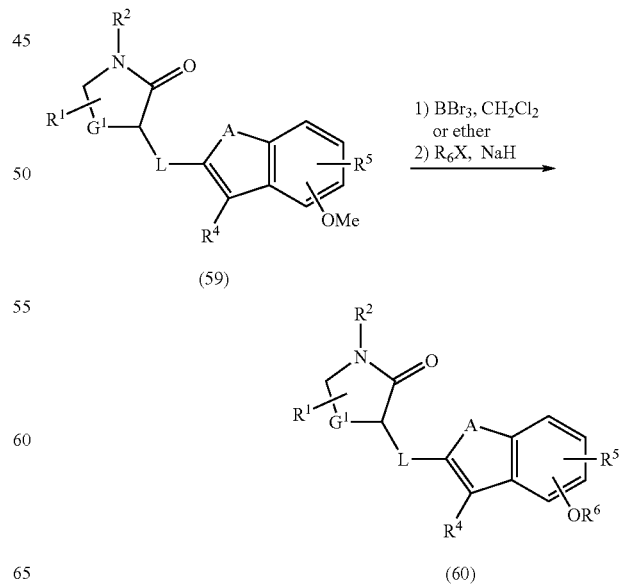

Scheme R2

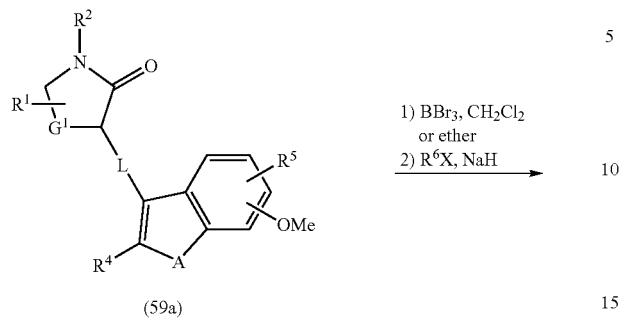

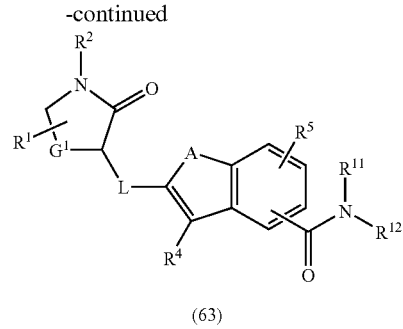

In Schemes R1 and R2, the methoxy functionalized lactams prepared via one of the above schemes, can be further elaborated via demethylation of the $OCH_3$ moiety of the lactam (59 or 59a) to make a hydroxyl substituted heteroaromatic lactam (58 or 58a) which can be alkylated with $(CH_2)_n FG$ (FG=functionalized group) to produce the lactam (60 or 60a). This chemistry is used to introduce moieties where $R=(CH_2)_n FG$ where FG=ester, acid, primary, secondary, and tertiary amines. It is expected that Mitsunobu reactions of the hydroxyl substituted heteroaromatic lactams (58 or 58a) with alcohols could also produce the lactams (60 or 60a). This should be the preferred method for more functionalized and sensitive $R^6$-substituents.

Scheme S1

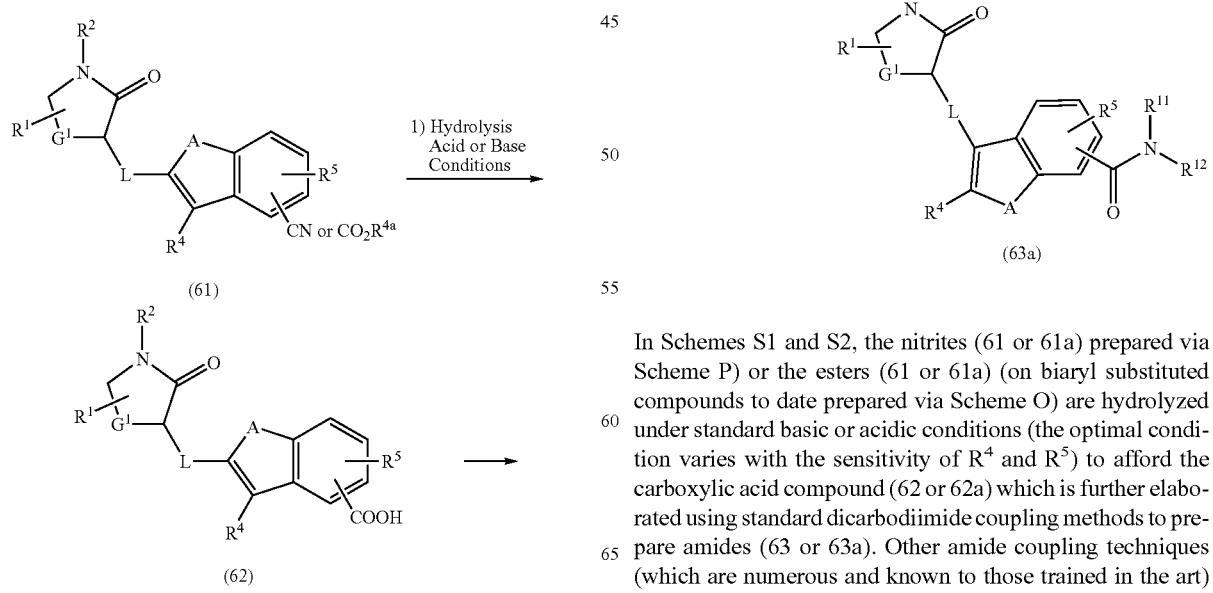

Scheme S2

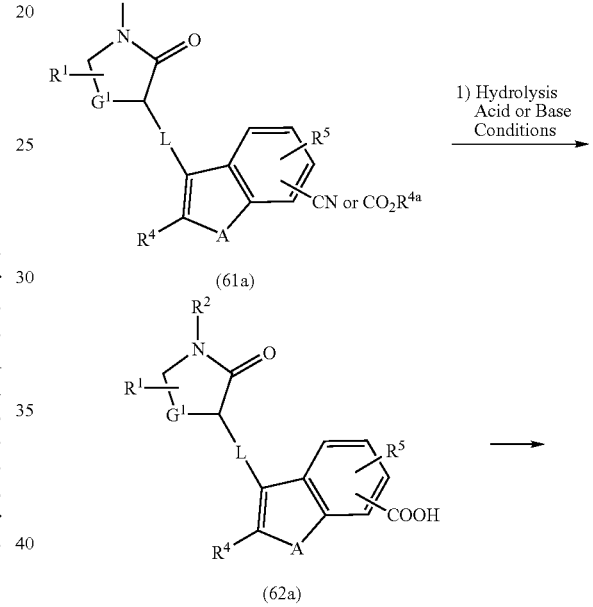

In Schemes S1 and S2, the nitrites (61 or 61a) prepared via Scheme P) or the esters (61 or 61a) (on biaryl substituted compounds to date prepared via Scheme O) are hydrolyzed under standard basic or acidic conditions (the optimal condition varies with the sensitivity of $R^4$ and $R^5$) to afford the carboxylic acid compound (62 or 62a) which is further elaborated using standard dicarbodiimide coupling methods to prepare amides (63 or 63a). Other amide coupling techniques (which are numerous and known to those trained in the art) would give amides (63 or 63a).

General Experimental Details

A Varian INOVA 400 MHz spectrometer is used to obtain ¹H NMR Specta the in the solvent indicated. A Finnigan LCQ Duo instrument using a mobile phase of 50% acetonitrile, 25% methanol, and 25% 2 mM aqueous ammonium acetate is used to obtain the Electrospray mass spectra. A Varian Prostar 210 instrument equipped with a PDA detector is used to run the analytical HPLC. A 5-cm YMC ODS-AQ column with a particle size of 3 microns is used as the stationary phase and 0.1% TFA in water is used as mobile phase A and 0.05% TFA in acetonitrile is used as mobile phase B. The standard method is a gradient of 5 to 95% B over 5 minutes, unless otherwise indicated. Starting materials are either purchased commercially, prepared as described, or prepared by the literature procedure indicated. ChemDraw version 7.0.1 (CambridgeSoft) is used to name the preparations and examples.

PREPARATIONS AND EXAMPLES

Preparation 1

1-(trans-4-hydroxy-cyclohexyl)-pyrrolidin-2-one

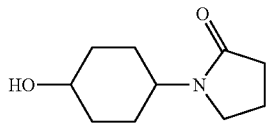

Add trans-4-aminocyclohexanol (230 g; 2.0 mol) to γ-butyrolactone (140 mL; 1.82 mol) in a 1 L round-bottom flask equipped with large magnetic stirrer, thermometer and condenser/nitrogen bubbler. Heat at 190° C. for 68 hours. Cool to ambient temperature and dissolve in water (1 L). Extract into dichloromethane (10×1.5 L). Dry the extracts over magnesium sulfate, filter and evaporate to a brown solid. Triturate with diethyl ether to afford 144.7 g (43%) of the title compound: LC-MS (M+1=184).

Preparation 2 cis-4-Nitro-benzoic acid 4-(2-oxo-pyrrolidin-1-yl)-cyclohexyl ester

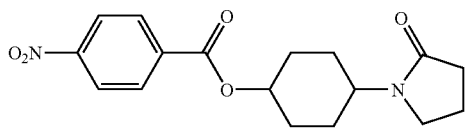

Dissolve 1-(trans-4-hydroxy-cyclohexyl)-pyrrolidin-2-one (preparation 1) (144 g; 0.79 mol) in dry tetrahydrofuran (5 L) and cool to −5° C. under nitrogen. Add triphenylphosphine (310 g; 1.185 mol) and 4-nitrobenzoic acid (198 g; 1.185 mol). Add diisopropyl azodicarboxylate (230 mL; 1.185 mol) drop-wise and stir at room temperature overnight. Add saturated aqueous sodium hydrogencarbonate (1 L) extract into dichloromethane (2×2.5 L) in a 20 L separating funnel. Dry the combined organic layers over magnesium sulfate, filter and concentrate. Purify over silica gel (iso-hexane/ethyl acetate 50-100% then 10% methanol in ethyl acetate) to afford 163 g (62%) of the title compound.

Preparation 3 cis-1-(4-hydroxy-cyclohexyl)-pyrrolidin-2-one

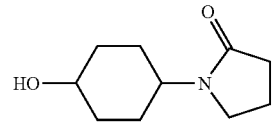

Dissolve cis-4-nitro-benzoic acid 4-(2-oxo-pyrrolidin-1-yl)-cyclohexyl ester (preparation 2) (87.9 g; 264 mmol) in methanol (1.35 L) and water (150 mL) and add potassium carbonate (109.5 g; 800 mmol). Stir at room temperature overnight to give a white precipitate. Evaporate to dryness. Azeotrope with ethanol (×2). Stir in tetrahydrofuran (1 L) for 1 hour then filter. Evaporate the filtrate to an oil and crystallize from diethyl ether (100 mL) to afford 40 g (83%) of the title compound.

Preparation 4 cis-1-[4-(tert-butyl-dimethyl-silanyloxy)-cyclohexyl]-pyrrolidin-2-one

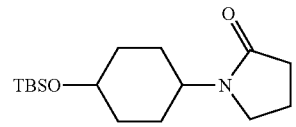

Dissolve cis-1-(4-hydroxy-cyclohexyl)-pyrrolidin-2-one (preparation 3) (40 g; 220 mmol) in dry dichloromethane (1 L). Add imidazole (22.5 g; 330 mmol) followed by tert-butyldimethylsilyl chloride (50 g; 330 mmol). Stir under nitrogen at room temperature overnight. Wash with water (250 mL) and saturated aqueous sodium hydrogencarbonate (250 mL). Dry over magnesium sulfate, filter and evaporate to an oil. Pass through a silica gel pad with iso-hexane/ethyl acetate (0-50%) to afford 51 g (79%) the title compound as a clear, pale-yellow oil: LC-MS (M+1=298.5).

Preparation 5

7-Chloro-1,3-dioxa-5-thia-s-indacen-6-yl)-methanol

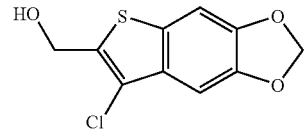

Slowly add a solution of 7-chloro-1,3-dioxa-5-thia-s-indacene-6-carbonyl chloride (2.00 g, 7.27 mmol) in THF (15 mL) to a mixture of sodium borohydride (6 molar equivalents) in EtOH (20 mL/g) at 0° C. Stir to room temperature for an hour. Quench with water (60 mL/g). Concentrate to the volume of the added water. Extract with ether, wash with water, brine, dry, and concentrate to afford the title compound as a white powder (1.64 g, 93%): $^1$H NMR (CDCl$_3$) δ 7.17 (d, 2H), 6.05 (s, 2H), 4.92 (d, 2H), 1.89 (t, 1H).

Preparation 6

6-Bromomethyl-7-chloro-1,3-dioxa-5-thia-s-indacene

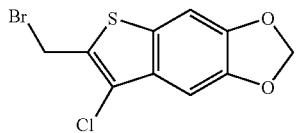

Add a solution of phosphorous tribromide (1.5 equivalents) in ether (10 mL/g) to a solution of (7-chloro-1,3-dioxa-5-thia-s-indacen-6-yl)-methanol (1.64 g, 6.8 mmol) in ether (20 mL/g) at 0° C. Stir to room temp for an hour. Pour onto ice water, wash with water, saturated sodium bicarbonate, brine, dry, and concentrate to afford the title compound as a white powder (1.96 g, 95%): $^1$H NMR (CDCl$_3$) δ 7.17 (s, 1H), 7.13 (s, 1H), 6.05 (s, 2H), 4.72 (d, 2H).

Preparation 7

(3-Methyl-benzo[b]thiophen-2-yl)-methanol

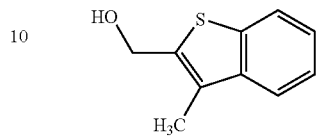

Add a solution of methyl 3-methylbenzo[b]thiophen-2-carboxylate (5.00 g, 24.2 mmol) in THF (25 mL) dropwise to a 1M solution of lithium aluminum hydride in THF (121 mL, 121 mmol) at 0° C. Stir 1 hour. Add an excess of sodium sulfate decahydrate portionwise (slowly at first), stir for 30 minutes at 0° C., then 2 hours at room temperature. Filter, and wash the cake with THF. Concentrate the combined filtrates to afford the drawn product as a white solid (3.60 g, 83%): $^1$H NMR (CDCl$_3$) δ 7.81 (m, 1H), 7.68 (m, 1H), 7.35 (m, 2H), 4.92 (d, 2H), 2.40 (s, 3H), 1.77 (t, 1H).

TABLE 1

The following examples are prepared essentially as described in Preparation 5 except using the reagents in the "Reagents used" column.

| Preparation | Structure and name | Reagents used | |
|---|---|---|---|
| 9 | (3-Chloro-6-fluoro-benzo[b]thiophen-2-yl)-methanol | 3-chloro-6-fluoro-benzo[b]thiophene-2-carbonyl chloride (2.00 g, 8.03 mmol) | $^1$H NMR (CDCl$_3$) δ 7.74 (dd, 1 H), 7.50 (dd, 1 H, 7.20 (m, 1 H), 4.96 (d, 2 H), 1.97 (t, 1 H). |
| 11 | (3-Methyl-benzofuran-2-yl)-methanol | 3-methyl-benzofuran-2-carbonyl chloride (5.00 g, 25.7 mmol) | $^1$H NMR (CDCl$_3$) δ 7.49 (m, 1 H), 7.43 (m, 1 H), 7.26 (m, 2 H), 4.76 (d, 2 H), 2.26 (s, 3 H), 1.84 (t, 1 H) |
| 13 | (3-Chloro-6-methoxy-benzo[b]thiophen-2-yl)-methanol | 3-chloro-6-methoxy-benzo[b]thiophene-2-carbonyl chloride (1.82 g, 6.97 mmol) | $^1$H NMR (CDCl$_3$) δ 7.67 (d, 1 H), 7.26 (m, 1 H), 7.06 (dd, 1 H), 4.94 (d, 2 H), 3.88 (s, 3 H), 1.91 (t, 1 H) |

TABLE 2

The following examples are prepared essentially as described in Preparation 6 except using the reagents in the "Reagents used" column.

| Preparation | Structure and name | Reagents used | |
|---|---|---|---|
| 8 | 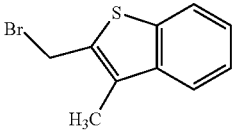<br>2-Bromomethyl-3-methyl-benzo[b]thiophene | 3-methyl-benzo[b]thiophen-2-yl)-methanol (3.60 g, 20.2 mmol) | $^1$H NMR (CDCl$_3$) δ 7.77 (m, 1 H), 7.68 (m, 1 H), 7.37 (m, 2 H), 4.77 (s, 2 H), 2.39 (s, 3 H) |
| 10 | 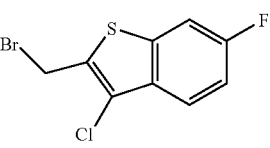<br>2-Bromomethyl-3-chloro-6-fluoro-benzo[b]thiophene | (3-chloro-6-fluoro-benzo[b]thiophen-2-yl)-methanol (1.65 g, 7.62 mmol) | $^1$H NMR (CDCl$_3$) δ 7.75 (dd, 1 H), 7.46 (dd, 1 H), 7.21 (m, 1 H), 4.78 (d, 2 H) |
| 12 | 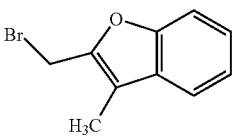<br>2-Bromomethyl-3-methyl-benzofuran | (3-methyl-benzofuran-2-yl)-methanol (4.02 g, 24.8 mmol) | $^1$H NMR (CDCl$_3$) δ 7.46 (m, 2 H), 7.31 (m, 1 H), 7.24 (m, 1 H), 4.64 (s, 2 H), 2.25 (s, 3 H) |
| 14 | 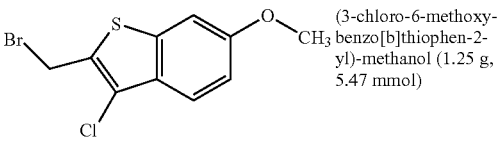<br>2-Bromomethyl-3-chloro-6-methoxy-benzo[b]thiophene | (3-chloro-6-methoxy-benzo[b]thiophen-2-yl)-methanol (1.25 g, 5.47 mmol) | $^1$H NMR (CDCl$_3$) δ 7.67 (d, 1 H), 7.23 (d, 1 H), 7.06 (dd, 1 H), 4.79 (s, 2 H), 3.88 (s, 3 H) |
| 16 | 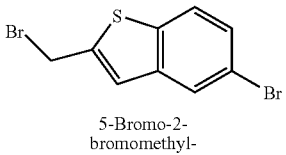<br>5-Bromo-2-bromomethyl-benzo[b]thiophene | (5-bromo-benzo[b]thiophen-2-yl)-methanol (10.3 g, 42 mmol) | $^1$H NMR (CDCl$_3$) δ 7.85-7.87 (m, 1 H), 7.64 (d, J = 8.59 Hz, 1 H), 7.41-7.45 (m, 1 H), 7.24-7.27 (m, 1 H), 4.76 (s, 2 H) |
| 17 | 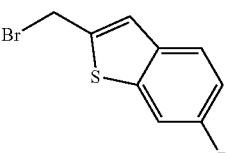<br>6-Bromo-2-bromomethyl-benzo[b]thiophene | (6-bromo-benzo[b]thiophen-2-yl)-methanol (2.5 g, 10 mmol) | $^1$H NMR (CDCl$_3$) δ 7.92-7.94 (m, 1 H), 7.56 (d, J = 8.59 Hz, 1 H), 7.45 (dd, J = 8.59, 1.95 Hz, 1 H), 7.28 (s, 1 H), 4.75 (s, 2 H) |

Preparation 15

(5-Bromo-benzo[b]thiophen-2-yl)-methanol

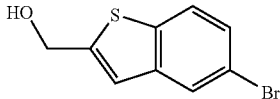

Dissolve 5-bromo-benzo[b]thiophene-2-carboxylic acid (21.2 g, 82.5 mmol) in THF (150 mL). Cool to 0° C. with an ice bath. Add 2M BH3 dimethyl sulfide complex in THF (82.5 mL). Stir to room temperature over 2 hours. Quench by careful addition of water. Partition between ether and saturated NaHCO$_3$, wash with water, brine, dry, and concentrate. Purify via column chromatography eluting with 3:1 hexanes:ethyl acetate to afford a white solid (10.3 g): $^1$H NMR (CDCl$_3$) δ 7.87 (m, 1H), 7.67 (d, 1H), 7.41 (dd, 1H), 7.15 (m, 1H), 4.94 (d, 2H), 1.91 (t, 1H).

Preparation 18

4-[2-(1-Cyclohexyl-2-oxo-pyrrolidin-3-ylmethyl)-benzo[b]thiophen-5-yl]-benzoic acid methyl ester

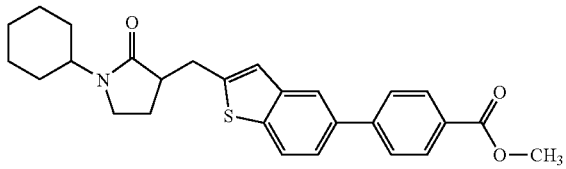

Using the procedure to synthesize Example 17 and using reagents 3-(5-bromo-benzo[b]thiophen-2-ylmethyl)-1-cyclohexyl-pyrrolidin-2-one (250 mg, 0.64 mmol) and 4-methoxycarbonylphenylboronic acid (200 mg, 1 mmol) afford the title compound as a white powder (160 mg, 78%): MS (APCI-pos mode) m/z (rel intensity): 342.2 (M+H, 100%).

Preparation 19

Trans-1-(4-[tert-butyl-dimethyl-silanyloxy)-cyclohexyl]-piperidin-2-one

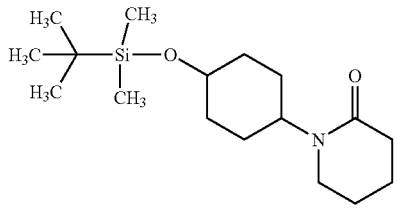

Trans-(4-hydroxy-cyclohexyl)-carbamic acid benzyl ester Combine trans-cyclohexylamine hydrochloride (14.0 g, 92.3 mmol), sodium carbonate (19.6 g, 0.185 mol), DCM (50 mL), water (50 mL) and stir for 5 minutes at room temperature. Add benzoyl chloroformate (15.6 mL, 111 mmol) dropwise to the reaction mixture and stir at room temperature for 2 hours. Separate the organic layer, wash with water (3×50 mL) and dry over anhydrous Na$_2$SO$_4$. Evaporate the solvent to obtain the desired intermediate as a white solid (22.7 g, 99%).

Trans-[4-(tert-butyl-dimethyl-silanyloxy)-cyclohexyl]-carbamic acid benzyl ester: Combine trans-(4-hydroxy-cyclohexyl)-carbamic acid benzyl ester (16.0 g, 0.064 mol), imidazole (13.9 g, 0.10 mol), and anhydrous THF (300 mL), add tert-butyldimethylsilyl chloride (14.5 g, 0.10 mol) and stir at room temperature for 18 hours. Wash the reaction mixture with water (250 mL), saturated aqueous NaHCO$_3$ (250 mL) and dry the organic layer over anhydrous Na$_2$SO$_4$. Remove the solvent and purify the residue by chromatography over silica gel (eluting with 0 to 30% EtOAc in hexane) to obtain the desired intermediate as clear oil (23.0 g, 98%).

Trans-4-(tert-butyl-dimethyl-silanyloxy)-cyclohexylamine: Combine trans-[4-(tert-butyl-dimethyl-silanyloxy)-cyclohexyl]-carbamic acid benzyl ester (23.0 g, 0.06 mol), palladium, 10% wt. on activated carbon (0.5 g), in EtOAc (100 mL) and charge the flask with hydrogen (50 psi). After 3 hours, filter the reaction mixture through a pad of Celite® and evaporate the solvent to obtain the desired intermediate as a dark oil (14.4 g, 99%): MS (EI) m/z=229 (M+).

Trans-5-chloro-pentanoic acid-[4-tert-butyl-dimethyl-silanyloxy)-cyclohexyl]-amide: Combine 5-chlorovaleric acid (19.7 g, 0.16 mol), thionyl chloride (20 mL) and reflux for 3 hours. Remove unreacted thionyl chloride by evaporation with toluene (3×10 mL) to obtain 5-chloro-pentanoyl chloride as a clear oil (24.1 g, 97%). Combine trans-4-(tert-butyl-dimethyl-silanyloxy)-cyclohexylamine (17.7 g, 0.08 mol), and anhydrous pyridine (10.9 mL, 0.23 mol) in anhydrous DCM (100 mL) and cool to 0° C. Add 5-chloro-pentanoyl chloride (14.2 g, 0.09 mol) dropwise to the reaction mixture and stir at room temperature for 1 hour. Partition the reaction mixture between brine and EtOAc. Dry the organic layer over Na$_2$SO$_4$, evaporate the solvent and purify the residue by chromatography over silica gel (eluting with 0 to 30% EtOAc in hexane) to obtain the desired intermediate as a colorless oil (22.7 g, 85%): MS (ES+) m/z=349 (M+H)$^+$.

Trans-1-(4-[tert-butyl-dimethyl-silanyloxy)-cyclohexyl]-piperidin-2-one: Dissolve trans-5-chloro-pentanoic acid-[4-(tert-butyl-dimethyl-silanyloxy)-cyclohexyl]-amide (22.7 g, 65.1 mmol) in anhydrous THF (500 mL), add sodium hydride (60% dispersion in mineral oil, 13.0 g, 0.32 mol) by portions and heat the reaction mixture at 70° C. for 18 hours. Cool the reaction mixture to room temperature, quench with water (200 mL) and extract with DCM (3×100 mL). Dry the organic layer over anhydrous Na$_2$SO$_4$, remove the solvent and purify the residue by chromatography over silica gel (eluting with 0 to 50% EtOAc in hexane) to obtain the title compound as a white solid (15.0 g, 74%): MS (ES+) m/z=312 (M+H)$^+$.

Preparation 20

Cis-1-[4-(tert-butyl-dimethyl-silaniloxy)-cyclohexyl]-piperidin-2-one

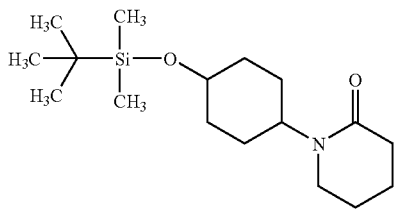

Trans-1-(4-hydroxy-cyclohexyl)-piperidin-2-one: Dissolve trans-1-(4-[tert-butyl-dimethyl-silanyloxy)-cyclohexyl]-piperidin-2-one (10 g, 21.1 mmol) in ethanol containing concentrated hydrochloric acid (5% v/v, 30 mL) and stir at room temperature for 18 hours. Evaporate the solvent, take the residue up in DCM (300 mL) and wash with saturated aqueous NaHCO$_3$ (100 mL). Dry the organic layer over anhydrous Na$_2$SO$_4$ and remove the solvent to obtain the desired intermediate as a clear oil (4.0 g, 95%): MS (ES+) m/z=198 (M+H)$^+$.

Cis-4-nitro-benzoic acid-4-(2-oxo-piperidin-1-yl)-cyclohexyl-ester: Dissolve trans-1-(4-hydroxy-cyclohexyl)-piperidine-2-one (4.0 g, 20.0 mol) in THF (250 mL), cool to −5° C. and add triphenyl phosphine (12.0 g, 0.05 mol) and benzoic acid (8.4 g, 0.05 mol). Add diisopropylazodicarboxylate (10.1 g, 0.05 mol) dropwise to the reaction mixture, warm to room temperature and stir for 18 hours. Quench the reaction mixture with saturated aqueous NaHCO$_3$ and extract with DCM (3×100 mL). Dry the organic layer over anhydrous Na$_2$SO$_4$, remove the solvent and purify the residue by chromatography over silica gel eluting with EtOAc to obtain the desired intermediate (5.0 g, 72%): MS (ES+) m/z=347 (M+H)$^+$.

Cis-1-[4-(tert-butyl-dimethyl-silaniloxy)-cyclohexyl]-piperidin-2-one: Dissolve cis-4-nitro-benzoic acid-4-(2-oxo-piperidin-1-yl)-cyclohexyl-ester (5.0 g, 14.4 mmol) in methanol (150 mL), add water (20 mL), K$_2$CO$_3$ (8.7 g, 0.06 mol) and stir the reaction mixture at room temperature for 18 hours. Extract the reaction mixture with DCM (2×100 mL), dry the organic layer over Na$_2$SO$_4$ and remove the solvent to obtain cis-1-(4-hydroxy-cyclohexyl)-piperidin-2-one as clear oil (6.0 g). Combine cis-1-(4-hydroxy-cyclohexyl)-piperidin-2-one (6.0 g, 0.03 mol), imidazole (3.1 g, 0.05 mol), tert-butyl chloro dimethyl silane (6.9 g, 0.05 mol) and stir at room temperature for 18 hours. Wash the reaction mixture with water (150 mL) and dry the organic layer over Na$_2$SO$_4$. Remove the solvent and purify the residue by chromatography over silica gel (eluting with 0 to 50% EtOAc in hexane) to obtain the title compound as a clear oil (3.4 g, 76%): MS (ES+) m/z=312 (M+H)$^+$.

Preparation 21 trans-1-{4-(tert-Butyl-dimethyl-silanyloxy)-cyclohexy}3-(3-chloro-benzo[b]thiophen-2-ylmethyl)-piperidin-2-one

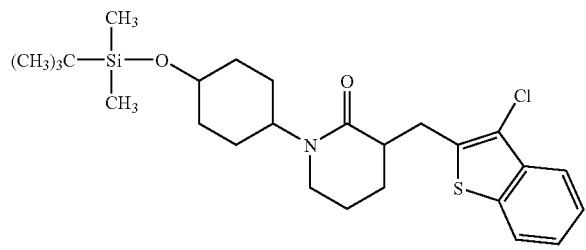

Place trans-1-[4-(tert-Butyl-dimethyl-silanyloxy)-cyclohexyl]-piperidin-2-one, (300 mg, 0.96 mmol) in 7.0 mL of THF, cool to −78° C. and treat with 2.0 M LDA (0.72 mL, 1.5 mmol). Stir for 5.0 minutes, treat with 2-bromomethyl-3-chloro-benzo[b]thiophene (375 mg, 1.5 mmol) and stir overnight at room temperature. Quench reaction with ammonium chloride, extract with dichloromethane, dry over sodium sulfate and purify via silica chromatography (ethyl acetate/hexanes 0-25%) affords 310 mg (65

Preparation 22 cis-1-{4-(tert-Butyl-dimethyl-silanyloxy)-cyclohexy}3-(3-chloro-benzo[b]thiophen-2-ylmethyl)-piperidin-2-one

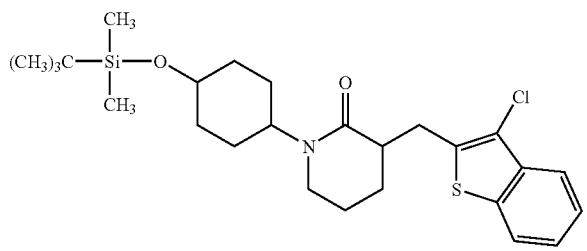

Place cis-1-[4-(tert-Butyl-dimethyl-silanyloxy)-cyclohexyl]-piperidin-2-one, (300 mg, 0.96 mmol) in 7.0 mL of THF, cool to −78° C. and treat with 2.0 M LDA (0.72 mL, 1.5 mmol). Stir for 5.0 minutes, treat with 2-bromomethyl-3-chloro-benzo[b]thiophene (250 mg, 0.96 mmol) and stir at −78° C. for five hours, and warm to room temperature. Quench reaction with ammonium chloride, extract with dichloromethane, dry over sodium sulfate and purify via silica chromatography (ethyl acetate/hexanes 0-25%) affords 166 mg (35%).

Example 1

3-Benzo[b]thiophen-2-ylmethyl-1-cyclohexyl-pyrrolidin-2-one

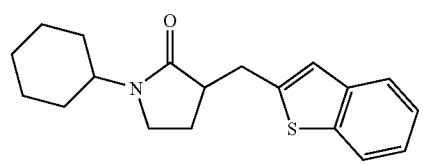

Place 1-cyclohexyl-pyrrolidin-2-one (500 mg) in THF (30 mL) and cool to −78° C. Slowly add lithium diisopropylamide (LDA) (2M, 1.5 eq) and stir for 15 minutes. Add 2-bromomethyl-benzo[b]thiophene [*J. Med. Chem.* (1992) 1176-1183] (815 mg, 3.59 mmol) and stir for 3 hours. Quench with ammonium chloride and extract with dichloromethane. Dry over sodium sulfate, filter, and concentrate. Purify by silica gel (20-50% ethyl acetate in hexanes) to give 670 mg, 71% of the title compound as a white powder. MS (APCI-pos mode) m/z (rel intensity) 314 (100).

TABLE 3

The following examples are prepared essentially as described in Example 1 except using the reagents in the "Reagents used" column.

| Example | Structure and name | Reagents used | Mass spec |
|---|---|---|---|
| 2 | 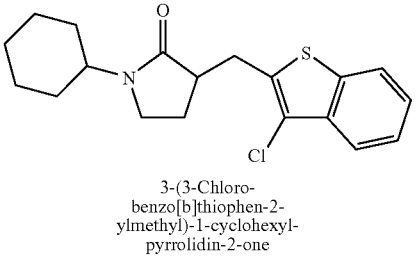<br>3-(3-Chloro-benzo[b]thiophen-2-ylmethyl)-1-cyclohexyl-pyrrolidin-2-one | 1-cyclohexyl pyrrolidinone (959 mg, 5.73 mmol) and 2-bromomethyl-3-chloro-benzo[b]thiophene (US 4,939,140) (1.00 g, 3.82 mmol) | (APCI-pos mode) m/z (rel intensity) 348 (100), 350 (40) |
| 3 | 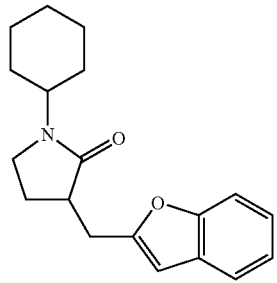<br>3-Benzofuran-2-ylmethyl-1-cyclohexyl-pyrrolidin-2-one | 1-cyclohexyl pyrrolidinone (357 mg, 2.13 mmol) and 2-bromomethyl-benzofuran [J. Med. Chem. (1987) 400-405] (300 mg, 1.42 mmol) | (apci) m/z = 298.2 (M + H) |
| 4 | 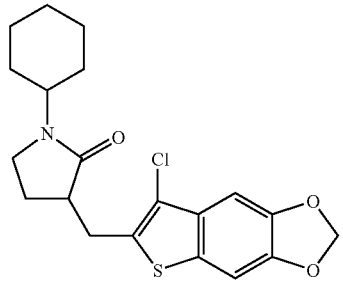<br>3-(7-Chloro-1,3-dioxa-5-thia-s-indacen-6-ylmethyl)-1-cyclohexyl-pyrrolidin-2-one | 1-cyclohexyl pyrrolidinone (0.360 g, 2.15 mmol) and 6-bromomethyl-7-chloro-1,3-dioxa-5-thia-s-indacene (0.439 g, 1.44 mmol) | (APCI-pos mode) m/z (rel intensity) 392.2 (100), 394.1 (40) |
| 5 | 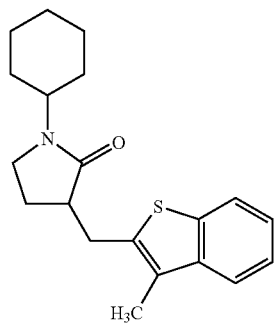<br>1-Cyclohexyl-3-(3-methyl-benzo[b]thiophen-2-ylmethyl)-pyrrolidin-2- | 1-cyclohexyl pyrrolidinone (620 mg, 3.70 mmol) and 2-bromomethyl-3-methyl-benzo[b]thiophene (600 mg, 2.47 mmol) | (apci) m/z = 328.2 (M + H) |

TABLE 3-continued

The following examples are prepared essentially as described in Example 1 except using the reagents in the "Reagents used" column.

| Example | Structure and name | Reagents used | Mass spec |
|---|---|---|---|
| 6 | 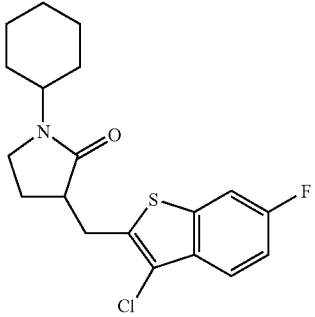<br>3-(3-Chloro-6-fluoro-benzo[b]thiophen-2-ylmethyl)-1-cyclohexyl-pyrrolidin-2-one | 1-cyclohexyl pyrrolidinone (0.396 mg, 2.37 mmol) and 2-bromomethyl-3-chloro-6-fluoro-benzo[b]thiophene (0.389, 1.39 mol) | (APCI-pos mode) m/z (rel intensity) 366.2 (100), 368.2 (40) |
| 7 | 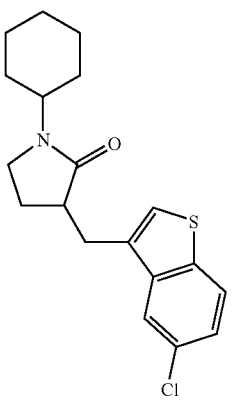<br>3-(5-Chloro-benzo[b]thiophen-3-ylmethyl)-1-cyclohexyl-pyrrolidin-2-one | 1-cyclohexyl pyrrolidinone (400 mg, 2.39 mmol) and 5-bromo-3-chloromethyl-benzo[b]thiophene (938 mg, 3.59 mmol) | (apci) m/z = 348.2 (M + H) |
| 8 | 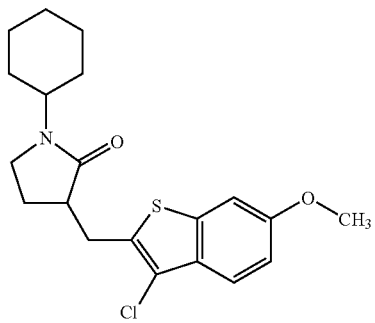<br>3-(3-Chloro-6-methoxy-benzo[b]thiophen-2-ylmethyl)-1-cyclohexyl-pyrrolidin-2-one | 1-cyclohexyl pyrrolidinone (1.118 g, 6.69 mmol) and 2-bromomethyl-3-chloro-6-methoxy-benzo[b]thiophene (1.30 g, 4.46 mmol) | (apci) m/z = 378.2 (M + H) |

TABLE 3-continued

The following examples are prepared essentially as described in Example 1 except using the reagents in the "Reagents used" column.

| Example | Structure and name | Reagents used | Mass spec |
|---|---|---|---|
| 9 | 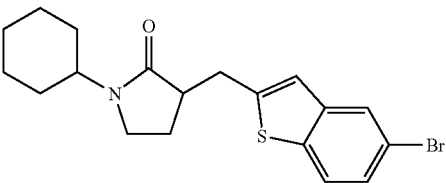<br>3-(5-Bromo-benzo[b]thiophen-2-ylmethyl)-1-cyclohexyl-pyrrolidin-2-one | 1-cyclohexyl pyrrolidinone (6.8 g, 40 mmol) and 5-bromo-2-bromomethyl-benzo[b]thiophene (6.0 g, 20 mmol) | (APCI-pos mode) m/z (rel intensity): 392.1 (M + H, 100%) |
| 10 | 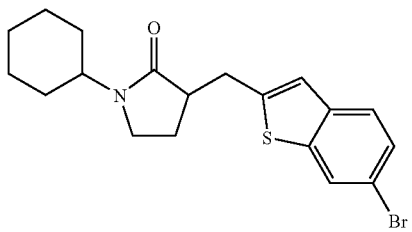<br>3-(6-Bromo-benzo[b]thiophen-2-ylmethyl)-1-cyclohexyl-pyrrolidin-2-one | 1-cyclohexyl pyrrolidinone (0.7 g, 4 mmol) and 6-bromo-2-bromomethyl-benzo[b]thiophene (0.5 g, 2 mmol) | (APCI-pos mode) m/z (rel intensity): 392.1 (M + H, 100%) |

Example 11

3-(3-Chloro-benzo[b]thiophen-2-ylmethyl)-1-(cis-4-hydroxy-cyclohexyl)-pyrrolidin-2-one

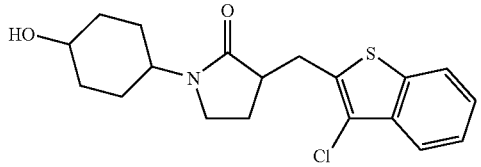

Charge a flask with cis-1-[4-(tert-butyl-dimethyl-silanyloxy)-cyclohexyl]-pyrrolidin-2-one (0.50 g, 1.68 mmol) (1.0 eq), dissolve with THF (0.2 M) and cool to −78° C. Add LDA (1.1 to 1.5 eq) and stir at −78° C. for 5 minutes. Add 2-bromomethyl-3-chloro-benzo[b]thiophene (U.S. Pat. No. 4,939,140) (0.53 g, 2.02 mmol) and warm to room temperature overnight. Dilute with methanol (0.2 M) and add concentrated HCl (10 eq.) and stir at room temperature. Pour into water after reaction complete by HPLC and extract with methylene chloride, dry over sodium sulfate, filter and concentrate in vacuo. Purification of the residue over silica gel (20% hexane in ethyl acetate) affords the title compound as a white powder (0.44 g, 71%): MS (APCI-pos mode) m/z (rel intensity) 364.1 (100), 366.1 (40).

Example 12

1-(4-Hydroxy-cyclohexyl)-3-(3-methyl-benzofuran-2-ylmethyl)-pyrrolidin-2-one

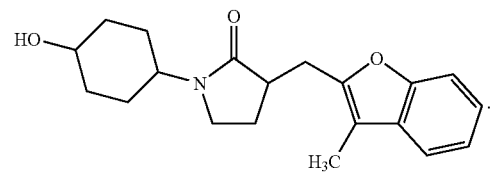

Using the procedure to synthesize Example 3 and using reagents 1-[4-(tert-butyldimethyl-silanyloxy)-cyclohexyl]-pyrrolidin-2-one (500 mg, 1.68 mmol) and 2-bromomethyl-3-methyl-benzofuran (567 g, 2.52 mmol) afford the title compound as a tan powder (295 mg, 54%): Mass spectrum (apci) m/z=328.1 (M+H).

Example 13

3-(3-Chloro-6-hydroxy-benzo[b]thiophen-2-ylmethyl)-1-cyclohexyl-pyrrolidin-2-one

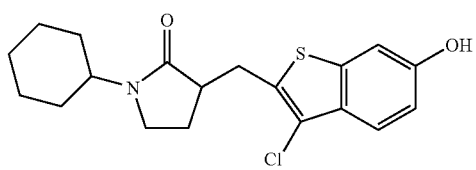

Dissolve 3-(3-chloro-6-methoxy-benzo[b]thiophen-2-yl-methyl)-1-cyclohexylpyrrolidin-2-one (1.122 g, 2.97 mmol) and 2-methyl-2 propene (0.5 mL) in dichloromethane (30 mL) and cool to 0° C. Slowly add boron tribromide (2.23 g, 8.91 mmol) and warm to room temperature. Stir for 1 hour and quench with ice. Extract with dichloromethane, dry with sodium sulfate, filter, and concentrate to give the title compound (1.121 g, 99%) as a light brown solid: Mass spectrum (apci) m/z=364.2 (M+H).

Example 14

4-[3-Chloro-2-(1-cyclohexyl-2-oxo-pyrrolidin-3-ylmethyl)-benzo[b]thiophen-6-yloxymethyl]-benzoic acid

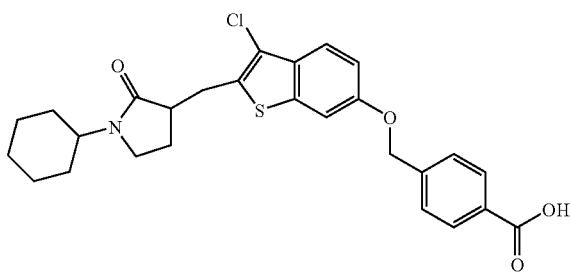

Charge a vial with 3-(3-chloro-6-hydroxy-benzo[b]thiophen-2-ylmethyl)-1-cyclohexyl-pyrrolidin-2-one (175 mg, 0.481 mmol) and dissolve in acetone (0.3 M). Add NaI (72 mg, 0.481 mmol) and Cs$_2$CO$_3$ (1.25 g, 3.85 mmol) and stir at room temperature for 5 minutes. Add 4-bromomethyl-benzoic acid methyl ester (220 mg, 0.96 mmol) and heat to 50° C. overnight. Cool to room temperature, filter, concentrate, and purify over silica gel to afford 4-[3-chloro-2-(1-cyclohexyl-2-oxo-pyrrolidin-3-ylmethyl)-benzo[b]thiophen-6-yloxymethyl]-benzoic acid methyl ester. Dissolve in ethanol (5 mL) and water (1 mL) and add potassium hydroxide (162 mg, 2.88 mmol) and heat to 50° C. overnight. Cool to room temperature filter and dry to afford the title compound (146 mg, 61%) as a white solid: Mass spectrum (apci) m/z=498.2 (M+H).

Example 15

3-[3-Chloro-6-(3-dimethylamino-propoxy)-benzo[b]thiophen-2-ylmethyl]-1-cyclohexyl-pyrrolidin-2-one hydrochloride salt

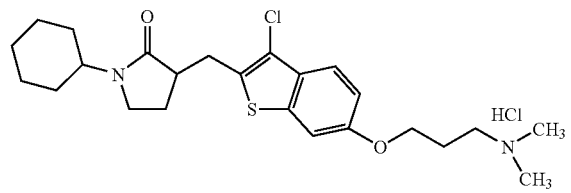

Using the procedure to synthesize Example 12 and using reagents 3-(3-chloro-6-hydroxy-benzo[b]thiophen-2-ylmethyl)-1-cyclohexyl-pyrrolidin-2-one (150 mg, 0.412 mmol), (3-bromo-propyl)-dimethyl-amine hydrochloride (167 mg, 0.824 mmol), sodium iodide (62 mg, 0.412 mmol), and cesium carbonate (1.07 g, 3.30 mmol) afford the freebase of the title compound. Dissolve freebase in dichloromethane (5 mL) and add HCl in ether (2M, 0.4 mL), concentrate to give title compound (105 mg, 52%) as a yellow solid: Mass spectrum (apci) m/z=449.3 (M+H).

Example 16

4-[3-Chloro-2-(1-cyclohexyl-2-oxo-pyrrolidin-3-ylmethyl)-benzo[b]thiophen-6-yloxy]-butyric acid

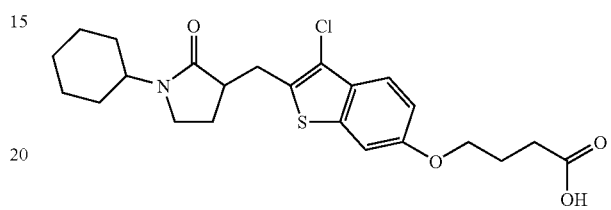

Using the procedure to synthesize Example 12 and using reagents 3-(3-chloro-6-hydroxy-benzo[b]thiophen-2-ylmethyl)-1-cyclohexyl-pyrrolidin-2-one (175 mg, 0.481 mmol), 4-bromo-butyric acid tert-butyl ester (215 mg, 0.962 mmol), sodium iodide (72 mg, 0.481 mmol), and cesium carbonate (1.25 g, 3.85 mmol) afford crude 4-[3-chloro-2-(1-cyclohexyl-2-oxo-pyrrolidin-3-ylmethyl)-benzo[b]thiophen-6-yloxy]-butyric acid tert-butyl ester. Dissolve ester in trifluoroacetic acid (25 mL) and stir for 1.5 hr. Evaporate and dissolve in 1M NaOH and wash with ether. Bring aqueous layer to a pH of ~2 with 6M HCl, filter, and dry. Purified on silica gel (30-50% ethyl acetate in hexanes) to give the title compound (105 mg, 49%) as a tan solid: Mass spectrum (apci) m/z=450.1 (M+H).

Example 17

1-Cyclohexyl-3-[5-(2-fluoro-pyridin-4-yl)-benzo[b]thiophen-2-ylmethyl]-pyrrolidin-2-one

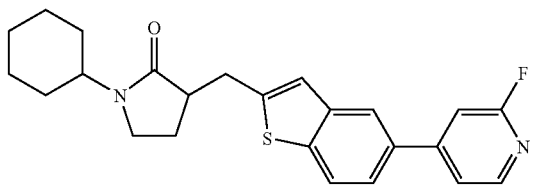

Add 3-(5-bromo-benzo[b]thiophen-2-ylmethyl)-1-cyclohexyl-pyrrolidin-2-one (250 mg, 0.64 mmol), 2-fluoropyridine-4-boronic acid (200 mg, 1 mmol), LiCl (10 eq) and Pd(PPh$_3$)$_4$ (0.05 eq) into a solution of dioxane (10 mL) and 2M Na$_2$CO$_3$ (2 mL) and heat at 80° C. for 1 hour. Pour the reaction mixture into water and extract with ethyl acetate. Dry over sodium sulfate, filter, and concentrate. Purify by silica gel (20-50% ethyl acetate in hexanes) to give the title compound as a pale yellow powder (260 mg, 58%): MS (APCI-pos mode) m/z (rel intensity): 409.2 (M+H, 100%).

Example 18

4-[2-(1-Cyclohexyl-2-oxo-pyrrolidin-3-ylmethyl)-benzo[b]thiophen-5-yl]-benzoic acid

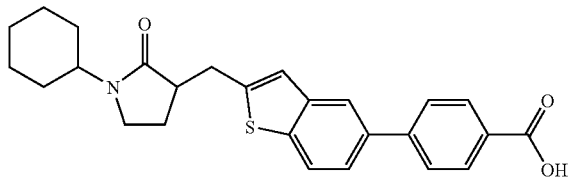

Heat a mixture of 4-[2-(1-cyclohexyl-2-oxo-pyrrolidin-3-ylmethyl)-benzo[b]thiophen-5-yl]-benzoic acid methyl ester (250 mg, 0.64 mmol), LiOH.H$_2$O (10 eq) into a dioxane (5 mL) and water (2 mL) at 80° C. for 1 hour. Add 2 M HCl (1 mL) and extract the mixture with ethyl acetate. Dry over sodium sulfate, filter, and concentrate. Purify by silica gel (20-50% ethyl acetate in hexanes) to give the title compound as a white powder (110 mg, 65%): MS (APCI-pos mode) m/z (rel intensity): 434.1 (M+H, 100%).

Example 19

3-(3-Chloro-benzo[b]thiophen-2-ylmethyl)-trans-1-(4-hyroxyl-cyclohexyl)-piperidin-2-one

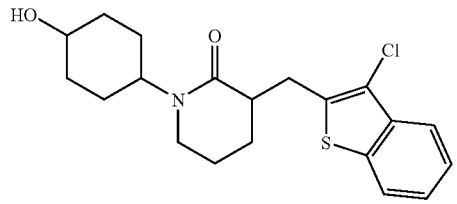

Place trans-1-{4-(tert-Butyl-dimethyl-silanyloxy)-cyclohexy}3-(3-chloro-benzo[b]thiophen-2-ylmethyl)-piperidin-2-one, obtained below, (310 mg, 0.63 mmol) in 5% HCl/EtOH (10 ml), and stir 2 h at room temperature. Evaporate, dissolve residue in methylene chloride, wash with sodium bicarbonate, and dry over sodium sulfate. Evaporate and silica gel chromatography (Ethyl acetate-hexanes 0-100%) affords 194 mg (81%) of the title compound: Mass spectrum (apci) m/z=377 (M+H).

Example 20

3-(3-Chloro-benzo[b]thiophen-2-ylmethyl)-cis-1-(4-hyroxyl-cyclohexyl)-piperidin-2-one

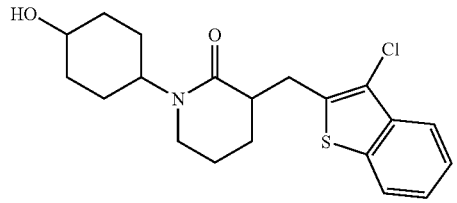

Place cis-1-{4-(tert-Butyl-dimethyl-silanyloxy)-cyclohexy}3-(3-chloro-benzo[b]thiophen-2-ylmethyl)-piperidin-2-one, obtained below, (166 mg, 0.33 mmol) in 5% HCl/EtOH (10 ml), and stir 2 h at room temperature. Evaporate, dissolve residue in methylene chloride, wash with sodium bicarbonate, and dry over sodium sulfate. Evaporate and silica gel chromatography (Ethyl acetate-hexanes 0-100%) affords 21 mg (19%) of the title compound: Mass spectrum (apci) m/z=377 (M+H).

Pharmacological Methods

In the following section binding assays as well as functional assays useful for evaluating the efficiency of the compounds of the invention are described.

11β-HSD Type 1 Enzyme Assay

Human 11β-HSD type 1 activity is measured by assaying NADPH production by fluorescence assay. Solid compounds are dissolved in DMSO to a concentration of 10 mM. Twenty microliters of each are then transferred to a column of a 96-well polypropylene Nunc plate where they are further diluted 50-fold followed by subsequent two-fold titration, ten times across the plate with additional DMSO using a Tecan Genesis 200 automated system. Plates are then transferred to a Tecan Freedom 200 system with an attached Tecan Temo 96-well head and an Ultra 384 plate reader. Reagents are supplied in 96-well polypropylene Nunc plates and are dispensed individually into black 96-well Molecular Devices High Efficiency assay plates (40 µL/well capacity) in the following fashion: 9 µL/well of substrate (2.22 mM NADP, 55.5 µM Cortisol, 10 mM Tris, 0.25% Prionex, 0.1% Triton X100), 3 µL/well of water to compound wells or 3 µL to control and standard wells, 6 µL/well recombinant human 11β-HSD type 1 enzyme, 2 µL/well of compound dilutions. For ultimate calculation of percent inhibition, a series of wells are added that represent assay minimum and maximum: one set containing substrate with 667 µM carbenoxolone (background), and another set containing substrate and enzyme without compound (maximum signal). Final DMSO concentration is 0.5% for all compounds, controls and standards. Plates are then placed on a shaker by the robotic arm of the Tecan for 15 seconds before being covered and stacked for a three hour incubation period at room temperature. Upon completion of this incubation, the Tecan robotic arm removes each plate individually from the stacker and places them in position for addition of 5 µL/well of a 250 µM carbenoxolone solution to stop the enzymatic reaction. Plates are then shaken once more for 15 seconds then placed into an Ultra 384 microplate reader (355EX/460EM) for detection of NADPH fluorescence.

Acute In Vivo Cortisone Conversion Assay

In general, compounds are dosed orally into mice, the mice are challenged with a subcutaneous injection of cortisone at a set timepoint after compound injection, and the blood of each animal is collected some time later. Separated serum is then isolated and analyzed for levels of cortisone and cortisol by LC-MS/MS, followed by calculation of mean cortisol and percent inhibition of each dosing group. Specifically, male C57BL/6 mice are obtained from Harlan Sprague Dawley at average weight of 25 grams. Exact weights are taken upon arrival and the mice randomized into groups of similar weights. Compounds are prepared in 1% w-w HEC, 0.25% w-w polysorbate 80, 0.05% w-w Dow Corning antifoam #1510-US at various doses based on assumed average weight of 25 grams. Compounds are dosed orally, 200 µl per animal, followed by a subcutaneous dose, 200 μl per animal, of 30 mg/kg cortisone at 1 to 24 hours post compound dose. At 10 minutes post cortisone challenge, each animal is euthanized for 1 minute in a $CO_2$ chamber, followed by blood collection via cardiac puncture into serum separator tubes. Once fully clotted, tubes are spun at 2500×g, 4° C. for 15 minutes, the serum is transferred to wells of 96-well plates (Corning Inc, Costar #4410, cluster tubes, 1.2 ml, polypropylene), and the plates frozen at −20° C. until analysis by LC-MS/MS. For analysis, serum samples are thawed and the proteins are precipitated by the addition of acetonitrile containing $d_4$-cortisol internal standard. Samples are vortex mixed and centrifuged. The supernatant is removed and dried under a stream of warm nitrogen. Extracts are reconstituted in methanol/water (1:1) and injected onto the LC-MS/MS system. The levels of cortisone and cortisol are assayed by selective reaction monitoring mode following positive ACPI ionization on a triple quadrupole mass spectrophotometer.

All of the examples provided herein have activity in the 11β-HSD type 1 enzyme assay with $IC_{50}$ of less than 20 μM. The assay results are given below for the indicated compound in the 11β-HSD type 1 enzyme assay.

| Example | 11β-HSD type 1 enzyme assay $IC_{50}$ (nM) |
|---|---|
| 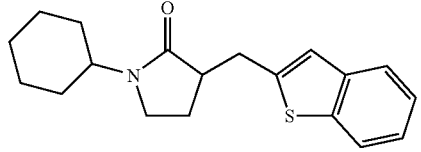 1 | 190 |
| 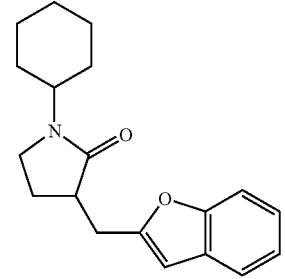 3 | 682 |
| 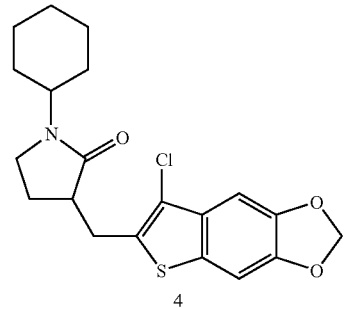 4 | 162 |
| 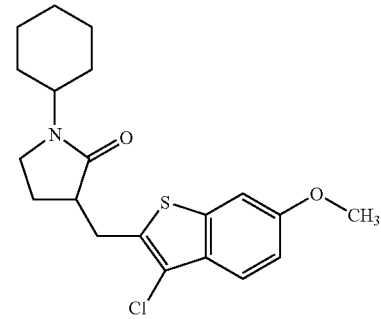 8 | 508 |

| Example | 11β-HSD type 1 enzyme assay IC$_{50}$ (nM) |
|---|---|
| 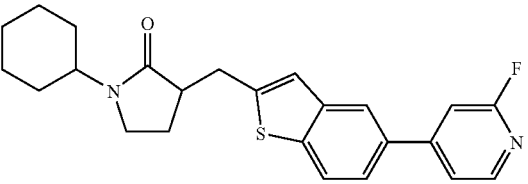 17 | 257 |
| 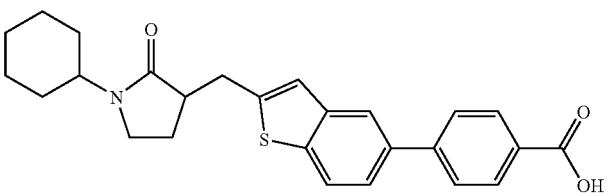 18 | 427 |
| 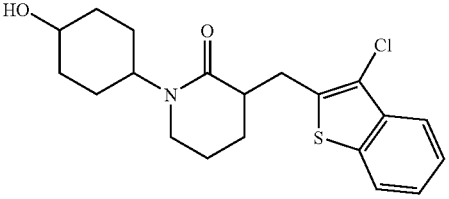 19 | 276 |

A compound of formula (I) can be formulated with common excipients, diluents, or carriers, and formed into tablets, capsules, and the like. Examples of excipients, diluents, and carriers that are suitable for formulation include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethyl glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, a compound of formula (I) or a pharmaceutically acceptable salt thereof, is suited to formulation as sustained release dosage forms. The formulations can also be so constituted that they release the active ingredient only or preferably in a particular part of the intestinal tract, possibly over a period of time. Such formulations would involve coatings, envelopes, or protective matrices that may be made from polymeric substances or waxes.

The particular dosage of a compound of formula (I) or a pharmaceutically acceptable salt thereof required to constitute an effective amount according to this invention will depend upon the particular circumstances of the conditions to be treated. Considerations such as dosage, route of administration, and frequency of dosing are best decided by the attending physician. Generally, accepted and effective dose ranges for oral or parenteral administration will be from about 0.1 mg/kg/day to about 10 mg/kg/day which translates into about 6 mg to 600 mg, and more typically between 30 mg and 200 mg for human patients. Such dosages will be administered to a patient in need of treatment from one to three times each day or as often as needed to effectively treat a disease selected from (1) to (20) above.

The compounds of the present invention can be administered alone or in the form of a pharmaceutical composition, that is, combined with pharmaceutically acceptable carriers, or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

The compounds claimed herein can be administered by a variety of routes. In effecting treatment of a patient afflicted with or at risk of developing the disorders described herein, a compound of formula (I) or a pharmaceutically acceptable salt thereof can be administered in any form or mode that makes the compound bioavailable in an effective amount, including oral and parenteral routes. For example, the active compounds can be administered rectally, orally, by inhalation, or by the subcutaneous, intramuscular, intravenous, transdermal, intranasal, rectal, occular, topical, sublingual, buccal, or other routes. Oral administration may be preferred for treatment of the disorders described herein. However, oral administration is the preferred route. Other routes include the intravenous route as a matter of convenience or to avoid potential complications related to oral administration.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

For the purpose of oral therapeutic administration, the compounds may be incorporated with excipients and used in the form of tablets, troches, capsules, elixirs, suspensions, syrups, wafers, chewing gums and the like. These preparations should contain at least 4% of the active ingredients, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, microcrystalline cellulose, gum tragacanth or gelatin; excipients such as dicalcium phosphate, starch, or lactose; disintegrating agents such as alginic acid, Primogel, corn starch and the like; lubricants such as talc, hydrogenated vegetable oil, magnesium stearate or Sterotex; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used. In those instances where oral administration is impossible or not preferred, the composition may be made available in a form suitable for parenteral administration, e.g., intravenous, intraperitoneal or intramuscular.

We claim:
1. A compound of formula I:

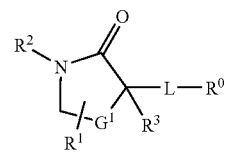

or a pharmaceutically acceptable salt thereof wherein $R^0$ is

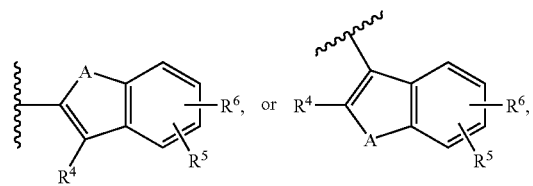

wherein the zig-zag mark represents the point of attachment to the $R^0$ position in Formula I;

$G^1$ is methylene;

L is —CH$_2$—;

A is —S— or —O—;

$R^1$ is Hydrogen;

$R^2$ is

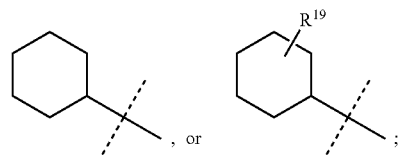

wherein the dashed line indicates the point of attachment to the $R^2$ position in formula I;

$R^3$ is hydrogen;

$R^4$ is hydrogen, $(C_1-C_4)$alkyl optionally substituted with one to three halogens, or halo;

$R^5$ is hydrogen;

$R^6$ is hydrogen, hydroxy, $(C_1-C_4)$alkoxy optionally substituted with one to three halogens, halo, $Ar^2$, $Het^2$, —O—$(C_1-C_4)$alkyl-$Ar^2$, —O—$(C_1-C_4)$alkyl-C(O)OH, or —O—$(C_1-C_4)$alkyl-N($R^{13}$)($R^{14}$); wherein $R^{13}$ and $R^{14}$ are each independently hydrogen or —$(C_1-C_4)$alkyl;

or when $R^0$ is

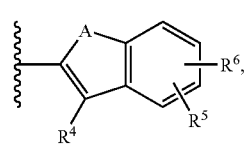

then $R^5$ and $R^6$ may combine with the ring atoms to which they are attached to form

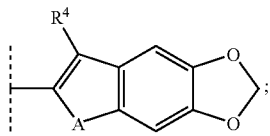

Ar$^1$ is phenyl;
Ar$^2$ is Ar$^1$ optionally substituted with —C(O)OH;
Het$^1$ is pyridinyl;
Het$^2$ is Het$^1$ optionally substituted with —C(O)OH; and
R$^{19}$ is hydroxy.

2. A compound of claim 1, or a pharmaceutically acceptable salt thereof, wherein
R$^0$ is

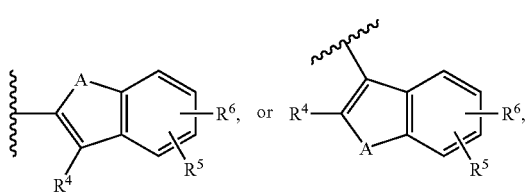

wherein the zig-zag mark represents the point of attachment to the R$^0$ position in Formula I;
G$^1$ is methylene;
L is —CH$_2$—;
A is —S— or —O—;
R$^1$ is hydrogen;
R$^2$ is

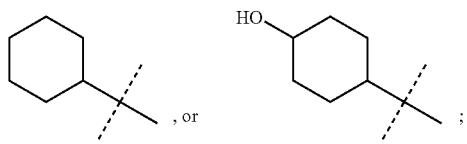

wherein the dashed line indicates the point of attachment to the R$^2$ position in formula I;
R$^3$ is hydrogen;
R$^4$ is hydrogen, —CH$_3$, or halo;
R$^5$ is hydrogen;
R$^6$ is hydrogen, hydroxy, —OCH$_3$, halo, Ar$^2$, Het$^2$, —O—CH$_2$-phenyl-C(O)OH, —O—CH$_2$CH$_2$CH$_2$—C(O)OH, or —O—CH$_2$CH$_2$CH$_2$—N(CH$_3$)$_2$;
or when R$^0$ is

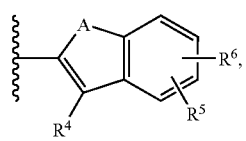

then $R^5$ and $R^6$ may combine with the ring atoms to which they are attached to form

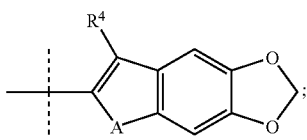

Ar$^2$ is phenyl-C(O)OH; and
Het$^2$ is pyridinyl-C(O)OH.

3. A compound according to claim 2, or a pharmaceutically acceptable salt thereof, wherein said compound is selected from the group consisting of:
  3-Benzo[b]thiophen-2-ylmethyl-1-cyclohexyl-pyrrolidin-2-one;
  3-(3-Chloro-benzo[b]thiophen-2-ylmethyl)-1-cyclohexyl-pyrrolidin-2-one;
  3-Benzofuran-2-ylmethyl-1-cyclohexyl-pyrrolidin-2-one;
  3-(7-Chloro-1,3-dioxa-5-thia-s-indacen-6-ylmethyl)-1-cyclohexyl-pyrrolidin-2-one;
  1-Cyclohexyl-3-(3-methyl-benzo[b]thiophen-2-ylmethyl)-pyrrolidin-2-one;
  3-(3-Chloro-6-fluoro-benzo[b]thiophen-2-ylmethyl)-1-cyclohexyl-pyrrolidin-2-one;
  3-(5-Chloro-benzo[b]thiophen-3-ylmethyl)-1-cyclohexyl-pyrrolidin-2-one;
  3-(3-Chloro-6-methoxy-benzo[b]thiophen-2-ylmethyl)-1-cyclohexyl-pyrrolidin-2-one;
  3-(5-Bromo-benzo[b]thiophen-2-ylmethyl)-1-cyclohexyl-pyrrolidin-2-one;
  3-(6-Bromo-benzo[b]thiophen-2-ylmethyl)-1-cyclohexyl-pyrrolidin-2-one;
  3-(3-Chloro-benzo[b]thiophen-2-ylmethyl)-1-(cis-4-hydroxy-cyclohexyl)-pyrrolidin-2-one;
  3-(3-Chloro-benzo[b]thiophen-2-ylmethyl)-1-(4-hydroxy-cyclohexyl)-pyrrolidin-2-one;
  1-(4-Hydroxy-cyclohexyl)-3-(3-methyl-benzofuran-2-ylmethyl)-pyrrolidin-2-one;
  3-(3-Chloro-6-hydroxy-benzo[b]thiophen-2-ylmethyl)-1-cyclohexyl-pyrrolidin-2-one;
  4-[3-Chloro-2-(1-cyclohexyl-2-oxo-pyrrolidin-3-ylmethyl)-benzo[b]thiophen-6-yloxymethyl]-benzoic acid;
  3-[3-Chloro-6-(3-dimethylamino-propoxy)-benzo[b]thiophen-2-ylmethyl]-1-cyclohexyl-pyrrolidin-2-one hydrochloride salt;
  3-[3-Chloro-6-(3-dimethylamino-propoxy)-benzo[b]thiophen-2-ylmethyl]-1-cyclohexyl-pyrrolidin-2-one;
  4-[3-Chloro-2-(1-cyclohexyl-2-oxo-pyrrolidin-3-ylmethyl)-benzo[b]thiophen-6-yloxy]-butyric acid;
  1-Cyclohexyl-3-[5-(2-fluoro-pyridin-4-yl)-benzo[b]thiophen-2-ylmethyl]-pyrrolidin-2-one; and
  4-[2-(1-Cyclohexyl-2-oxo-pyrrolidin-3-ylmethyl)-benzo[b]thiophen-5-yl]-benzoic acid.

4. A pharmaceutical composition which comprises a compound of claim 1 and a pharmaceutically acceptable carrier.

* * * * *